US005792839A

United States Patent [19]
Kahne

[11] Patent Number: 5,792,839
[45] Date of Patent: Aug. 11, 1998

[54] CATALYTIC METHOD OF FORMING A GLYCOSIDIC LINKAGE

[75] Inventor: Daniel Evan Kahne, Princeton, N.J.

[73] Assignee: Trustees of Princeton University, Princeton, N.J.

[21] Appl. No.: 783,299

[22] Filed: Jan. 10, 1997

Related U.S. Application Data

[60] Division of Ser. No. 198,271, Feb. 18, 1994, which is a continuation-in-part of Ser. No. 21,391, Feb. 23, 1993.

[51] Int. Cl.$^6$ .............................. C07G 3/00; C07H 15/00
[52] U.S. Cl. .......................... 536/1.11; 536/4.1; 536/6.4; 536/17.2; 536/18.5; 536/18.6; 536/124; 536/126
[58] Field of Search ........................ 536/1.11, 4.1, 536/6.4, 17.2, 18.5, 18.6, 124, 126

[56] References Cited

U.S. PATENT DOCUMENTS

| | | |
|---|---|---|
| 4,046,886 | 9/1977 | Smith . |
| 4,130,643 | 12/1978 | Smith . |
| 4,130,667 | 12/1978 | Smith . |
| 4,148,887 | 4/1979 | Smith . |
| 4,148,893 | 4/1979 | Smith . |
| 4,148,917 | 4/1979 | Smith . |
| 4,148,924 | 4/1979 | Smith et al. . |
| 4,470,976 | 9/1984 | Miner et al. . |
| 4,548,922 | 10/1985 | Carey et al. . |
| 4,746,508 | 5/1988 | Carey et al. . |
| 4,865,848 | 9/1989 | Cheng et al. . |
| 4,902,505 | 2/1990 | Pardridge et al. . |
| 5,338,837 | 8/1994 | Kahne . |

FOREIGN PATENT DOCUMENTS

| | | |
|---|---|---|
| 0 285 285 | 10/1988 | European Pat. Off. . |
| 0 444 778 A1 | 9/1991 | European Pat. Off. . |
| WO 90/03172 | 4/1990 | WIPO . |
| WO 90/13298 | 11/1990 | WIPO . |
| WO 93/11772 | 6/1993 | WIPO . |

OTHER PUBLICATIONS

Feizi et al. *TIBS*, 1985, 24.
Rademacher et al. *Annu. Rev. Biochem.* 1988, 57, 785.
Feizi *TIBS*, 1991, 84.
Dennis and Laferte *Cancer Res.* 1985, 45, 6034.
Fishman *J. Membr. Biol.* 1982, 69, 85.
Markwell et al. *PNAS USA*, 1981, 78, 5406.
Wiley and Skehel *J. Annu. Rev. Biochem.* 1987, 56, 365.
Kleinman et al. *PNAS USA*, 1979, 76, 3367.
Walz et al. *Science* 1990, 250.
Furka et al. *Int. Peptide Protein Res.* 1991, 37, 487.
Lam et al. *Nature* 1991, 354, 82.
Houghten *Nature* 1991, 354, 84.
Zuckermann et al. *Proc. Natl. Acad. Sci. USA* 1992, 89, 4505.
Petithory *Proc. Natl. Acad. Sci. USA*, 1991, 88, 11510.
Geyse *Proc. Natl. Acad. Sci. USA*, 1984, 81, 3998.
Houghten *Proc. Natl. Acad. Sci. USA*, 1985, 82, 5131.
Fodor *Science* 1991, 251, 767.

Bieber et al. *J. Antibiot.* 1987, 40, 1335.
Kolar et al. *Carbohydr. Res.* 1990, 208, 111.
Arcamone, F. *Doxorubicin Anticancer Antibiotics:* Academic Press: New York, 1981.
Suzuki et al. *J. Am. Chem. Soc.* 1990, 112, 8895.
Barany, G. and Merrifield, R.B. 1979, in *The Peptides*, Gross, E. and Meienhofer, J. Eds., Academic Press, New York, vol. 2, pp. 1–284 (Table of Contents Provided).
Frechet and Schuerch *J. Am. Chem. Soc.* 1971, 93, 492.
Frechet, *Polymer–supported Reactions in Organic Synthesis*, p. 407, P. Hodge and D.C. Sherington, Eds., John Wiley & Sons, 1980.
Douglas et al. *J. Am. Chem. Soc.* 1991, 113, 5095–5097.
Kahne et al. *J. Am. Chem. Soc.* 1989, vol. 111, No. 17, 6881–6882.
Binkley *Modern Charbohydrate Chemistry*, Marcel Dekker, Inc: New York, 1988 (v–vii and ix–xi).
Paulsen *Angew. Chem. Int. Ed. Engl.* 1982, vol. 21, No. 3, pp. 155–173.
Ito and Ogawa *Tetrahedron Lett.* 1987, vol. 28, No. 24, 2723–2726.
Lonn *Glycoconjugate J.* 1987, 4, 117.
Mootoo et al. *J. Am. Chem. Soc.* 1989, 111, 8540.
Evans et al. *J. Am. Chem. Soc.* 1990, 112, 7001.
Veeneman et al. *Tetrahedron Lett.* 1990, 31, 1331.
Nakamura *J. Am. Chem. Soc.* 1983, 105, 7172.
Ikemoto and Schreiber *J. Am. Chem. Soc.* 1990, 112, 9657.
Horita et al. *Tetrahedron*, 1986, 42, 3021.
Oikawa et al. *Tet. Lett.* 1984, 25, 5393.
*Carbohydrates*, Ed. Collns, P.M. Chapman and Hall: New York, 1987.
Mootoo et al. *J. Am. Chem. Soc.* 1988, 110, 5583.
Veeneman and van Boom *Tet. Lett.* 1990, 31, 275.
Mehta and Pinto *Tet. lett.* 1991, 32, 4435.
Friesen and Danishefsky *J. Am. Chem. Soc.* 1989, 111, 6656.
Halcomb and Danishefsky *J. Am. Chem. Soc.* 1989, 111, 6661.
Nicolaou et al. *J. Am. Chem. Soc.* 1984, 106, 4189.
Barrett et al. *J. Am. Chem. Soc.* 1989, 111, 1392.
Martin et al. *Carbohydr. Res.* 1983, 115, 21.

(List continued on next page.)

*Primary Examiner*—Herbert J. Lilling
*Attorney, Agent, or Firm*—Lowe, Price, LeBlanc & Becker

[57] ABSTRACT

The invention relates to methods that permit the rapid construction of oligosaccharides and other glycoconjugates. Methods for forming multiple glycosidic linkages in solution in a single step are disclosed. The invention takes advantage of the discovery that the relative reactivity of glycoside residues containing anomeric sulfoxides and nucleophilic functional groups can be controlled. In another aspect of the invention, the reactivity of activated anomeric sugar sulfoxides is utilized in a solid phase method for the formation of glycosidic linkages. The methods disclosed may be applied to the preparation of specific oligosaccharides and other glycoconjugates, as well as to the preparation of glycosidic libraries comprising mixtures of various oligosaccharides, including glycoconjugates, which can be screened for biological activity.

26 Claims, 21 Drawing Sheets

OTHER PUBLICATIONS

Giese et al. *Angew Chem. Int. Ed. Engl.* 1987, 26, 233.
*Template Chromatography of Nucleic Acids and Proteins*, Schott, H. Marcel Dekker, Inc.: New York 1984 pp. (iii–vii).
*Glycoconjugates: Composition, Structure and Function*, Allen, H.J., Kisailus, E.C., Eds. Marcel Dekker: NY 1992.
Inhoffen et al. *Croatica Chem. Acta*, 1957, 29, 329.
Trost et al. *J. Am. Chem. Soc.* 1977, 99, 8116.
Stork and Hagedorn *J. Am. Chem. Soc.* 1978, 100, 3609.
Binkley, R. W. *Modern Carbohydrate Chemistry*, Marcel Dekker, Inc.: New York, 1988.
Ferrier et al. *Carbohydr. Res.* 1973, vol. 27, pp. 55–61.
Mukaiyama et al. *Chem. Lett.* 1979, 487.
Van Cleve *Carbohydr. Res.* 1979, 70, 161.
Hanessian et al. *Carbohydr. Res.* 1980, 80, C17.
Garegg et al. *Carbohydr. Res.* 1983, vol. 116, pp. 162–165.
Nicolaou et al. *J. Am. Chem. Soc.* 1983, vol. 105, No. 8, 2430–2433.
Ito et al. *Tetrahedron Letters*, 1987, vol. 28, No. 40, pp. 4701–4704.
Lonn, *Carbohydrate Research*, 1985, vol. 139, pp. 105–113.
Andersson et al., pp. 3919–3922, "Synthesis of 1.2 CIS-Linked Glycosides using Dimethi(methylio)Sulfonium Triflate as Promoter and Thiglycosides and Glycosyl Donors".
Ito et al., pp. 1061–1064, "Benzenseleneyl Triflate as a Promoter of Thiglycosides: A New Method for O–Glycosylation Using Thioglycosides".
Lettsinger et al., *Biochemistry*, 1989, vol. 86, pp. 6553–6556.
Brown et al. *Tetrahedron Letters*, 1988, vol. 29, No. 38, pp. 4873–4876.
Dasgupta et al., *Carbohydrate Research*, 1988, vol. 177, pp. c13–c17.
Gordon et al., *Proc. Natl. Acad. Sci.*, 1985, vol. 82, pp. 7419–7423.
Malinowska et al., *Proc. Natl. Acad. Sci.*, 1981, vol. 78, pp. 5908–5912.
Spigelman et al., Neurosurgery, 1983, vol. 12, No. 6, pp. 606–612.
Oehike, *Chemical Abstracts*, 94:98644b.
Kramer et al., *Chemical Abstracts*, 115:72019d
Oehike, *Chemical Abstracts*, 92:59167n.
Oehike, *Pharmazie*, 1979, vol. 34, H.7., pp. 383–386.
Riccio et al., *J. Org. Chem.*, 1986, vol. 51, No. 4, pp. 533–536.
Gerald F. Joyce, *Scientific American*, 1992, Dec., pp. 90–97.
Ito et al., Tetrahedron Letters, 1988, vol. 29, No. 9, pp. 1061–1064.
Kuhn et al., *Chemical Abstracts*, May 25, 1992, 116; 214811 No. 21.
Abstract. Lieb 165 Ann Chem 1992 (4) 407–9.
Ginsburg et al., *Academic Press (Boston )*, 1987, vol. 138, Part E.
*Carbohydrate Research*, 1992, vol. 233, pp. 245–250.
Hakomori TIBS, 1984, 45.
Eby and Schuerch, *Carbohydr. Res.*)1975, 39, 151.
Deferrari, J. O. et al. *Carbohydrate. Res.*, 1967, 4, 432 (1967).
Deferrari, J. O. *Methods in Carbohydrate Chemistry*, 1972, 6, 65.
Bovin, N.V. et al. *Akad. Nauk SSR, Ser. Khim.*, 1981, 1638.
Kovac, P. *Carbohydr. Res.*, 1986, 153, 168.
Hamacher, K. *Carbohydr. Res.*, 1984, 128, 291.
Pavliak, V. and Kovac, P. *Carbohydr. Res.*, 1991, 210, 333.
Bovin, N.V. et al., *Carbohydr. Res.*, 1981, 98, 25.
Merrifield, R.B. *J. Am. Chem. Soc.*, 1963, 85, 2149.
Kunz, H. and Harreus, A., *Liebigs Ann. Chem.* 1982–41.

SCHEME 1 PREMIXED 1(3.0eq), 2(2.0eq) AND 3(1.0eq), Et$_2$O-CH$_2$Cl$_2$(1:1), HC≡CCOOCH$_3$(20eq), TfOH(0.05eq), −78°C TO −70°C, 45MIN, THEN QUENCHED WITH SAT. NaHCO$_3$ SOLUTION.

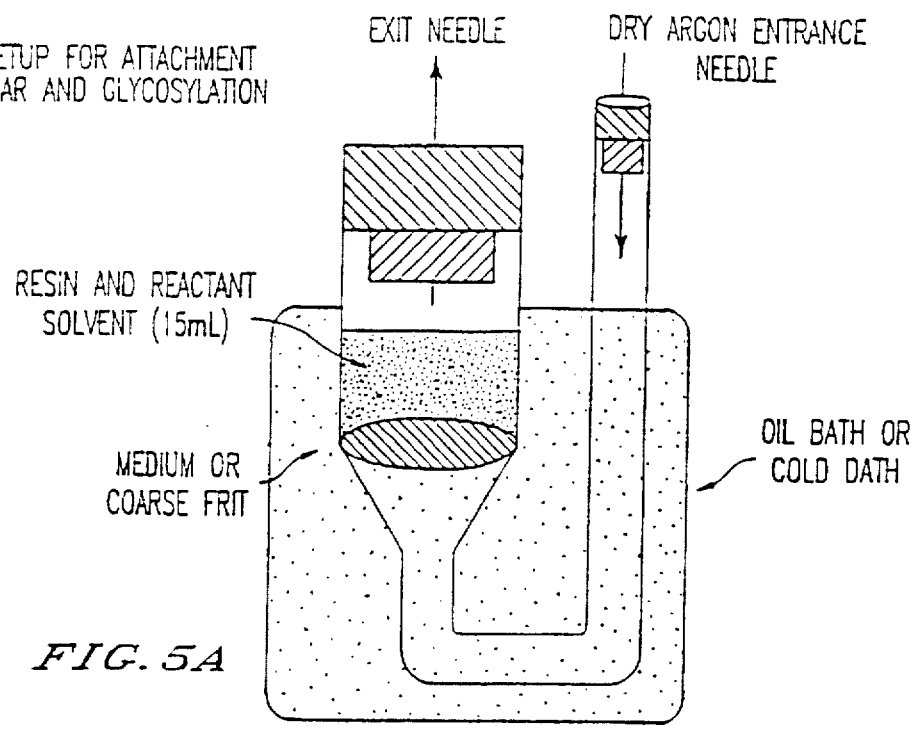
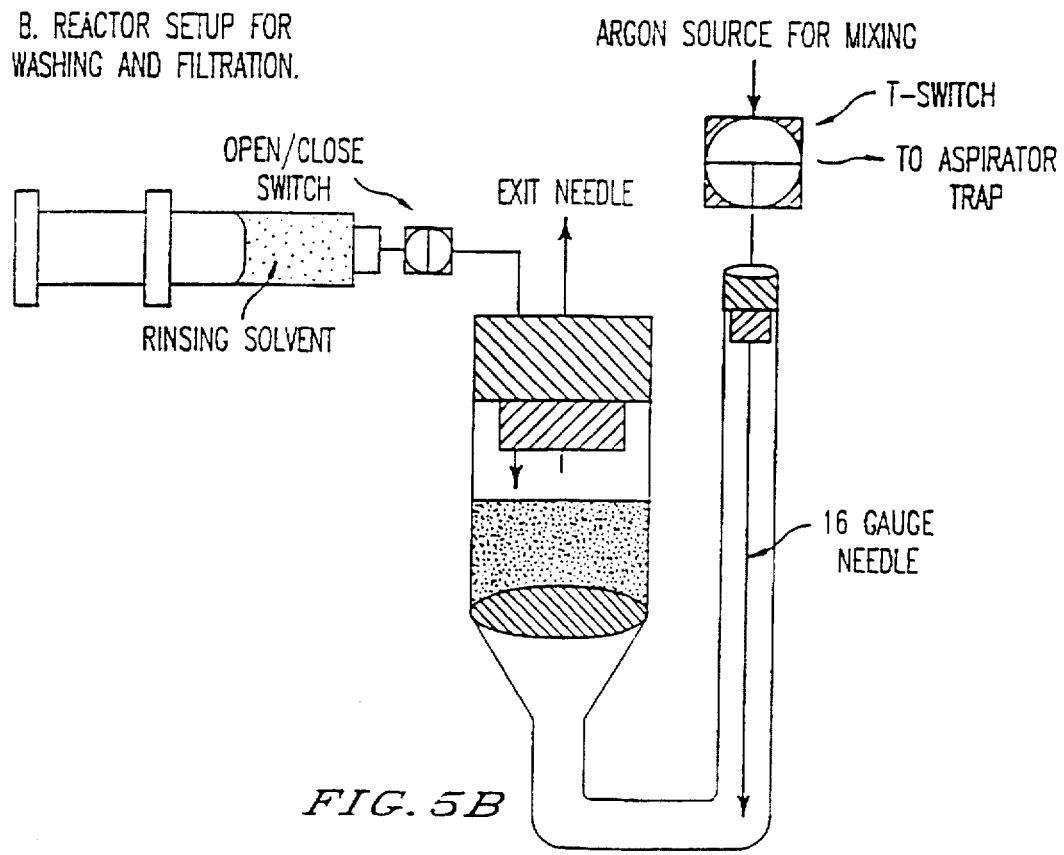

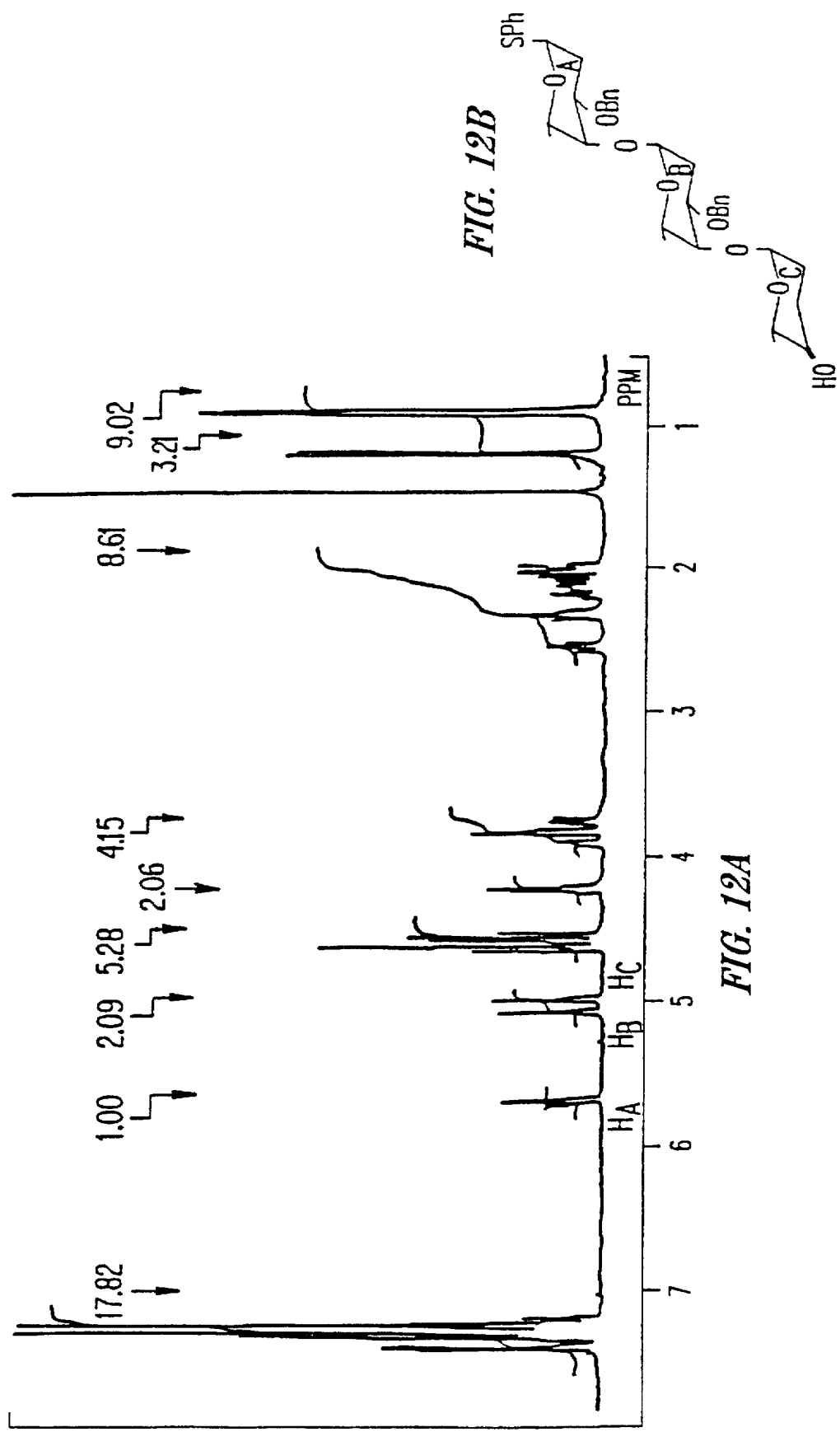

CATALYTIC METHOD OF FORMING A GLYCOSIDIC LINKAGE

CROSS REFERENCE TO RELATED APPLICATIONS

The present application is a division application of prior co-pending U.S. application Ser. No. 08/198,271, filed Feb. 18, 1994, which is a continuation-in-part of prior co-pending U.S. application Ser. No. 08/021,391 filed Feb. 23, 1993. The disclosures of both prior applications are incorporated by reference herein.

1. FIELD OF THE INVENTION

The present invention relates generally to methods that permit the rapid construction of oligosaccharides and other glycoconjugates. More particularly, the present invention relates to methods for forming multiple glycosidic linkages in solution in a single step. The present invention takes advantage of the discovery that the relative reactivity of glycoside residues containing anomeric sulfoxides and nucleophilic functional groups can be controlled. In another aspect of the present invention, the reactivity of activated anomeric sugar sulfoxides is utilized in a solid phase method for the formation of glycosidic linkages. The methods disclosed may be applied to the preparation of specific oligosaccharides and other glycoconjugates, as well as to the preparation of glycosidic libraries comprising mixtures of various oligosaccharides, including glycoconjugates, which can be screened for biological activity.

2. BACKGROUND OF THE INVENTION

2.1. General Background

The oligosaccharide chains of glycoproteins and glycolipids play important roles in a wide variety of biochemical processes. Found both at cell surfaces and circulating in biological fluids, these glycosidic residues act as recognition signals that mediate key events in normal cellular development and function. They are involved in fertilization, embryogenesis, neuronal development, hormonal activities, inflammation, cellular proliferation, and the organization of different cell types into specific tissues. They are also involved in intracellular sorting and secretion of glycoproteins as well as in the clearance of plasma glycoproteins from circulation.

In addition to their positive role in the maintenance of health, oligosaccharides are also involved in the onset of disease. For instance, oligosaccharides on cell surfaces function as receptors for viruses and toxins, as well as more benign ligands. Modified cell surface carbohydrates have been implicated in tumorigenesis and metastasis. The oligosaccharide structures that mediate inflammation and help prevent infection can, when produced at excessive levels, stimulate the development of chronic inflammatory disease. (Some references on the roles of oligosaccharides produced by eukaryotes in health and disease include: Hakomori *TIBS*, 1984, 45; Feizi et al. *TIBS*, 1985, 24; Rademacher et al. *Annu. Rev. Biochem.* 1988, 57, 785; Feizi *TIBS*, 1991, 84; Dennis and Laferte *Cancer Res.* 1985, 45, 6034; Fishman *J. Membr. Biol.* 1982, 69, 85; Markwell et al. *PNAS USA*, 1981, 78, 5406; Wiley and Skehel *J. Annu. Rev. Biochem.* 1987, 56, 365; Kleinman et al. *PNAS USA*, 1979, 76, 3367; Walz et al. *Science* 1990, 250.)

Although bacteria do not produce the same types of oligosaccharides or other glycoconjugates as eukaryotes, procaryotes nevertheless produce a wide variety of glycosylated molecules. Many such molecules have been isolated and found to have antitumor or antibiotic activity. Bacterially produced glycosylated molecules having potential therapeutic utility include chromomycin, calicheamicin, esperamicin, and the ciclamycins. In all these cases, the carbohydrates residues have been shown to be important to biological activity. However, the precise functions of the carbohydrate residues are not well understood and there is no understanding of structure-activity relationships.

Because of their diverse roles in health and disease, oligosaccharides have become a major focus of research. It is widely accepted that the development of technology to 1) detect and 2) block or otherwise regulate some of the abnormal functions of oligosaccharides would lead to significant improvements in health and well-being. Moreover, it should be possible to exploit some of the normal functions of oligosaccharides (e.g., various recognition processes) for other purposes, including drug delivery to specific cell types. In addition, it may be possible to develop new antitumor agents from synthetic glycosylated molecules reminiscent of glycosylated bacterial antitumor agents.

There are ongoing efforts to develop products related to oligosaccharides, including diagnostic kits for detecting carbohydrates associated with various diseases, vaccines to block infection by viruses that recognize cell surface carbohydrates, drug delivery vehicles that recognize carbohydrate receptors, and monoclonal antibodies, which recognize abnormal carbohydrates, for use as drugs. The timely development of these and other carbohydrate-based biomedical products depends in turn on the availability of technology to produce oligosaccharides and other glycoconjugates rapidly, efficiently, and in practical quantities for basic and developmental research.

In particular, there is a need for methods that permit the rapid preparation of glycosidic libraries comprising mixtures of various oligosaccharides or other glycoconjugates which could then be screened for a particular biological activity. It has been shown, for example, that screening of mixtures of peptides is an efficient way of identifying active compounds and elucidating structure-activity relationships. There are numerous ways to generate chemically diverse mixtures of peptides and determine active compounds. See, for example, Furka et al. *Int. J. Peptide Protein Res.* 1992, 37, 487; Lam et al. *Nature* 1991, 354, 82; Houghten *Nature* 1991, 354, 84; Zuckermann et al. *Proc. Natl. Acad. Sci. USA* 1992, 89, 4505; Petithory *Proc. Natl. Acad. Sci. USA*, 1991, 88, 11510; Geyse *Proc. Natl. Acad. Sci. USA*, 1984, 81, 3998; Houghten *Proc. Natl. Acad. Sci. USA*, 1985, 82, 5131; Fodor *Science* 1991, 251, 767. We are not aware of effective methods to generate diverse mixtures of oligosaccharides and other glycoconjugates for screening purposes.

2.2. Anthracyclines

Ciclamycin 0 (1, below), an anthracycline antibiotic isolated from *Streptomyces capoamus*, possesses high inhibitory in vitro activity against experimental tumors. This drug is comprised of the aglycone ε-pyrromycinone and a trisaccharide. See, Bieber et al. *J. Antibiot.* 1987, 40, 1335. The trisaccharide contains two repeating units of 2-deoxy-L-fucose (A, B) and one unit of the keto sugar (C), L-cinerulose. All the sugars are connected to each other through a 1–4 axial linkage.

Although ciclamycin was discovered almost thirty years ago, little is understood about its function because insufficient quantities are available from natural sources. Consequently, the best way to obtain ciclamycin in large quantites, and the only way to obtain its analogs, is through chemical synthesis.

3

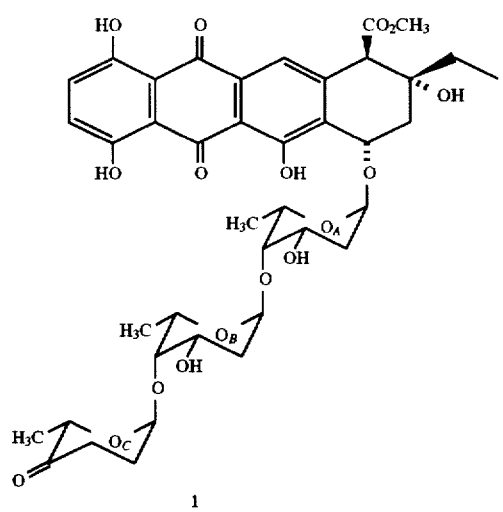

1

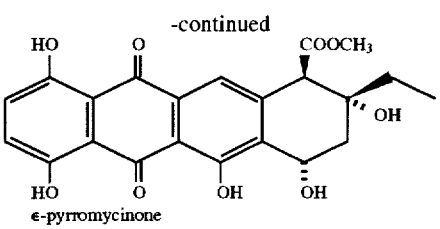

ε-pyrromycinone

A common feature of all anthracycline antibiotics is an oligosaccharide residue attached to the C-7 hydroxyl group of the aglycone. The sugar residue at this position can be a mono, di or trisaccharide. The most frequently encountered sugars include daunosamine, rhodosamine, 2-deoxy-L-fucose and L-cinerulose.

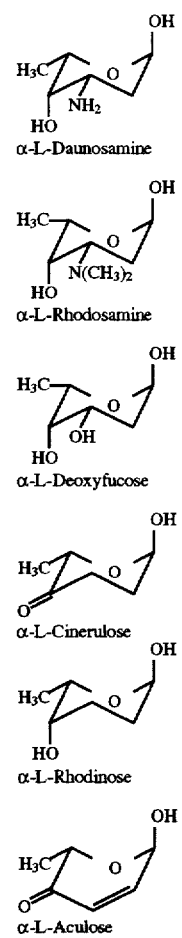

The aglycone of ciclamycin, ε-pyrromycinone, can be obtained by deglycosylation of other readily available antibiotics, such as marcellomycin, musettamycin and cinerubin. Efficient strategies exist in the literature for coupling the trisaccharide to the aglycone. See, for example, Kolar et al. *Carbohydr. Res.* 1990, 208, 111. However, methods for the construction of the trisaccharide suffer from limitations of overall ease and efficiency.

Anthracycline antibiotics occur as intermediates in the metabolism of several Streptomyces species. They are potent chemotherapeutic drugs that have been used extensively in the treatment of various solid tumors and leukemias. See, Arcamone, F. *Doxorubicin Anticancer Antibiotics*; Academic Press: New York, 1981. The aglycone of all anthracyclines consists of a tricyclic quininoid system with a functionalized cyclohexane moiety. Various substitution patterns frequently encountered among the aglycones are outlined, below.

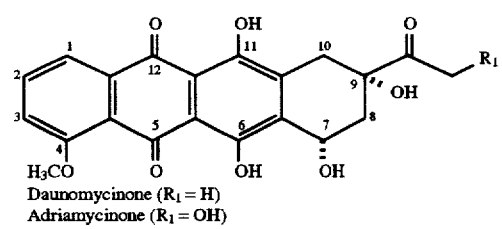

Daunomycinone ($R_1$ = H)
Adriamycinone ($R_1$ = OH)

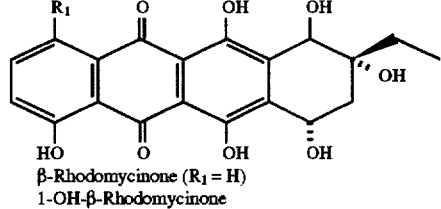

β-Rhodomycinone ($R_1$ = H)
1-OH-β-Rhodomycinone

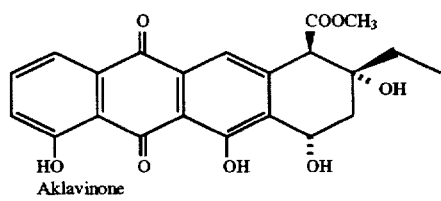

Aklavinone

On the basis of several studies conducted on the anthracycline antibiotics daunomycin, adriamycin, and aclacinomycin, it has become increasingly clear that the oligosaccharide components of these natural DNA binders play an important role in DNA binding and recognition. See, Bieber et al, supra. However, little is known about the actual function of the sugars, in part because it is difficult to selectively modify these drugs. The first chemical synthesis of ciclamycin 0 was accomplished by S. J. Danishefsky and coworkers. See, Suzuki et al. *J. Am. Chem. Soc.* 1990, 112, 8895.

2.2.1. Synthesis of 2-Deoxy Oligosaccharides

Complex glycoconjugates like anthracyclines and aureolic acids are of considerable scientific and pharmaceutical interest and have been applied extensively in cancer chemotherapy. A common structural feature in these compounds is the presence of 2-deoxy oligosaccharides. Indeed, several types of alpha- and beta-2-deoxy glycosides are frequently found in naturally occurring bioactive molecules. In addition to the aureolic acid antibiotics and anthracycline antibiotics, there can be found cardiac glycosides, avermectins, erythromycins, and the enediyne antibiotics. The efficient construction of these 2-deoxy glycosides, particularly 2-deoxy-β-glycosides, has been a long-standing problem in carbohydrate chemistry. Controlling the β stereoselectivity in 2-deoxy sugars is difficult because there can be no stereo-directing anchimeric assistance from the C-2 position.

In general, the specific therapeutic effect of these drugs is thought to be caused by the aglycone, while the sugars are thought to be responsible for regulating the pharmacokinetics. It is hoped that by modifying the carbohydrate moiety, it is possible to increase the efficacy and also decrease the cytotoxicity of these drugs.

The development of sugar analogs requires good synthetic methods for the construction of 2-deoxy oligosaccharides. Unfortunately, glycosylation methods available for synthesis of 2-deoxy oligosaccharides are generally unsatisfactory. Since 2-deoxy glycosyl donors lack a substituent at the C-2 position, they are unstable. They decompose rapidly in most glycosylation reactions, thereby resulting in poor yields of glycosides.

In fact, one of the better existing methods for constructing 2-deoxy oligosaccharides, the glycal method, circumvents this problem by not actually using 2-deoxy glycosyl donors directly. This procedure, which is one of the most widely used glycosylation methods for constructing 2-deoxy glycosides, involves a two-step process. In the first step, a 1,2-anhydro sugar (glycal) is treated with a suitable electrophile, $E^+$, to form a 1,2-onium intermediate. Nucleophilic attack from the opposite side affords the glycoside, with 1,2-trans-configured bonds. In the second step, the substituent at C-2 is removed to form the desired 2-deoxy glycoside.

2.3. Solution Methods for Obtaining Oligosaccharides

There are currently two general ways to obtain oligosaccharides. The first is by isolation from natural sources. This approach is limited to naturally occurring oligosaccharides that are produced in large quantities. The second way is through enzymatic or chemical synthesis. The variety of oligosaccharides available through enzymatic synthesis is limited because the enzymes used can only accept certain substrates. Chemical synthesis is more flexible than enzymatic synthesis and has the potential to produce an enormous variety of oligosaccharides. The problem with chemical synthesis has been that it is extremely expensive in terms of time and labor. This problem is a consequence of the way in which the chemical synthesis of oligosaccharides has been carried out to date.

Oligosaccharides are formed from monosaccharides connected by glycosidic linkages. In a typical chemical synthesis of an oligosaccharide, a fully protected glycosyl donor is activated and allowed to react with a glycosyl acceptor (typically another monosaccharide having an unprotected hydroxyl group) in solution. The glycosylation reaction itself can take anywhere from a few minutes to days, depending on the method used. The coupled product is then purified and chemically modified to transform it into a glycosyl donor. The chemical modification may involve several steps, each single step requiring a subsequent purification. (A "single step" is defined as a chemical transformation or set of transformations carried out in a "single" reaction vessel without the need for intermediate isolation or purification steps.) Each purification is time consuming and can result in significant losses of material. The new glycosyl donor, a disaccharide, is then coupled to another glycosyl acceptor. The product is then isolated and chemically modified as before. It is not unusual for the synthesis of a trisaccharide to require ten or more steps from the component monosaccharides. In one recent example, the fully protected trisaccharide side chain of an antitumor antibiotic called ciclamycin 0 was synthesized in 14 steps with a 9% yield based on the component monosaccharides. See, Suzuki et al, supra. Thus, the time and expense involved in the synthesis of oligosaccharides has been a serious obstacle to the development of carbohydrate drugs and other biomedical products.

One way to increase the speed and efficiency of oligosaccharide synthesis is to develop methods that permit the construction of multiple glycosidic linkages in a single step. Before the present discovery, the applicants are unaware of a one-step method which involves the regioselective formation of multiple glycosidic bonds and which provides a rapid, efficient and high yield process for the production of oligosaccharides.

2.4. Solid-Phase Synthesis of Oligosaccharides

Besides reducing the number of steps involved in the synthesis of oligosaccharides, one can also increase the speed and efficiency of a synthetic process by eliminating the need for isolation and purification. Theoretically, elimination of the need for isolation and purification could be achieved by developing a solid-phase process for the synthesize of oligosaccharides.

Due to the magnitude of the potential advantages of solid-phase synthesis, there have been previous attempts to synthesize oligosaccharides on a solid phase. Solid-phase methods for synthesis make isolation and purification unnecessary because excess reagents and decomposition products can simply be washed away from the resin-bound product. This advantage translates into an enormous savings in terms of time, labor, and yield. (The advantages of solid-phase methods over solution methods for the synthesis of peptides and nucleic acids have been amply demonstrated. These advantages would, of course, extend to a solid-phase synthesis of oligosaccharides. For the solid-phase synthesis of peptides, see, for example, Barany, G. and Merrifield, R. B. 1980, in *The Peptides*, Gross, E. and Meienhofer, J. Eds., Academic Press, New York, Vol 2, pp. 1–284.)

As far back as 1971, Frechet and Schuerch outlined the requirements for solid-phase oligosaccharide synthesis. See, Frechet and Schuerch *J. Am. Chem. Soc.* 1971, 93, 492. First, the resin must be compatible with the reaction conditions. Second, the solid support must contain appropriate functionality to provide a link to the glycosidic center (or elsewhere), which link is inert to the reaction conditions but can be easily cleaved to remove the oligosaccharide upon completion of the synthesis. Third, appropriate protecting group schemes must be worked out so that particular hydroxyls can be selectively unmasked for the next coupling reaction. The other hydroxyls should be protected by "permanent" blocking groups to be removed at the end of the synthesis. Fourth, the glycosylation reactions should be efficient, mild, and go to completion to avoid failure sequences. Fifth, the stereochemistry of the anomeric centers must be maintained during the coupling cycles and should be predictable based on the results obtained in solution for any given donor/acceptor pair. Sixth, cleavage of the permanent blocking groups and the link to the polymer must leave the oligosaccharide intact.

Unfortunately, although it has been generally accepted that solid-phase oligosaccharide synthesis is a desirable goal, and although Frechet and Schuerch (as well as others) were able to outline a strategy for solid-phase oligosaccharide synthesis, no one, before the present discovery, had been able to implement such a strategy. In previous attempts to synthesize oligosaccharides on insoluble resins, the coupling yields were low and the stereochemical control was inadequate, particularly for the construction of β-glycosidic linkages (i.e., 1,2-trans glycosidic linkages in which the glycosidic bond at the anomeric position of the sugar is trans to the bond bearing the sugar substituent at C-2).

These problems have been attributed to the fact that reaction kinetics on the solid phase are slower than they are in solution. See, Eby and Schuerch, *Carbohydr. Res.* 1975, 39, 151. The consequence of such unfavorable kinetics is that most glycosylation reactions, which may work reasonably well in solution, simply do not work well on a solid phase both in terms of stereochemical control and yield. Thus, for example, Frechet and Schuerch found that two glycosylation reactions, which both involve the displacement of an anomeric halide in the presence of a catalyst, gave predominantly the β-anomer (i.e., the 1,2-trans product) in solution but gave mixtures on the solid phase. Frechet and Schuerch concluded that it would be necessary to use neighboring group participation to form β-glycosidic linkages on the solid phase.

Again, however, it has been found that neighboring participating groups (NPGs) frequently deactivate glycosyl donors to the point that existing glycosylation methods could not be adapted to the solid phase. Frequently, glycosyl donors would decompose in the resin mixture before glycosylation can take place. See, Eby and Schuerch, supra. In some instances the resin has also been known to decompose due to the harshness of the conditions required for glycosylation. Furthermore, for many ester-type NPGs, there is a significant problem with acyl transfer from the glycosyl donors to the free glycosyl acceptors on the resin. This side reaction caps the resin and prevents further reaction.

Frechet has reviewed the problems encountered in trying to implement a strategy for solid-phase oligosaccharide synthesis. See, Frechet, *Polymer-supported Reactions in Organic Synthesis*, p. 407, P. Hodge and D. C. Sherrington, Eds., John Wiley & Sons, 1980. He has concluded that solid-phase oligosaccharide synthesis is not yet competitive with solution synthesis "due mainly to the lack of suitable glycosylation reactions."

There have been some efforts to overcome the unfavorable reaction kinetics associated with solid-phase reactions by using soluble resins. In the best example to date Douglas et al. used a soluble polyethylene glycol resin with a succinic acid linker and achieved 85-95% coupling yields using a glycosylation method known for over 80 years (the Koenigs-Knorr reaction) with excellent control of anomeric stereochemistry. See, Douglas et al. *J. Am. Chem. Soc.* 1991, 113, 5095. Soluble resins may have advantages for some glycosylation reactions because they offer a more "solution-like" environment. However, step-wise synthesis on soluble polymers requires that the intermediate be precipitated after each step and crystallized before another sugar residue can be coupled.

Moreover, several additions of the same glycosylating reagent are typically required to push a reaction to completion. In the above case, for example, Douglas et al. had to repeat the same coupling reaction five times to achieve a high yield. Each repetition requires a precipitation step to wash the reagents away. Product may be lost with each precipitation step. In addition, repeated precipitations make the process very time-consuming. Thus, the soluble resin approach to oligosaccharide synthesis fails to provide all the potential advantages associated with solid phase synthesis using insoluble resins.

A new method for glycosylation involving anomeric sugar sulfoxides was reported by Kahne and co-workers. See, Kahne et al. *J. Am. Chem. Soc.* 1989, 111, 6881. The anomeric sugar sulfoxides were activated with equimolar amounts of triflic anhydride in the presence of a hindered base. The triflic anhydride-activated glycosyl donors proved to be quite reactive in solution and could be used to glycosylate extremely unreactive substrates under mild conditions. However, this report was limited to solution reactions, and there was no suggestion that solid-phase reactions could be carried out with any degree of utility.

Thus, the state of the art underscores the prevailing and unfullfilled need for a glycosylation method which provides for the rapid, efficient, and high yield synthesis of oligosaccharides. Moreover, an efficient synthesis of oligosaccharides on the solid phase has not been demonstrated which provides all the previously mentioned advantages of solid-phase methods.

3. SUMMARY OF THE INVENTION

The present invention provides methods for constructing multiple glycosidic linkages in solution using anomeric sugar sulfoxides as glycosyl donors and for constructing sequential glycosidic linkages on the solid phase, with control over the stereochemical configuration of the anomeric bond. Thus, depending upon the selected conditions and starting materials, α- or β-anomers can be produced on the solid phase using anomeric sugar sulfoxides as glycosyl donors. The methods of the present invention may be applied to the preparation of specific oligosaccharides or glycoconjugates or to the preparation of mixtures of various oligosaccharides or glycoconjugates for the creation of glycosidic libraries that can subsequently be screened to detect compounds having a desired biological activity.

The present invention also relates to the discovery that the activation of anomeric sulfoxides with catalytic quantities of an activating agent provides very good yields of condensation product under very mild conditions. Preferably, the activating agent is a strong organic acid, such as trifluoromethanesulfonic or "triflic" acid (TfOH), p-toluenesulfonic acid (TsOH) or methanesulfonic acid (MsOH), most preferably, TfOH. In particular, it has been found that for the construction of 2-deoxy glycosides, the catalytic glycosylation procedure described herein is considered the method of choice. A preferred embodiment of this aspect of the invention, involving the synthesis of 2-deoxy glycosides via the triflic acid-catalyzed glycosylation, is described in greater detail, below.

Other objects of the present invention will be apparent to one of ordinary skill on consideration of the present disclosure.

4. BRIEF DESCRIPTION OF THE FIGURES

FIGS. 5A and 5B illustrate an apparatus used to carry out solid phase oligosaccharide synthesis.

FIG. 12A is a $^1$H NMR spectrum of trisaccharide 5 of FIG. 1.

FIG. 12B shows the structure of trisaccharide 5.

Figures 13A, 13B:
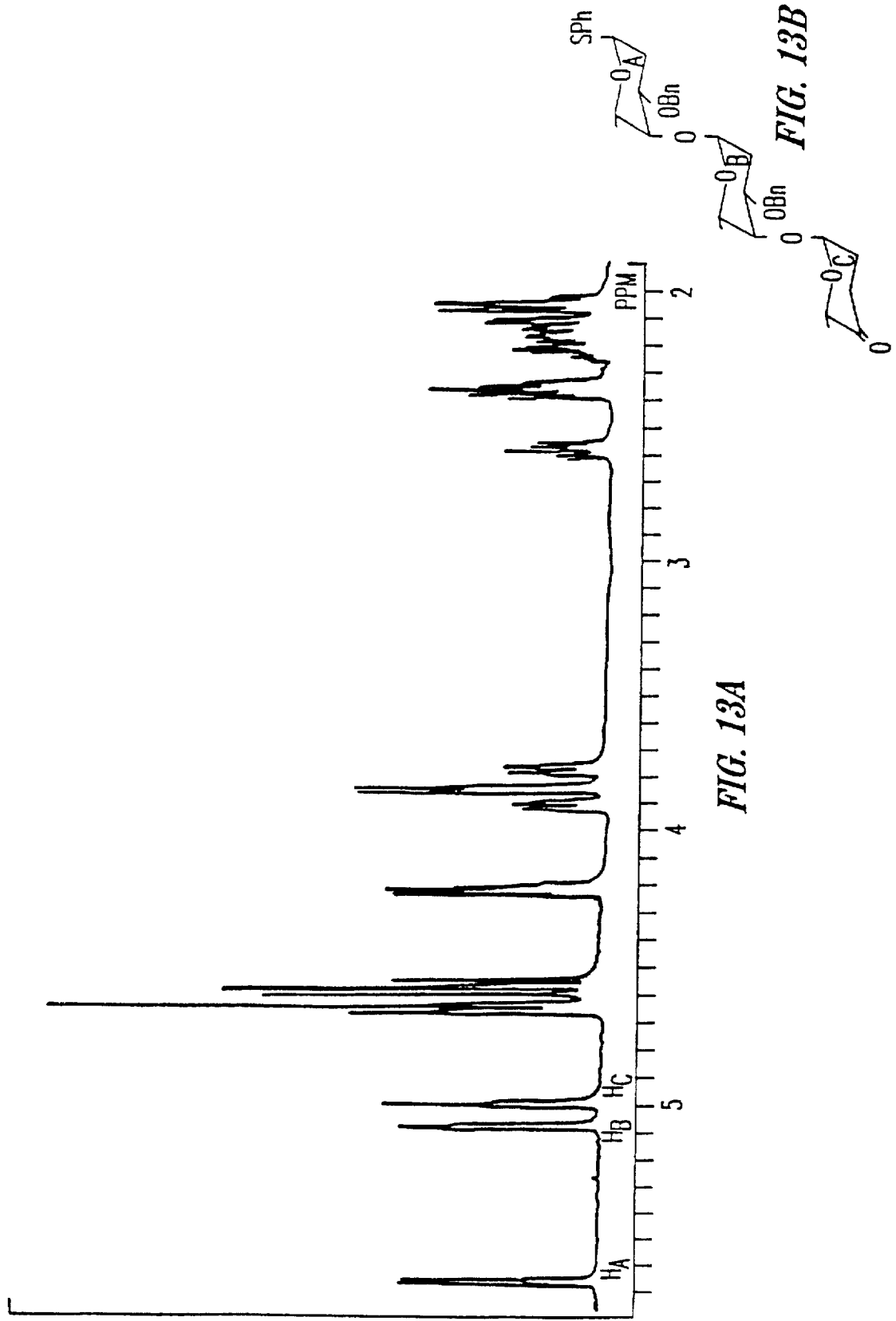

FIG. 13A presents an expanded region of the $^1$H NMR spectrum of 5, in which the anomeric protons of the trisaccharide are labeled.

FIG. 13B shows the structure of trisaccharide 5.

Figure 1:
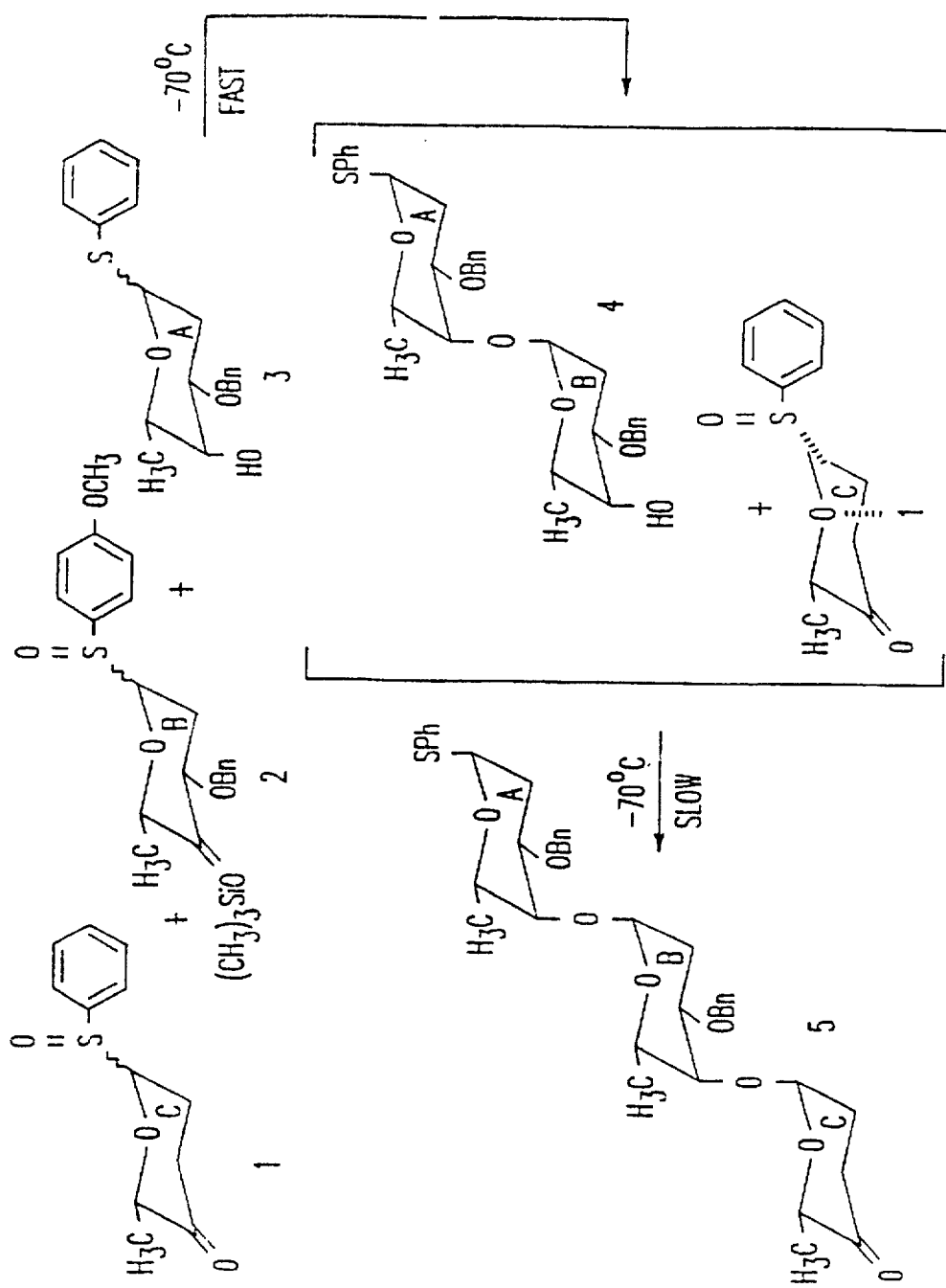
FIG. 1 illustrates a method of synthesizing the protected trisaccharide of ciclamycin 0 in one step from the component monosaccharides.
Figures 14A, 14B:
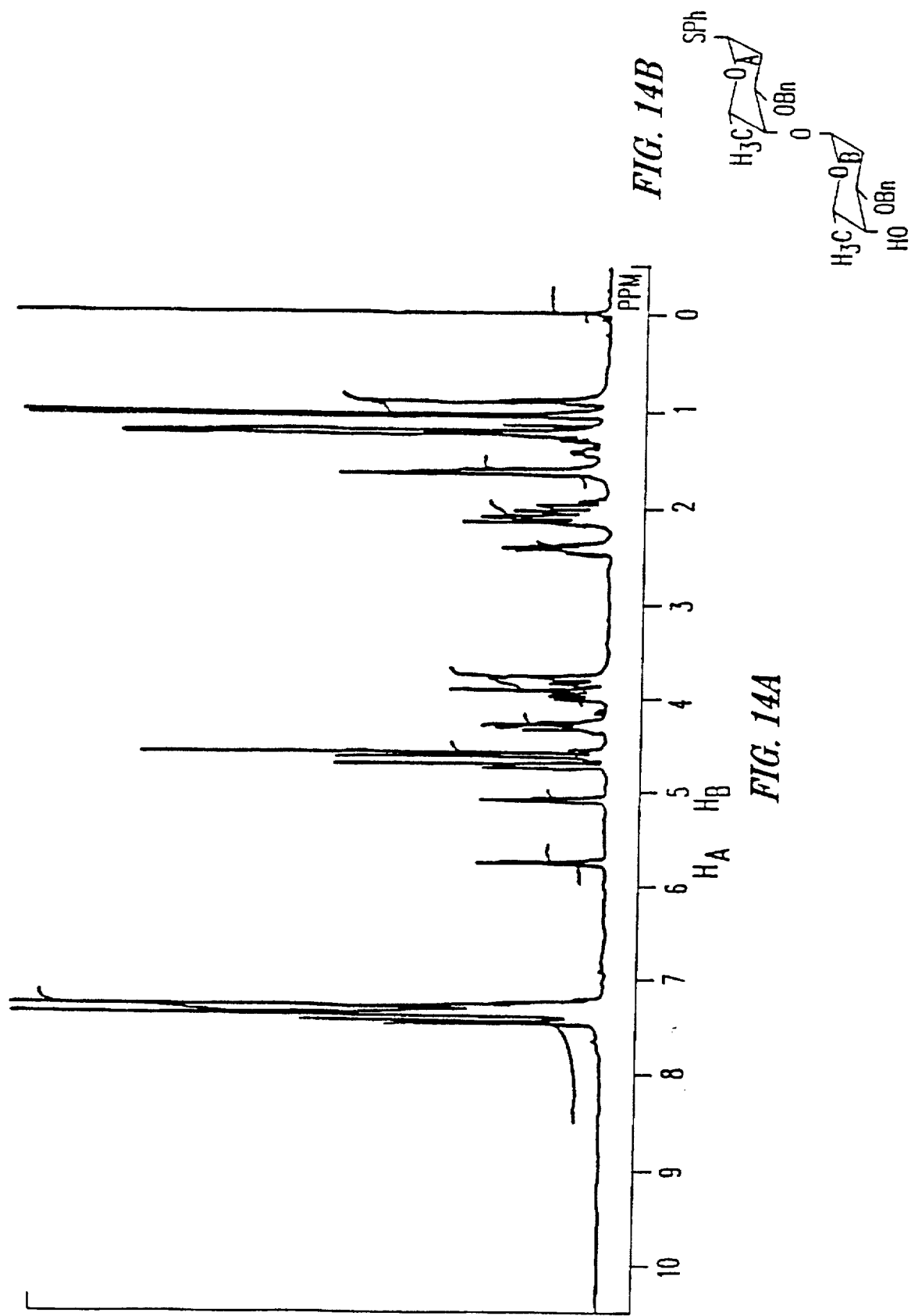

FIG. 14A is a $^1$H NMR spectrum of disaccharide 4 of FIG. 1.

FIG. 14B shows the structure of disaccharide 4.

Figure 15:
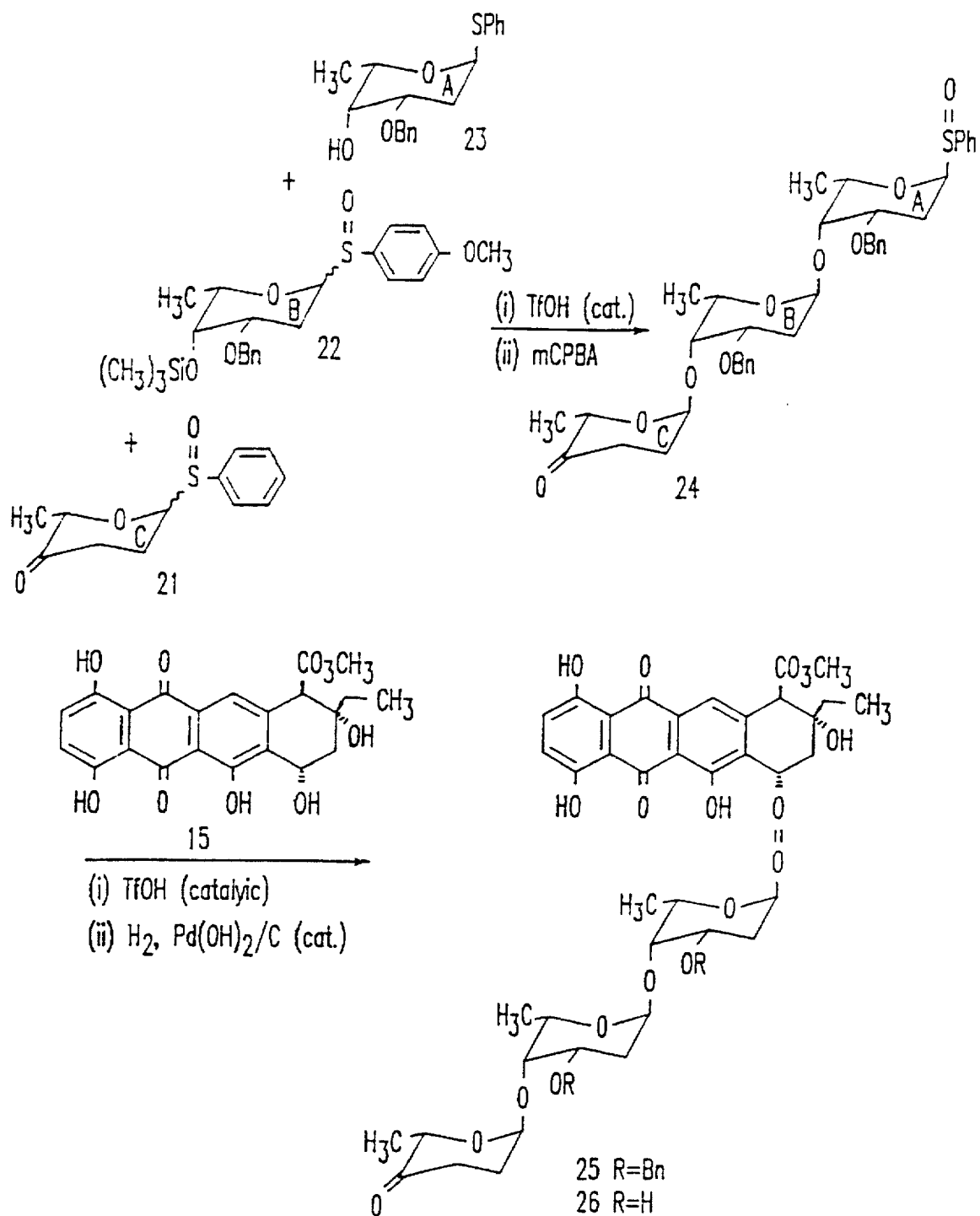

FIG. 15 represents a scheme for the synthesis of ciclamycin 0.

Figure 16A:
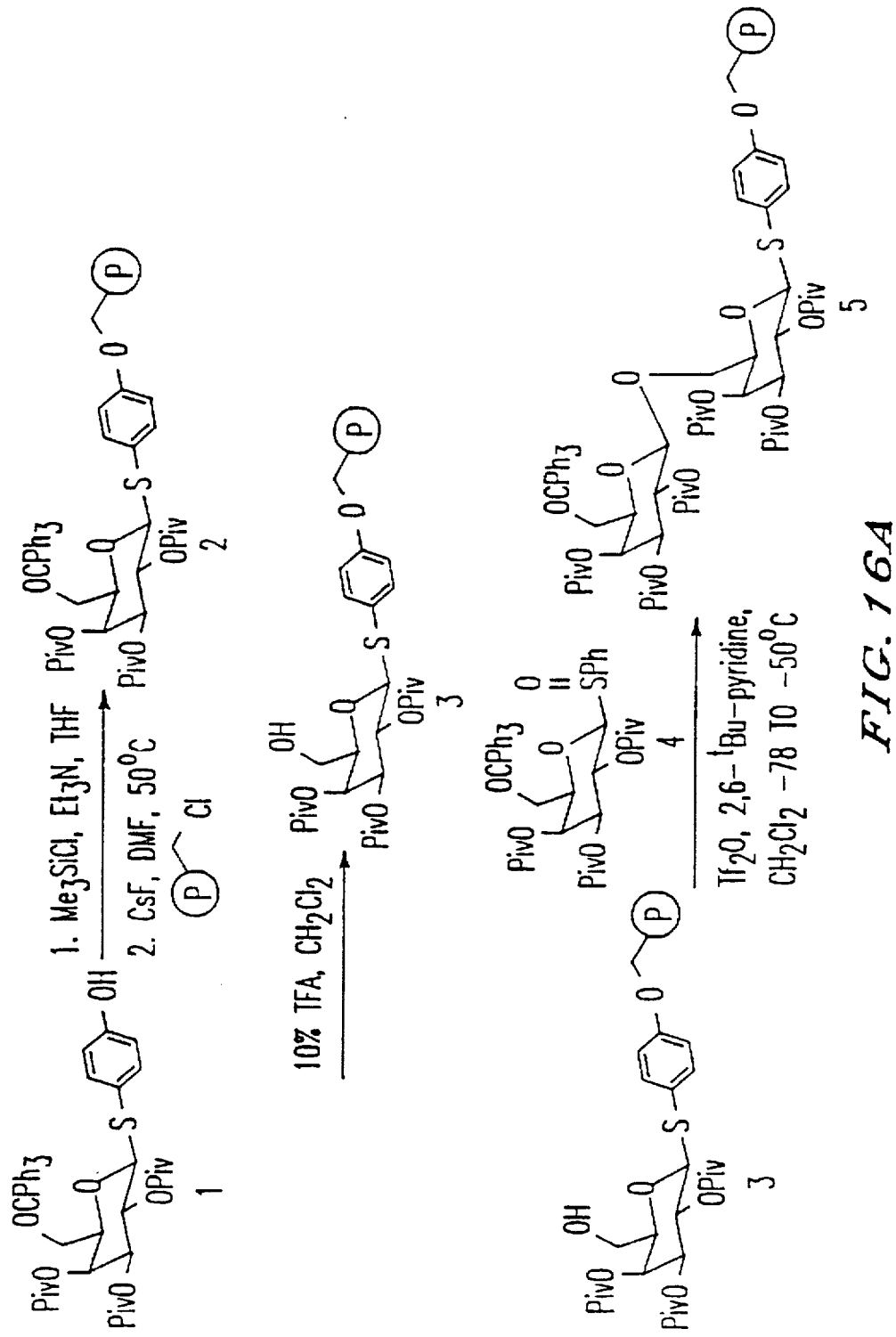
Figure 16B:
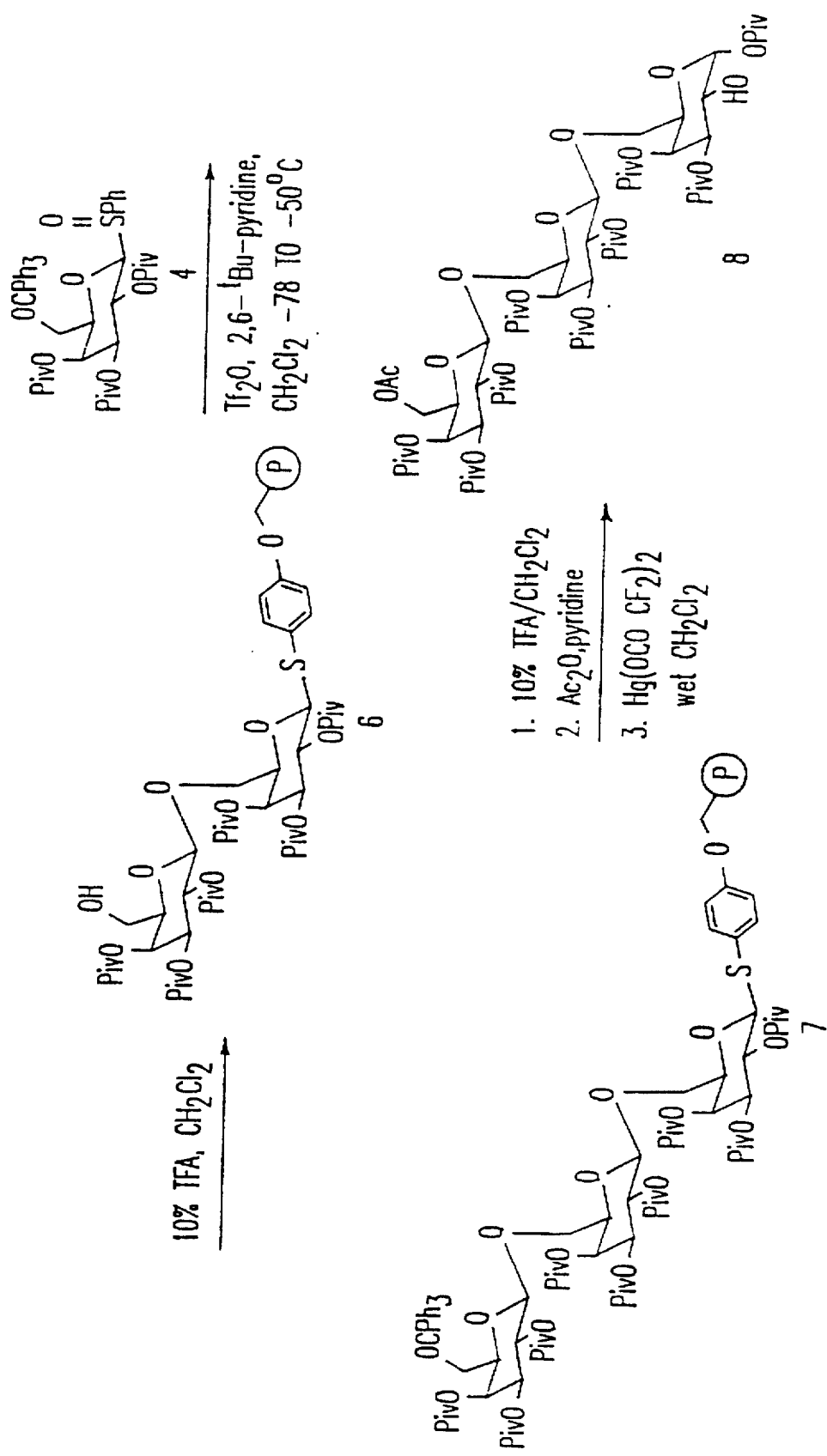

FIGS. 16A and 16B represent a scheme for the synthesis of a trisaccharide.

Figure 17A:
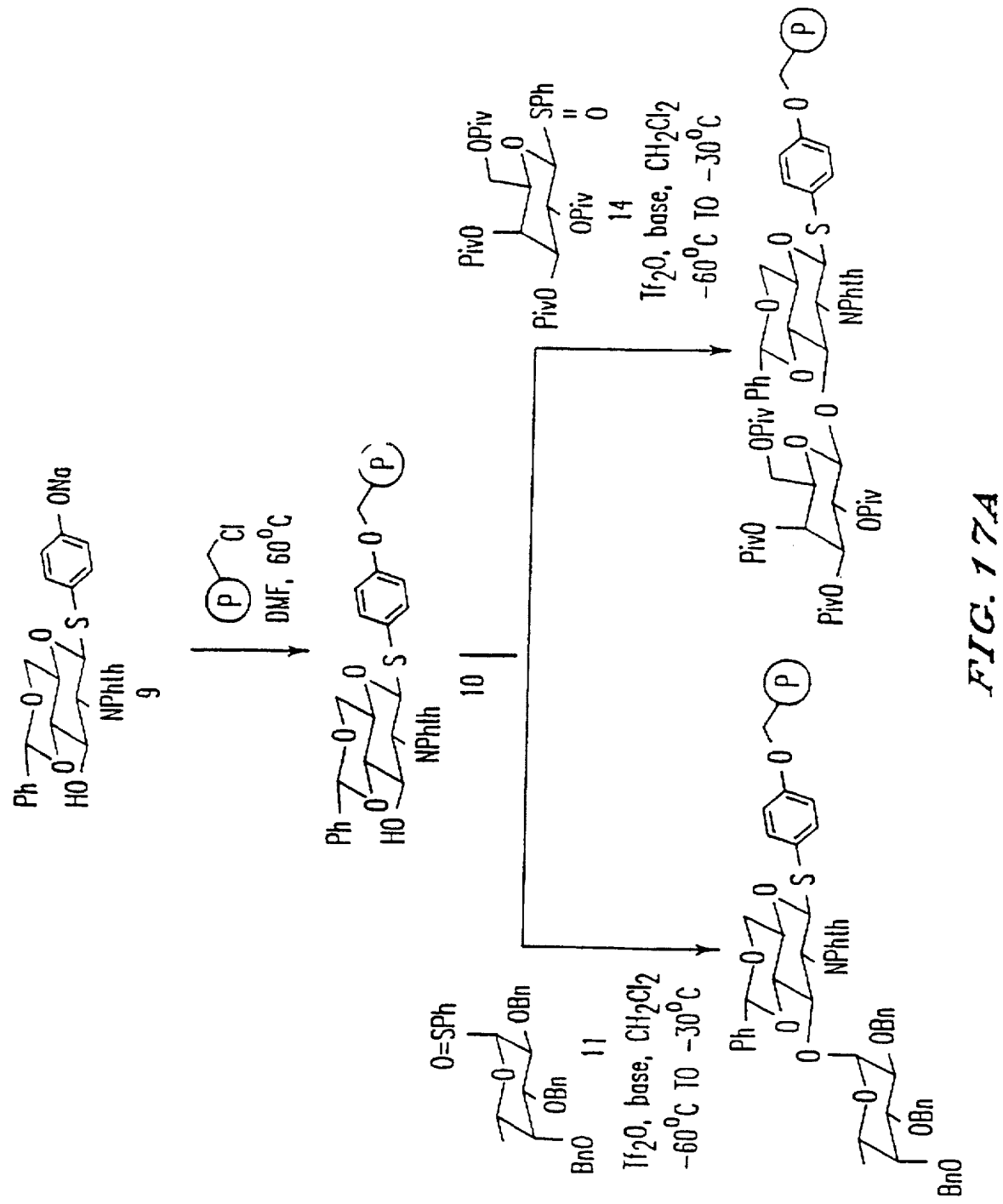
Figure 17B:
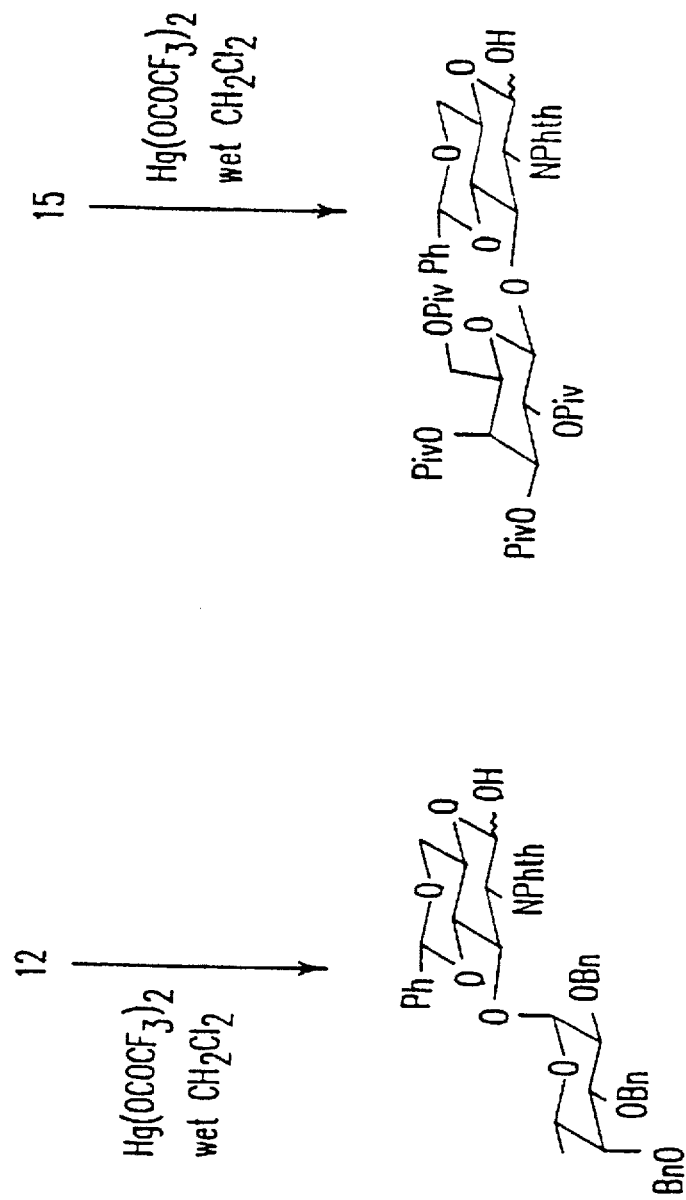

FIGS. 17A and 17B represent a scheme for the synthesis of selected disaccharides.

5. DETAILED DESCRIPTION OF THE INVENTION

What follows is a detailed description of the preferred embodiments of the present invention.

5.1. Definitions

Activating agent: A chemical agent that on addition to a glycosyl sulfoxide reacts with the anomeric sulfoxide group, thus rendering the anomeric carbon susceptible to nucleophilic attack. In the case of bifunctional sugars or glycosidic residues, the activating agent is also able to deprotect a blocked nucleophilic group under the same conditions used to activate the anomeric sulfoxide group.

Acid scavenger: A chemical agent such as any base that sequesters protons, thereby minimizing side reactions that are promoted by acidic conditions.

Sulfenic acid scavenger: A chemical agent such as methyl propiolate that specifically sequesters sulfenic acid, typically resulting in the formation of an unreactive monophenyl sulfoxide. In the absence of a sulfenic acid scavenger, sulfenic acid reacts with itself to form diphenyl disulfide monosulfoxide and water. Water interferes with the glycosylation reaction.

Bifunctional: The characteristic of a sugar or glycosidic residue to be able to function on activation both as a glycosyl donor and a glycosyl acceptor under the conditions of the single-step process of the present invention.

Biological activity: Any activity displayed by a compound or molecule which has potential physiologic, pharmacologic, diagnostic, or therapeutic applications.

Carbohydrate receptor: Any molecule that binds any carbohydrate. Typically the molecule is a macromolecule such as a protein or DNA.

Glycoconjugate: Any compound or molecule that is covalently bound to a glycosidic residue.

Glycoside: Any sugar containing at least one pentose or hexose residue in which the anomeric carbon bears a non-hydrogen substituent. Typically, the non-hydrogen substituent is a heteroatom, such as nitrogen, oxygen, phosphorus, silicon or sulfur.

Glycosyl acceptor: Any compound that contains at least one nucleophilic group which, under the conditions of the single-step process of the present invention, is able to form a covalent bond with the anomeric carbon of a glycosyl donor. As referred to herein, a glycosyl acceptor may be any sugar or glycoconjugate that contains unprotected hydroxyl, amino, or mercapto groups or such groups that are blocked by protecting groups that can be removed in situ, i.e., under the conditions of the single-step process of the present invention.

Glycosyl donor: A sugar or glycosidic residue that bears a sulfoxide group at the anomeric carbon, which group on activation renders the anomeric carbon susceptible to attack by the nucleophilic group of a glycosyl acceptor to form the glycosidic linkage.

Glycosidic libraries: A mixture of oligosaccharides of varying sequences which can be subjected to a screening procedure to identify compounds or molecules that exhibit biological activity. Such libraries may also include various glycoconjugates.

Monofunctional glycosyl acceptor: A glycosyl acceptor as in the definition above, with the additional provision that the capacity to act as a glycosyl donor at the same time (i.e., under the conditions of the single step process of the present invention) is specifically excluded.

Monofunctional glycosyl donor: A glycosyl donor as in the definition above, with the additional provision that the capacity to act as a glycosyl acceptor at the same time (i.e., under the conditions of the single step process of the present invention) is specifically excluded.

Monofunctional glycosyl unit: A sugar that is either a glycosyl acceptor or a glycosyl donor but does not have the capacity to function as both upon activation under the conditions of the single step process of the present invention.

Oligosaccharides: A glycosidic residue having three or more monosaccharide units joined by glycosidic linkages.

Potential glycosyl acceptor: Any compound containing at least one nucleophilic group which is potentially able to form a covalent bond with the anomeric carbon of a glycosyl donor.

Single step reaction: A single step reaction is defined as a chemical transformation or set of transformations carried out in a "single" reaction vessel without the need for intermediate isolation or purification steps (i.e., a one-step or one-pot reaction).

Temporal protecting group: A blocking or protecting group that can be removed in situ, preferably, but not necessarily, under the same conditions used to activate an anomeric sulfoxide group.

5.2. General Methods

The following general methods have been divided into two main categories: the first concerns solution reactions involving the formation of multiple glycosidic bonds and the second relates to the synthesis of oligosaccharides in which the growing oligomer is bound to a solid support.

5.3. Formation Of Multiple Glycosidic Linkages In Solution

One or more glycosyl donors having alkyl or aryl sulfoxides at the anomeric position and one or more glycosyl acceptors having one or more free hydroxyls and/or other nucleophilic groups (e.g., amines) and/or silyl ether protected hydroxyls are combined in a reaction vessel. The resulting mixture may include both monofunctional glycosyl donors and glycosyl acceptors as well as bifunctional glycosyl units, i.e., saccharides that can function simultaneously as glycosyl donors and acceptors. However, in order to form more than one glycosidic linkage (i.e., to produce a trisaccharide or longer product), at least one of the reactants must be a bifunctional glycosyl unit.

The glycosyl acceptors and donors may be blocked by a suitable protecting group, including, but not limited to, ether, ester, acetamido, or thioester protecting groups, at one or more positions. However, it is understood that an ester (or acetamido or thioester) protecting group at C-2 of a glycosyl donor will influence the stereochemical outcome of glycosylation, resulting in a 1,2-trans glycosidic bond.

The mixture of glycosyl donors and acceptors is dissolved under anhydrous conditions in a non-nucleophilic solvent, including, but not limited to, toluene, ether, tetrahydrofuran (THF), methylene chloride, chloroform, propionitrile, or mixtures thereof. It has been found that the choice of solvent influences the stereochemical outcome of glycosylation for reactions in which neighboring group participation is not involved. In general, for a given donor/acceptor pair, the use of a non-polar solvent, such as toluene, results in the formation of a higher percentage of alpha isomer, while the use of a more polar solvent, such as propionitrile, results in formation of a higher percentage of the beta anomer.

The reaction is initiated by the addition of an effective amount of an activating agent. In a particular embodiment of the present invention, 0.5 equiv. of triflic anhydride, plus 1.5 equiv. base (as an acid scavenger), are added to the reaction mixture. (Equivalents are relative to glycosyl sulfoxide.) A catalytic amount of triflic acid (e.g., <0.05 equiv.) can also be used, preferably along with excess sulfenic acid scavenger (e.g., ca. 20 equiv. of methyl propiolate). It has been found that catalytic triflic acid is preferred when the reaction mixture contains 2-deoxy glycosyl donors or when one of the glycosyl acceptors in the reaction is a silyl ether. On the other hand, triflic anhydride is preferred when maximum reactivity of the glycosyl donors is important. However, it should be noted that the moderately basic conditions that obtain with the use of triflic anhydride are not effective to deprotect certain silyl ethers (e.g., t-butylsilyl ethers). Moreover, although the use of triflic anhydride plus 2,6-ditert-butyl-4-methyl pyridine will result in the in situ deprotection of trimethylsilyl ethers, the use of triflic anhydride plus a stronger base (such as Hunig's base) will not. Thus, both activating agents can be used in reactions involving a bifunctional glycosyl unit containing a silyl ether protected hydroxyl, although triflic anhydride only works under a specific set of conditions (choice of base, choice of silyl protecting group). Otherwise, the two activation methods are usually interchangeable.

The methyl propiolate or other sulfenic acid scavenger and/or activated molecular sieves may be added to the reaction either before or just after the addition of activating agent. Sulfenic acid scavengers significantly improve the yield of glycosylation when catalytic triflic acid is used as the activating agent.

The reaction is normally carried out at low temperature (preferably in the range of about $-78°$ C. to as low as bout $-100°$ C.) but may be allowed to proceed at higher temperatures, in some cases as warm as room temperature.

The reaction is quenched by the addition of aqueous bicarbonate and extracted. The reaction mixture may then be subjected to a purification procedure and/or the product(s) deprotected if necessary. The procedure may be used to construct specific oligosaccharides or mixtures of various oligosaccharides or other glycoconjugates for screening for biological activity.

In particular embodiments of the present invention, it has been discovered that the reactivity of different glycosyl donors may be modulated by manipulating the chemical structure and electronic nature of the anomeric sulfoxide. Such manipulation is due, in part, to the finding that the rate-limiting step in the glycosylation reaction is activation of the sulfoxide by the action of the activating agent. It was subsequently shown that the reactivity of the glycosyl sulfoxides can be influenced by manipulating the nucleophilicity of the sulfoxide oxygen.

Generally, the more nucleophilic the sulfoxide oxygen, the faster the glycosylation reaction. Thus, electron-donating substituents on the R' group attached to the sulfoxide increase the nucleophilicity of the sulfoxide oxygen and speed up the rate of the reaction. By contrast, electron-withdrawing groups decrease the nucleophilicity of the sulfoxide oxygen and slow down the reaction. For example, perbenzylated glucosyl p-methoxyphenyl sulfoxide reacts faster than the corresponding unsubstituted phenyl sulfoxide, while perbenzylated glucosyl p-nitrophenyl sulfoxide reacts slower than the corresponding unsubstituted phenyl sulfoxide.

The ability to influence the nucleophilicity of different sulfoxides and hence to manipulate the reactivity of different glycosyl donors has been exploited in particular embodiments of the present invention. For example, this ability permits sequential glycosylations to take place in solution, as illustrated in FIG. 1.

In yet other embodiments of the present invention, multiple glycosidic linkages are formed in solution using silylated glycosyl acceptors. Silyl ethers are excellent glycosyl acceptors when catalytic triflic acid is the activating agent and trimethylsilyl ethers work well as glycosyl acceptors when triflic anhydride is the activating agent and 2,6-ditert-butyl-4-methyl-pyridine is the base. However, they must be unmasked in order to couple. (Hence the requirement for slightly acidic conditions in the glycosylation reaction when silyl ethers are used as glycosyl acceptors.) Because silyl ethers must be unmasked in order to couple, they react more slowly than unprotected alcohols. In this manner, it has been demonstrated that one can modulate the reactivity of two otherwise similar glycosyl acceptors by selective use of silyl protecting groups.

In selected embodiments of the present invention, the distribution of the length of the oligosaccharides or the glycosidic residues of the glycoconjugates produced can be influenced by varying the ratio of monofunctional glycosyl acceptors and monofunctional glycosyl donors to bifunctional glycosyl units in the reaction mixture. For example, it has been shown that higher ratios of monofunctional glycosyl acceptors to bifunctional glycosyl units in the reaction mixture lead to shorter length polymers. The total concentration of reactants also influences the length distribution. (See, Sections 6.6 and 6.8 and FIGS. 2 and 3, below.)

In particular embodiments of the present invention, it may be desirable to include only two or three different types of sugars in the reaction mixture and to manipulate the reactivity of the glycosyl donors and acceptors so that a specific oligosaccharide is produced. An example of this procedure is given in Sections 6.1. and 6.6. below.

Yet in other embodiments of the present invention, it may be desirable to include several different types of sugars in the reaction mixture in order to generate a chemically diverse mixture of oligosaccharides or glycoconjugate products for the creation of libraries that may be screened for biological activity. An example of such a method is illustrated in Section 6.6 and FIG. 3. below.

The chemical diversity can be influenced by manipulation of the number of different sugars included in the mixture. The chemical diversity will also be a function of the order in which different glycosyl donor/acceptor pairs react. The order in which different donor/acceptor pairs react will depend, in turn, on the relative reactivity of different donor/acceptor pairs. The relative reactivity of different/donor acceptor pairs can be manipulated in various ways, as already described above (e.g., by manipulating the structure of the sulfoxide groups used and by protecting some glycosyl acceptors with silyl ethers to slow down the rate at which they react).

Other factors that influence the relative reactivity of glycosyl donors and acceptors, such as the presence of electronegative protecting groups on the sugar rings or the presence of steric hindrance can also be exploited. See, e.g., Binkley *Modern Carbohydrate Chemistry*, Marcel Dekker, Inc: New York, 1988; also, Paulsen *Angew. Chem. Int. Ed. Engl.* 1982, 22, 156. Hence, potentially many factors can be taken into account in the implementation of the disclosed method of forming multiple glycosidic linkages to produce chemically diverse mixtures.

5.4. Catalytic Activation of Anomeric Sulfoxides

Elsewhere in this disclosure, the triflic anhydride activation of anomeric sulfoxides was described, and the mechanism of this glycosylation reaction discussed. Triflic anhydride reacts with the sulfoxide to form a trifloxy sulfonium salt that is extremely reactive.

In the presence of base, half an equivalent of triflic anhydride was sufficient to activate a full equivalent of sulfoxide. The phenyl trifluromethanesulfenate (PhSOTf) generated during the course of the reaction evidently activated the remaining 0.5 equivalent of the sugar sulfoxide (See, below). Indeed, others have used sulfonate esters to activate thioglycosides. For example, Ogawa et al. use phenyl selenium triflate to activate phenyl and alkyl thioglycosides. See, Ito and Ogawa *Tetrahedron Lett.* 1987, 28, 2723.

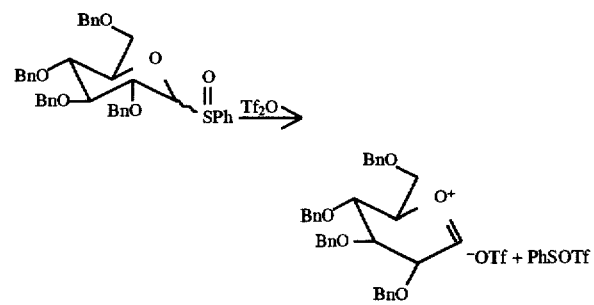

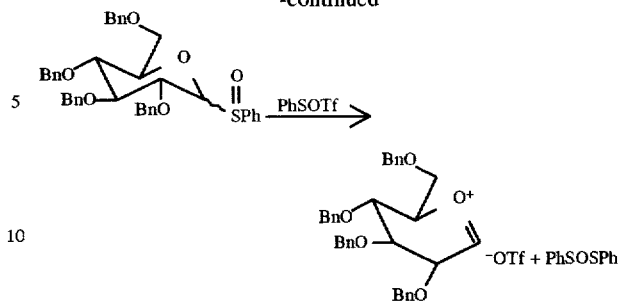

In the absence of base, however, less than 0.05 equivalents of triflic anhydride activated a full equivalent of sulfoxide. Because the trifloxy phenyl sulfonate (PhSOTf) and triflic anhydride combined did not amount to more than 0.1 equivalent, some other species generated in the reaction was activating the sulfoxide in a catalytic cycle. It was reasoned that the catalyst in question was triflic acid (TfOH). TFOH has been used by others to activate other glycosyl donors. See, e.g., most recently, Lonn *Glycoconjugate J.* 1987, 4, 117; Mootoo et al. *J. Am. Chem. Soc.* 1989, 111, 8540; Evans et al. *J. Am. Chem. Soc.* 1990, 112, 7001; and Veeneman et al. *Tetrahedron Lett.* 1990, 31, 1331. Furthermore, it was discovered that only catalytic amounts are typically required because the acid is regenerated in the reaction.

To determine whether TfOH can activate anomeric sulfoxides, the following experiment was conducted using perbenzylated glucose sulfoxide 1 as the glycosyl donor and the C-6 primary alcohol 2a as the glycosyl acceptor (See, scheme below).

The sulfoxide 1 (1.5 equivalents) was treated with triflic acid (0.05 equivalents) at −78° C. in methylene chloride. This step was followed by the addition of the nucleophile (1.0 equivalent) to the reaction. All of the sulfoxide was consumed to form product, indicating that triflic acid in catalytic amounts activates anomeric sulfoxides.

5.4.1. Mechanism

Although not wishing to be limited by theory, the following mechanistic interpretation is offered for the benefit of the interested reader. The stereochemical outcome for glycosylation using the catalytic triflic acid method was identical to that obtained from the stoichiometric triflic anhydride method. It was surmised that both reactions proceed via the same reactive intermediate, i.e., an oxonium ion or tight ion pair.

With the TFOH method, however, the yield for the desired disaccharide 3 was low. A significant amount of lactol, 4, and the 1,1-dimer, 5, were produced as by products (See, below). The nature of these byproducts indicated to the present applicant that water was present in the reaction. In particular, if an oxonium ion is trapped by water, a lactol will be formed. If the anomeric lactol then traps another oxonium ion, a 1,1-dimer of the glycosyl donor would be formed.

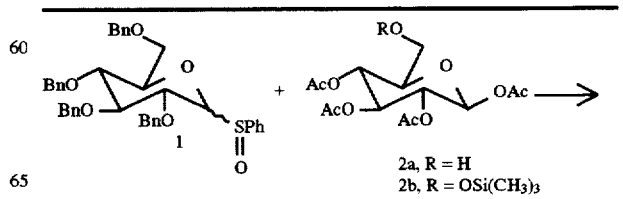

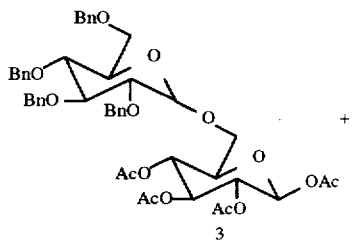

3

To prevent the formation of water, the glycosylations were conducted under scrupulously anhydrous conditions, using activated molecular sieves. Despite these precautions however, formation of byproducts, accounting for 40% of the mass balance, was observed. This last observation suggested that water was somehow being formed during the course of the reaction, possibly from the disproportionation of phenyl sulfenic acid.

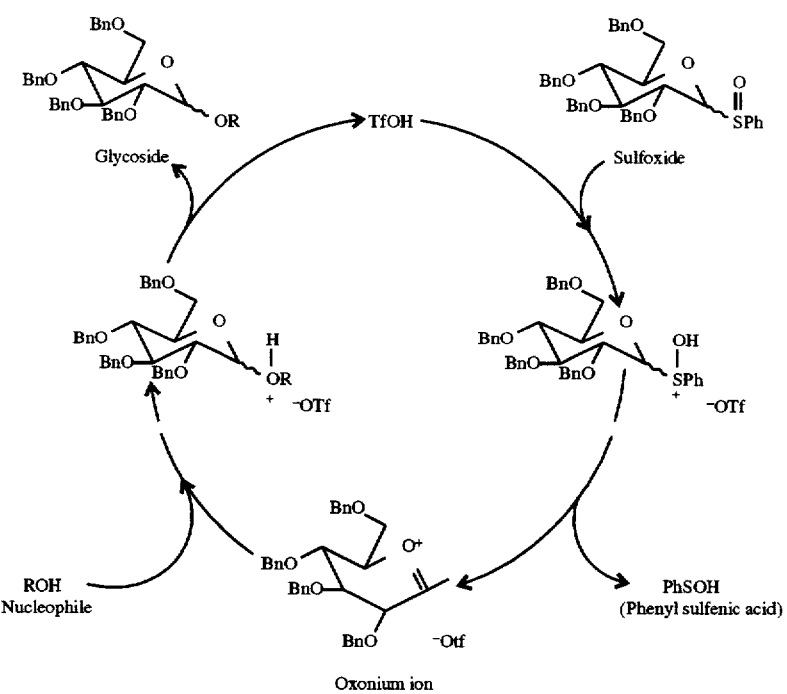

As illustrated in the scheme, above, the first step of the catalytic cycle is protonation of the sulfoxide to form a sulfonium salt. The sulfonium salt then ejects phenyl sulfenic acid (PhSOH) to form an oxonium ion or a tight ion pair. The nucleophile traps the oxonium ion, subsequently regenerating TfOH. In every catalytic cycle, one molecule of sulfoxide forms product and generates one molecule of phenyl sulfenic acid as byproduct.

Sulfenic acids are a class of organo sulfur compounds that have eluded isolation because of their instability. They have high reactivity as both electrophiles and nucleophiles. Sulfenic acids readily undergo disproportionation to thiosulfinate esters and water. The postulated mechanism for disproportionation, incorporating their dual electrophilic/nucleophilic character, is illustrated below.

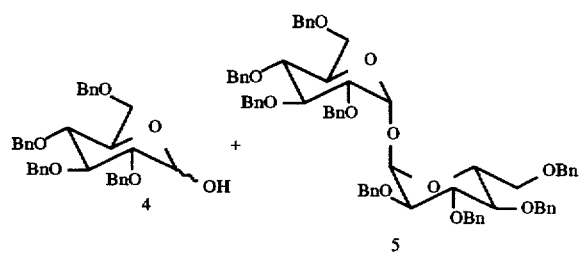

| | 1 | 2 | | 3 | 4 | 5 |
|---|---|---|---|---|---|---|
| A. | 1.5 eq | 1.0 eq | Tf₂O, base → | 55% | 25% | 9% |
| B. | 1.5 eq | 1.0 eq | TfOH → | 35% | 41% | 15% |
| C. | 1.5 eq | 1.0 eq | TfOH, HC≡CCOOMe → | 60% | 23% | 5% |

R=H with Tf₂O; R=Si(CH₃)₃ with TfOH

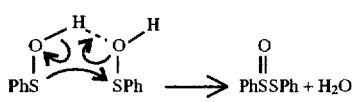

5.4.2. Addition of Scavengers for Sulfenic Acids

Sulfenic acids readily add to electron deficient alkenes and alkynes to form vinyl sulfoxides. Thus, it may be possible to trap these compounds with a sulfenic acid scavenger before they self condense. Examples of alkenes and alkynes frequently used to trap sulfenic acids include methyl propionate, methyl propiolate, styrene, and dimethyl dicarboxylate. The above compounds were screened as potential scavengers, and methyl propiolate was found to be the most effective.

In a typical reaction, 1 and 2 were allowed to react with TfOH in the presence of methyl propiolate (20 equivalents). The yield for the reaction improved from 35% (in the absence of methyl propiolate) to 45% (in the presence of methyl propiolate). Although the reaction yield improved, significant quantities of 4 and 5 were still produced. Hence, still further ways to prevent the disproportionation of sulfenic acid were sought.

5.4.3. Use of Silyl Ethers as Nucleophiles

It was reasoned that the use of silyl ether protected alcohols as nucleophiles could further minimize the buildup of water. The silyl ethers could react under mild reaction conditions to produce the desired disaccharide condensation product, TMSOTf and phenyl sulfenic acid. The sulfenic acid could then be expected to react with TMSOTf to form the silyl phenyl sulfenate (PhSOSi(CH$_3$)$_3$), thereby regenerating triflic acid (See, below). It was reasoned that because silylated sulfenates are much more stable than sulfenic acids and can be expected not to disproportionate as readily, silylated sulfenates could help minimize water build-up. See, Nakamura *J. Am. Chem. Soc.* 1983, 105, 7172.

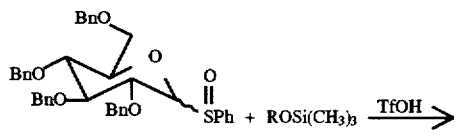

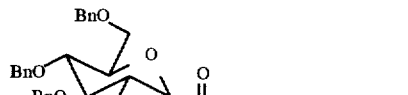

PhSOH + TMSOTf ⟶ PhSOSi(CH$_3$)$_3$ + TfOH

Accordingly, perbenzylated glucose sulfoxide 1 (1.5 equivalents) was treated with triflic acid (0.05 equivalents) in methylene chloride at −78° C. The silyl ether of the nucleophile (2b) was added to the reaction. After work-up the desired trisaccharide 3 was isolated as the major product in 60% yield. (See, first scheme in Section 5.4.1.) Thus, by using the silyl ether of the nucleophile, the reaction yield improved dramatically, i.e., from 35% to 60%.

5.4.4. Application of the Catalytic Method for the Synthesis of 2-Deoxy Oligosaccharides In subsequent investigations the scope of the catalytic triflic acid method for activating sulfoxides was explored. Table I shows a comparison of the catalytic triflic acid and stoichiometric triflic anhydride methods for glycosylation using a range of 2-deoxy glycosyl sulfoxides as glycosyl donors.

2-Deoxy glycosyl sulfoxides are notoriously unstable and tend to give low yields of coupled product (See, Table I). The stoichiometric triflic anhydride method for activating sulfoxides does not always give good results with 2-deoxy glycosyl donors. The catalytic triflic acid method however, works very well, presumably because the mild reaction conditions minimizes decomposition of 2-deoxy sulfoxides. In fact, the use of triflic acid improves the glycosylation yields by at least 50% for all the cases examined.

TABLE I

Synthesis of 2-Deoxy Glycosides

| Entry | Glycosyl acceptor | Glycosyl donor | Glycoside | Yield Tf$_2$O | TfOH | Ratio (α:β) |
|---|---|---|---|---|---|---|
| 1. | 2 | 6 | 7 | 50% | 88% | 5:1 |
| 2. | 8 | 6 | 9 | 40% | 75% | >20:1 |

TABLE I-continued

Synthesis of 2-Deoxy Glycosides

| Entry | Glycosyl acceptor[a] | Glycosyl donor | Glycoside | Yield Tf₂O | TfOH | Ratio (α:β) |
|---|---|---|---|---|---|---|
| 3. | 2 | 10 (H₃C, AcO, O, SPh) | 11 | 40% | 85% | 1:2 |
| 4. | 12 (RO-N(H)-C(=O)-OEt) | 13 (H₃C, BzO, BzO, O, SPh) | 14 | 57% | 80% | 1:2 |
| 5. | 15 (H₃C, RO, OBz, OBz, O, SPh) | 16 (H₃C, AcO, OAc, O, SPh) | 17 | 35% | 60% | >20:1 |

[a] R = H, with triflic anhydride; R = OSi(CH₃)₃, with triflic acid.

---

As can be seen from the results listed in Table I, the yields obtained from the catalytic glycosylation method are comparable to the best yields reported in the literature for the various glycal methods. Furthermore, the catalytic TfOH can be used to activate sulfoxides even in the presence of acid sensitive functional groups (Table I, Entry 2).

5.5. Aspects of the Catalytic TfOH and the Stoichiometric Tf₂O Methods for Activating Sulfoxides The two glycosylation methods complement each other. The catalytic triflic acid method is advantageous when the sulfoxide is unstable. The reaction conditions are mild; therefore, decomposition of glycosyl donors is minimized. Furthermore, side reactions such as triflation or sulfenylation of the nucleophile, which can result in decreased yields for glycosylation, do not occur with the catalytic TfOH method. However, the catalytic triflic acid method for activating sulfoxides is also significantly slower and requires slightly higher temperatures (−78° C. to −30° C.) compared to the triflic anhydride method. Additionally, the catalytic method is not efficient when electron-withdrawing protecting groups are present on the glycosyl donor.

The stoichiometric Tf₂O glycosylation method, on the other hand, works extremely well for glycosyl donors with electron-withdrawing protecting groups. It may be the best glycosylation method available when neighboring group participation is used to obtain stereoselectivity.

An important point to note is that neither triflic acid nor triflic anhydride activate anomeric phenyl sulfides under the reaction conditions used (Table I, Entry 5). Since anomeric sulfides can be readily converted to the sulfoxides under extremely mild conditions (mCPBA, CH₂Cl₂, −78° C. to 0° C.) both methods lend themselves readily to iterative strategies for oligosaccharide synthesis.

It has, thus, been shown that anomeric sulfoxides can be activated for glycosylation with a catalytic quantity of a strong organic protic acid, such as triflic acid. The glycosylation reaction proceeds under very mild conditions and offers the following advantages: (i) decomposition of sulfoxides is minimal under the reaction conditions; and (ii) problems of triflation and sulfenylation of the nucleophile are eliminated. These advantages are significant, especially in the context of solid phase oligosaccharide synthesis where sulfenylation or triflation of the nucleophile can result in the capping of a growing oligosaccharide chain on a resin and, hence, termination of the synthesis.

This catalytic method complements the triflic anhydride method, and is especially useful for the construction of 2-deoxy oligosaccharides. In fact, the catalytic triflic acid method has been employed in an efficient construction of the 2-deoxy trisaccharide of ciclamycin 0, as described elsewhere in the present disclosure. Finally, we have demonstrated that neither triflic anhydride nor triflic acid activates anomeric phenyl sulfides under the reaction conditions used; therefore, both methods readily lend themselves to iterative strategies for oligosaccharide synthesis.

5.6. Application of the Single-Step Glycosylation Method to the Synthesis of an Anthracycline Antibiotic We have found that the order of reactivity of different anomeric phenyl sulfoxides can be controlled by varying the substituents at the para position of the phenyl ring. Consequently, we have succeeded in synthesizing ciclamycin 0 trisaccharide to be synthesized stereoselectively in 25% yield from the component monosaccharides in one step. The synthetic approach is outlined in FIG. 15.

Salient features of the synthesis include employing a catalytic triflic acid glycosylation method to construct all the 2-deoxy glycosidic bonds stereoselectively. Also, the trisaccharide bears a phenyl sulfide at the anomeric center of the A ring. Anomeric phenyl sulfides are stable ("disarmed") to the conditions that activate anomeric sulfoxides for glycosylation. They can be readily oxidized under mild conditions. Thus the sulfoxide glycosylation method lends itself well to an iterative strategy for oligosaccharide synthesis. The sulfide on the A ring of the ciclamycin trisaccharide was oxidized to the corresponding sulfoxide with mCPBA and then coupled to the aglycone.

It has been discovered that the rate limiting step of the sulfoxide-mediated glycosylation reaction is triflation of the sulfoxide. The reactivity of phenyl sulfoxides can therefore be modulated by varying the substituents in the para position of the phenyl ring. The observed reactivity trend is as follows:

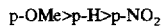

Hence, when perbenzylated glucose para-methoxy phenyl sulfoxide 27 (2.0 eq) and perbenzylated glucose phenyl sulfoxide 28 (2.0 eq) were premixed together in CH$_2$Cl$_2$ and treated with triflic anhydride (1.0 eq), base (2.0 eq) and the nucleophile 29 (2.0 eq) at −78° C., it was observed by TLC that the para-methoxy phenyl sulfoxide was activated selectively.

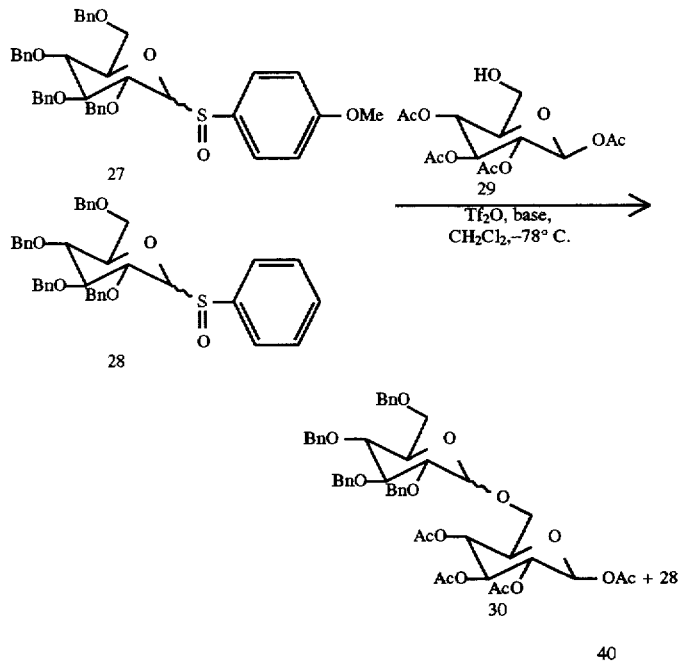

The products isolated after chromatography included the disaccharide (80%) and unreacted phenyl sulfoxide (<60% yield). However, when the same reaction was conducted in the presence of excess triflic anhydride, both the sulfoxides 27 and 28 were activated, presumably in a sequential manner, to give the glycosylated product.

Moreover, additional competition experiments revealed that the relative reactivity of glycosyl acceptors (nucleophiles) can also be manipulated. Thus, perbenzoylated 2-deoxy fucose phenyl sulfoxide 32 (2.0 eq), the nucleophile 31a (1.0 eq), the silyl ether 31b (1.0 eq), and the base (2,6-di-tert-butyl-4-methyl pyridine, 2.0 eq) were premixed in CH$_2$Cl$_2$ and cooled to −78° C. This reaction mixture was then treated with triflic anhydride (1.0 eq). The reaction was followed by TLC which indicated that the sulfoxide 32 and the nucleophile 31a were consumed (to form the disaccharide in 60% yield) while the silyl ether 31b remained unreacted.

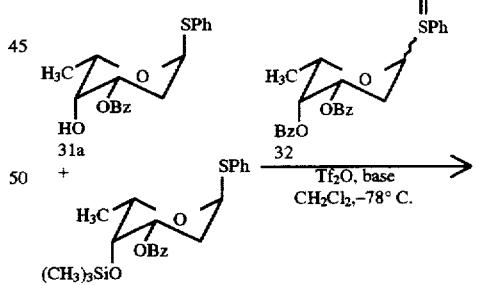

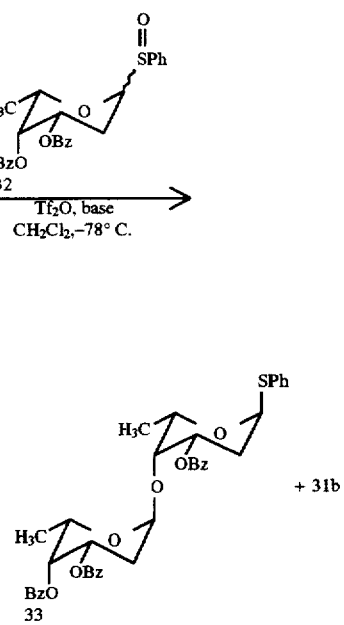

In another experiment, an excess of the sulfoxide 32 (5.0 equiv) was used; in this case, the nucleophile 31a was consumed first followed by the silyl ether 31b. Thus, silyl ethers react more slowly than unprotected alcohols as glycosyl acceptors, presumably, because they must first be unmasked.

Having demonstrated that the ability to manipulate the reactivity of both the glycosyl donors and the glycosyl acceptors, the synthesis of the ciclamycin trisaccharide was pursued according to FIG. 15. It was hoped that the p-methoxy phenyl sulfoxide B would be activated first, allowing it to react with the C-4 alcohol of A to form the AB disaccharide. Then the phenyl sulfoxide C would be activated and couple with the AB disaccharide to form the desired trisaccharide ABC.

5.6.1. One-Step Synthesis of the Trisaccharide

The sulfoxides 21, and 22 and the nucleophile 23 were premixed and dissolved in a 1:1 mixture of ether-methylene chloride at −78° C. Methyl propiolate (20 eq), followed by a catalytic quantity of triflic acid, (0.05 eq) were added to this solution. The reaction was stirred at −70° C. for half an hour and then quenched by pouring it into a saturated sodium bicarbonate solution.

The yield of the one step glycosylation is limited not by any undesired cross coupling but by the instability of the glycosyl donors, particularly the keto sulfoxide C, which decomposes readily at room temperature even in the absence of activating agent. Indeed, less than 5% of the disaccharide from the cross coupling of phenyl sulfoxide 21 and free alcohol 23 was detected even though 21 is present in excess; no disaccharide from the cross coupling of 21 and 22 was detected. The presence of the ketone functional group in the pyranose ring may contribute to the instability of this sulfoxide.

In an effort to increase the overall yield for the glycosylation, the use of a suitably protected form of the keto sulfoxide was explored.

5.6.2. Improving the BC Coupling Yields

Since the AB disaccharide 48 and the nucleophile 23 are structurally very similar, the nucleophile 23 was chosen as a model compound for the glycosyl acceptor in the glycosylation reaction with C. The precursor to the keto sulfide, the C-4 equatorial alcohol, was chosen as the glycosyl donor. The effect of different protecting groups at the C-4 center were examined.

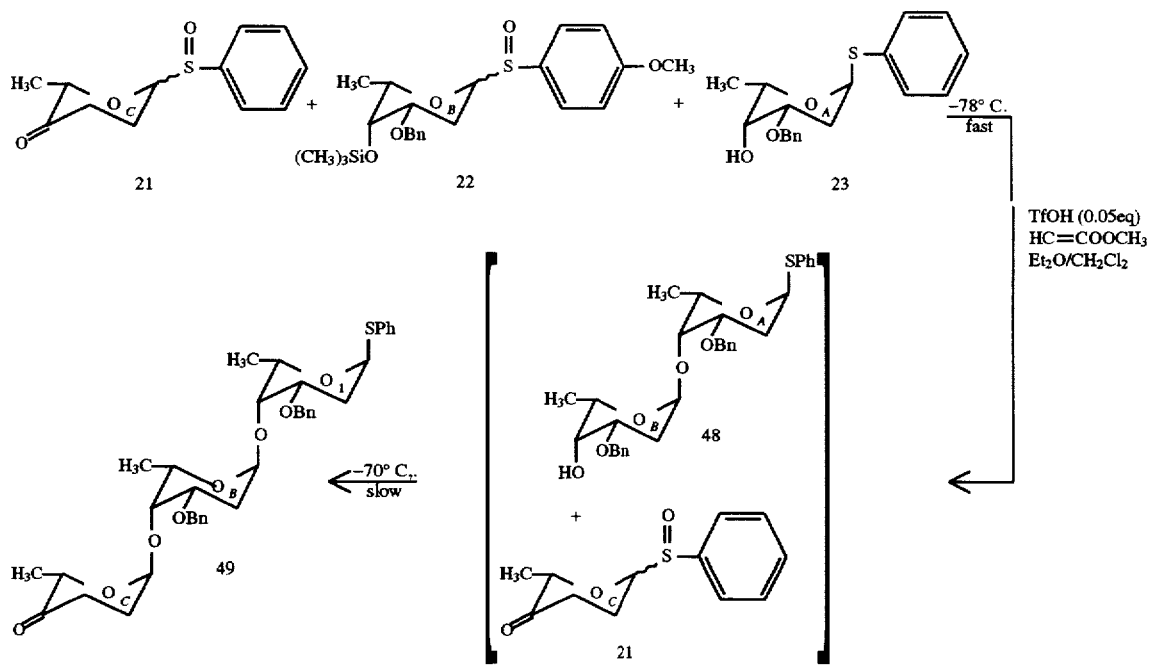

The desired trisaccharide 49 was the major product isolated in 25% yield after flash chromatography. No other trisaccharides were isolated from the reaction mixture. The only other significant coupled product isolated was the disaccharide 48, the precursor to the trisaccharide. The reaction had taken place in a sequential manner as hoped with the p-methoxy phenyl sulfoxide B becoming activated first and then reacting with the free C-4 hydroxyl of nucleophile A to form the AB disaccharide (48). Subsequently, the phenyl sulfoxide C is activated and reacts with the disaccharide AB to form the desired trisaccharide ABC (49).

In keeping with the proposed mechanism, when the same reaction is conducted at −100° C. (hexane-liquid nitrogen bath), the products isolated are the silyl ether 47 of the disaccharide AB (60% yield) along with the unactivated sulfoxide C. Performing the experiment at low temperature, thus, confirms the stepwise nature of the reaction.

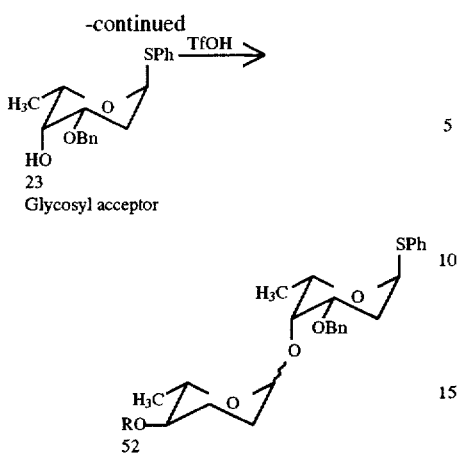

23
Glycosyl acceptor

52

The use of a suitably protected C-4 alcohol of the glycosyl donor improved the yield for the glycosylation dramatically (40–60%). For all of the cases examined, however, there was loss of stereochemical control at the anomeric center, as illustrated in Table II, immediately below.

TABLE II

Effect of Protecting Groups at C-4

| Protecting group R (51) | Yield of disaccharide (52) | Ratio α:β |
|---|---|---|
| CH₃CO | 40% | 1:2 |
| pMeOC₆H₅CH₂ | 60% | 1:2 |
| TBDMS | 60% | 1:1 |
| TBDPS | 60% | 1:1 |

The presence of a suitably protected C-4 axial hydroxyl on the C ring was also examined. In this case, the desired α stereoselectivity was obtained; however, two additional steps following glycosylation were required. These include deprotection of the C-4 alcohol followed by oxidation of the axial alcohol to the ketone. These additional steps result in decreasing the overall yield. Thus, although a 25% yield for the one step synthesis of the trisaccharide appears modest, lack of further functional group manipulations makes the synthesis efficient.

5.6.3. Coupling of Trisaccharide to the Aglycone ε-Pyrromycinone

The trisaccharide has an anomeric phenyl sulfide on the A ring. This sulfide was oxidized to the sulfoxide using mCPBA. The aglycone ε-pyrromycinone 15 (1.0 eq) and the trisaccharide sulfoxide 50 (3.0 eq) were dissolved in a 1:1 mixture of ether-methylene chloride and cooled to −78° C. Methyl propiolate (20 eq) was added to the reaction mixture, followed by a catalytic quantity (0.05 eq) of triflic acid.

A TLC taken soon after the addition of triflic acid indicated the presence of a new spot just above the aglycone. After work up and purification by chromatography, this new compound was identified by NMR spectroscopy to be the aglycone coupled to the trisaccharide (54). The $J_{H-H}$ coupling constant of 3.0 Hz for the anomeric proton was consistent with α stereochemistry of the glycosidic linkage.

5.6.4. Deprotection of Ciclamycin

To complete the synthesis of ciclamycin 0 the removal of the benzyl ether protecting groups on the A and B ring was required. The benzyl ethers were removed by hydrogenolysis using Pd(OH)₂ on carbon as the catalyst. Unfortunately, under these reaction conditions, in addition to the benzyl ethers, the aglycone also gets cleaved. In retrospect, this was not surprising since the C-7 hydroxyl of the aglycone to which the sugar is attached resembles a benzyl ether. Thus, to obtain the intact ciclamycin 0, hydrogenolysis conditions could not be used. To circumvent this problem, the protecting groups on the sugar rings A and B needed to be changed.

Para methoxy benzyl ethers can be readily cleaved under mild oxidative conditions using 2,3-dichloro-5,6-dicyano-1, 4-benzoquinone (DDQ). See, for example, Ikemoto and Schreiber *J. Am. Chem. Soc.* 1990, 112, 9657; Horita et al. *Tetrahedron*, 1986, 42, 3021; Oikawa et al. *Tet. Lett.* 1984, 25, 5393; and *Carbohydrates*, Ed. Collins, P. M. Chapman and Hall: New York, 1987. Thus, a 1:1 mixture of marcellomycin (which bears a trisaccharide at the C-7 position of the aglycone) and the A ring (with p-methoxy benzyl ether protecting group at C-3) were treated with an excess of DDQ. Under these reaction conditions only the p-methoxy benzyl ether on the A ring was hydrolyzed while the marcellomycin remained intact. Based on this result, the protecting groups on the ciclamycin trisaccharide may preferably be changed from benzyl to p-methoxy benzyl ethers.

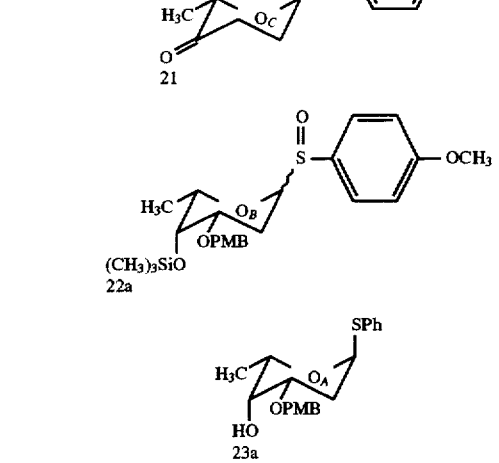

PMB = para-methoxybenzyl

The monosaccharides 21, 22a and 23a can be used to synthesize the desired ciclamycin trisaccharide in one-step (20% yield) following the usual procedure. The trisaccharide sulfide was oxidized to the sulfoxide with mCPBA and then coupled to the aglycone using the catalytic triflic acid glycosylation method.

The deprotection of the coupled product 54a required the removal of the para-methoxy benzyl ethers. The coupled product 54a (1 mg) was treated with DDQ in CH₂Cl₂ and stirred at room temperature for 10 hours. The reaction proceeded cleanly to give ciclamycin 0 quantitatively.

5.7. Rapid Synthesis of Oligosaccharides Through Controlled Polymerization: Constrained Libraries of 2-Deoxy Fucose Homopolymers The 2-deoxy fucose sulfoxide B used for the one step synthesis of the ciclamycin trisaccahride is a bifunctional sugar. It contains a leaving group at the anomeric center (p-methoxy phenyl sulfoxide) and can serve as a glycosyl donor. In addition, it has a silyl ether at the C-4 center and can also serve as a glycosyl acceptor.

The most common 2-deoxy sugars found in bioactive natural products are 2,6-dideoxy sugars. They frequently occur as dimers or trimers attached to an aglycone. Given our success with the synthesis of a complicated trisaccharide in one step, we wondered if it was possible to extend this idea for the rapid assembly of oligosaccharides through controlled polymerization. The bifunctional 2,6-dideoxy B ring presented an opportunity to explore the possibility of synthesizing homopolymers in a single reaction.

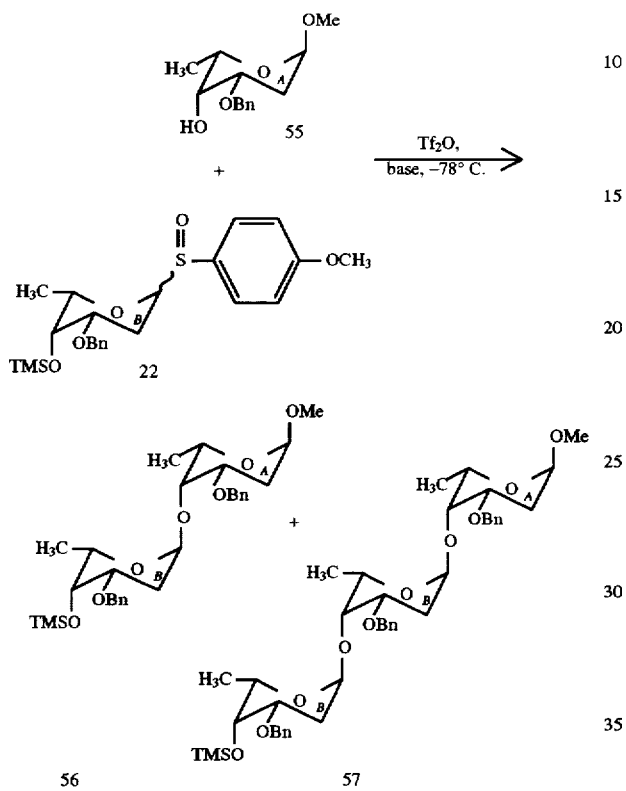

The sulfoxide 22 (2.0 eq) and the nucleophile 55 (1.0 eq) were premixed in 1:1 mixture of ether-methylene chloride and cooled to −78° C. The reaction mixture was treated with base (2.0 eq) and triflic anhydride (1.0 eq) (See, above). A TLC of the reaction taken soon after indicated the presence of two new spots related to product. After chromatography two products were isolated and characterized by NMR spectroscopy. These products were the AB disaccharide 56 (45% yield) and the ABB trisaccharide 57 (20% yield). The $J_{H-H}$ coupling constants for the anomeric protons were consistent with α stereochemistry for all the glycosidic linkages. This result indicated that homopolymers of 2-deoxy fucose can be formed stereoselectively in one step.

To determine whether higher order polymers of 2-deoxy fucose could be obtained, the number of equivalents of the sulfoxide B (22) used in the glycosylations was increased.

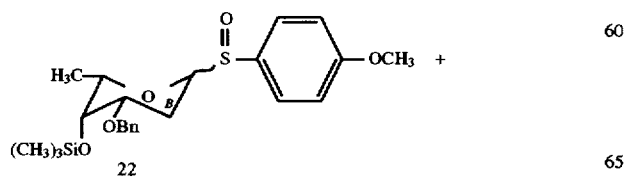

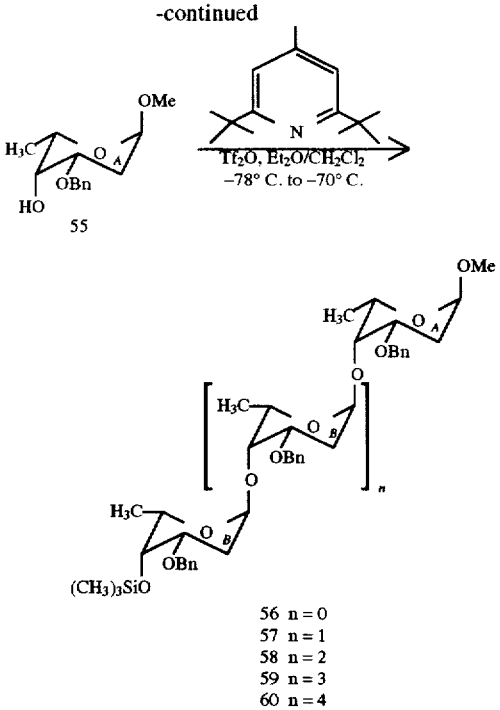

When 5.0 equivalents of B and 1.0 equivalent of A were used, a statistical mixture of di, tri, tetra, penta and hexasaccharides was obtained in a single reaction, as noted above. Thus, using the sulfoxide method it is possible to rapidly synthesize a mixture of homopolymers of 2-deoxy fucose through controlled polymerization.

The sulfoxide glycosylation method is powerful and versatile. It can be used to rapidly synthesize a complicated trisaccharide like ciclamycin from component monosaccharides in a single reaction. This strategy could be extended to synthesize a hexasaccharide from the component disaccharides in one step. In addition, by using bifunctional sugars it is possible to synthesize a mixture of homopolymers (of varying chain length) in a single step with the sulfoxide method. Thus far, we have only examined 2-deoxy fucose as a substrate for the controlled polymerization reactions. Nevertheless, this strategy could in principle be extended to include other bifunctional substrates as well.

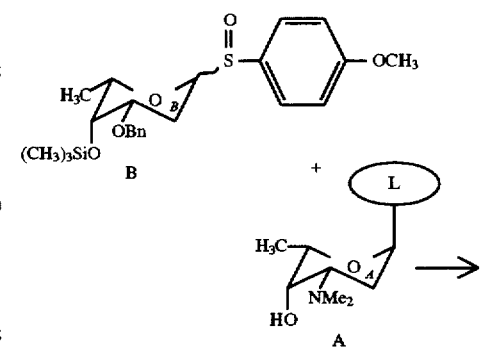

-continued

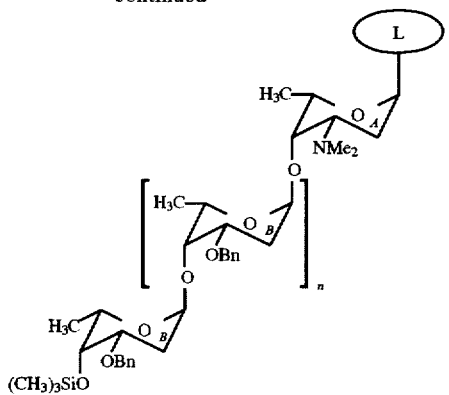

By using a combination of the one-step and controlled polymerization strategy it is possible to very rapidly synthesize libraries of oligosaccharides with various aglycones attached, as shown above. These oligosaccharide libraries can be screened for DNA binding, for example, by using DNA affinity chromatography. Such a study will help elucidate the features in oligosaccharides that confer DNA binding.

The sulfoxide glycosylation method is rapid, flexible and efficient for the construction of oligosaccharides using conventional approaches. The reactivity of glycosyl donors can be modulated by varying the substituent at the para position of the phenyl ring. Electron-donating substituents accelerate the rate of the reaction relative to the unsubstituted case, while electron withdrawing groups decelerate the rate of the reaction. The reactivity of glycosyl acceptors can be modulated as well. Silyl ethers react more slowly in glycosylations than free alcohols. This permits the controlled formation of two or more glycosidic linkages in a single reaction. This strategy was employed to synthesize the ciclamycin 0 trisaccharide stereoselectively from component monosaccharides in a single step. Furthermore, bifunctional sugars can be used to synthesize libraries of oligosaccharides. The sulfoxide method is thus a versatile glycosylation method that allows the rapid synthesis of oligosaccharides through controlled oligomerization.

5.8. Formation Of Glycosidic Linkages On The Solid Phase

A potential glycosyl acceptor is attached to an insoluble support (hereafter termed the resin) through a linkage that can be readily cleaved at the end of the synthesis using conditions that do not damage glycosidic linkages. The resin may be any insoluble polymer that swells in organic solvents and has sites for attaching the glycosyl acceptor. Preferred resins include, but are not limited to, polystyrene resins, such as the Merrifield resin, and PEG-derivatized polystyrene resins, such as the TentaGell resins.

Figure 4A:
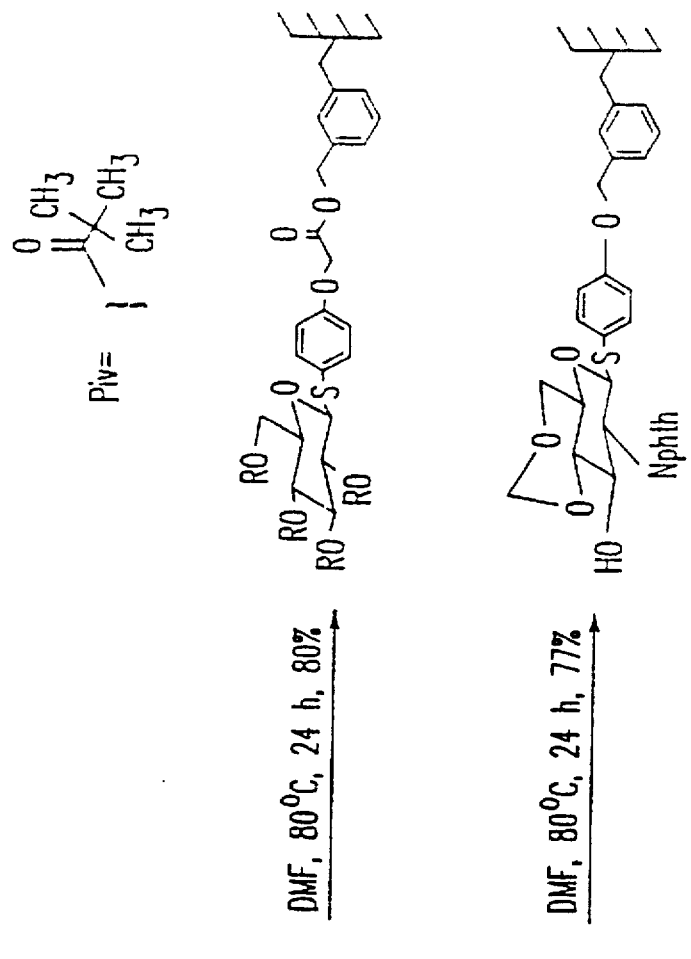
FIGS. 4A and 4B illustrate methods of forming and removing two exemplary types of linkages from a solid support (e.g., polystyrene resin).
Figure 4B:
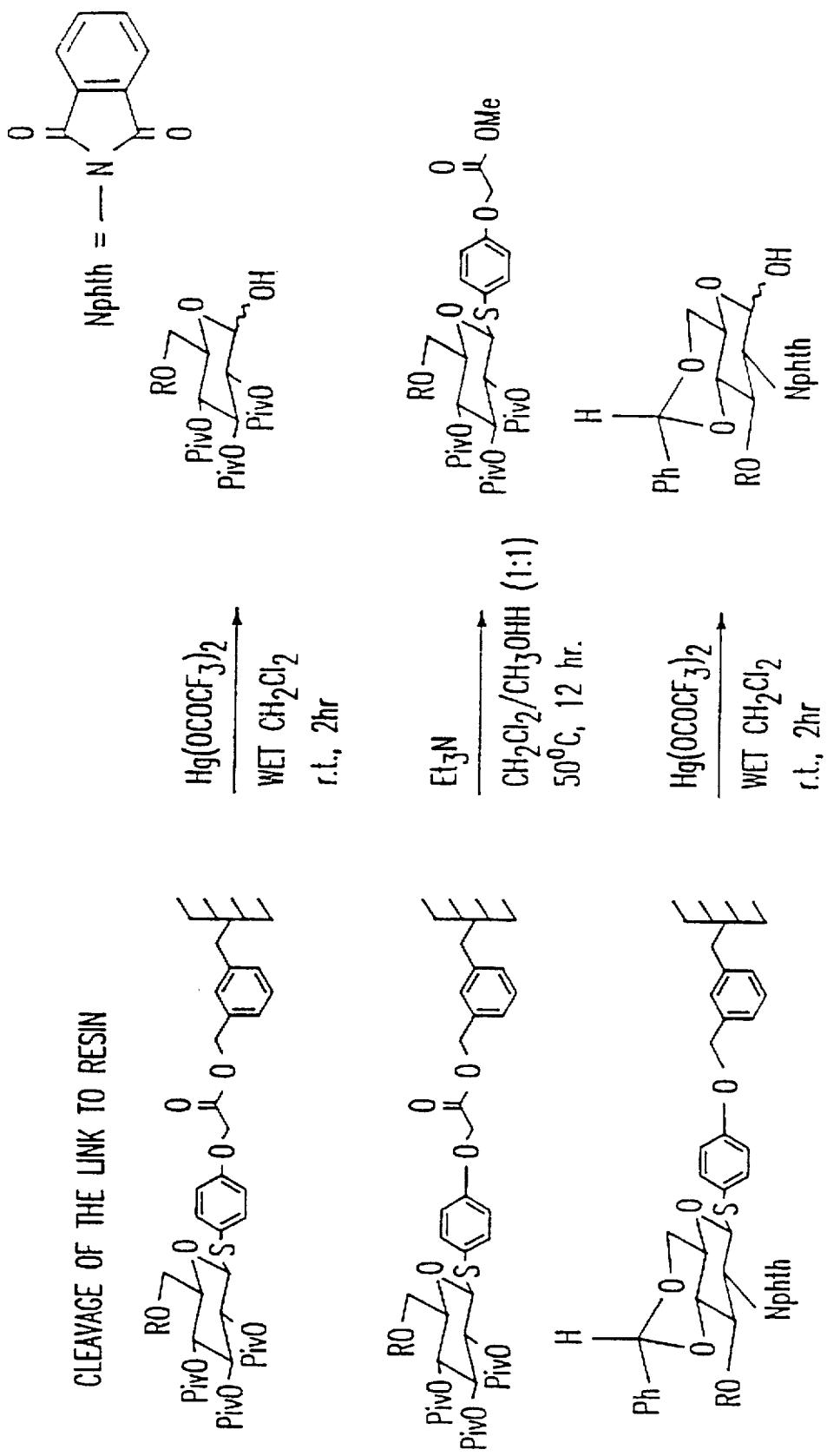

The type of linkage depends on the type of functional sites available on the polymer phase and on the glycosyl acceptor. Because polystyrene-based resins can be readily functionalized with chloromethyl subsitituents, the linkage is typically a benzyl ether, formed by nucleophilic displacement of a benzyl chloride on the resin with a free hydroxyl on the glycosyl acceptor. Alternatively, a benzyl ester can be used which is formed by nucleophilic displacement of a benzyl chloride on the resin with the salt of an acid on the glycosyl acceptor. (FIG. 4) Both types of linkages can be readily hydrolyzed at the anomeric carbon of the glycosyl acceptor by treating the resin with Hg(II) compound. Alternatively, the ester linkage can be hydrolyzed by methanolysis as is done for ester linkages to resins in peptide synthesis. The Hg(II) method is preferred for treating aliquots of the resin to monitor the extent of reaction. The Hg(II) method is also preferred when the lactol of the completed oligosaccharide is desired as a final product. The methanolysis method is preferred when the sulfide of the completed oligosaccharide is desired as a final product (FIG. 4).

The potential glycosyl acceptor may be any molecule having one or more potentially reactive nucleophiles, including potentially reactive hydroxyls, amines, and/or thiols, provided that it also has a suitable site for attachment to the resin. A potentially reactive nucleophile is a free nucleophile or a nucleophile with a temporal protecting group that can be removed readily once the glycosyl acceptor is attached to the resin. The potential glycosyl acceptor may also have permanently protected nucleophiles, which are nucleophiles that cannot be deprotected under the conditions that are used to remove the temporal protecting groups. The potential glycosyl acceptor may be a sugar or some other nucleophile-bearing molecule, including, but not limited to, steroids, amino acids or peptides, polar lipids, polycyclic aromatic compounds, and the like. Protecting group schemes for sugars that permit selective protection and deprotection at any position are well known. See, e.g., Binkley, above.

Following attachment to the resin, the potentially reactive nucleophile is selectively deprotected, if necessary, and the derivatized resin is lyophilized overnight and stored in a desiccator until use. The resin is then preferably placed in a specially designed reactor vessel with a glass frit. Any openings are sealed, e.g., with rubber septa (See, e.g., FIG. 5). There may be many variations on the general apparatus. However, the important features can be enumerated as follows:

a) An inlet for the addition of solvent and dissolved reagents to the reaction chamber and which is suitable for maintaining an anhydrous atmosphere; (In the apparatus shown, a rubber septum over a cup-shaped opening permits the addition of solvent and dissolved reagents by canula or syringe needle while preventing exposure of the reaction chamber to the outside air. In a preferred embodiment of the reaction vessel, this inlet is also equipped with a T-connector or similar adapter which allows the inlet to double as a vent for releasing inert gas, such as nitrogen or argon, to prevent the build up of excess pressure within the apparatus.)

b) A reaction chamber for holding the resin and reagent solution which is equipped with a frit or filter of such coarseness or porosity so that unbound components, such as unreacted dissolved reagents, but not resin, can be washed from the reaction chamber;

c) A port, located on the side of the frit which is opposite to the inlet side, for introduction of an inert gas; the gas passes through the frit, thus agitating the reaction mixture, and settles over the reaction mixture, thus maintaining an anhydrous atmosphere inside the reaction chamber. (As evident from FIG. 5, the argon or nitrogen passes through the resin from below, opposing the flow of solvent through the frit and agitating the resin simultaneously. In a preferred embodiment, this port is equipped with a T-connector or similar adapter to allow the port to be attached to an aspirator for removal of solvent under vacuum.)

It should also be noted that the configuration of the apparatus is such that the apparatus up to the level of most of the reaction chamber can be immersed in a cooling bath. Hence, below the frit, the apparatus may be in a U-shape, as shown in FIG. 5, so that the gas port can be positioned above the cooling medium.

Next, an inert gas, such as argon or nitrogen, preferably argon, is passed through the resin for about 1 hour. The resin is then suspended in 3–5 mL anhydrous solvent including but not limited to toluene, ether, THF, methylene chloride, chloroform, propionitrile, or mixtures thereof). From the discussion in the previous section, it is understood that the choice of solvent will influence the stereochemical outcome of glycosylation for reactions in which neighboring group participation is not involved. The argon flow is adjusted to agitate the resin gently and prevent solvent from draining through the frit.

A glycosyl sulfoxide is then dissolved under anhydrous conditions in 2–4 mL anhydrous solvent and transferred by canula to the reactor vessel containing the resin. The glycosyl sulfoxide may also have protecting groups present elsewhere in the molecule. If the saccharide chain is to be further extended, the glycosyl sulfoxide must also have at least one temporal protecting group. Typically the glycosyl sulfoxide is added in 2–4-fold excess relative to the amount of glycosyl acceptor on the resin.

Depending on the activation method used to initiate the glycosylation reaction, a non-nucleophilic base, such as 2,6-di-t-butyl-4-methyl pyridine or Hunig's base (diisopropyl ethylamine), may be dissolved with the glycosyl sulfoxide or added to the vessel containing the resin. When used, the base is preferably present in a slight excess relative to the amount of glycosyl sulfoxide added.

The reactor vessel containing the resin is then immersed in a cold bath at −78° C. To activate the glycosyl donors for reaction, either 0.05 equiv. (i.e., catalytic) triflic acid or 0.5 equiv. of triflic anhydride diluted in a large volume of anhydrous solvent is added to the reaction mixture under anhydrous conditions. The molar equivalents are measured relative to the amount of glycosyl sulfoxide used. Also, dilution in a large volume means that the volume of the neat activating agent is diluted at least 100-fold by the addition of the appropriate volume of solvent (e.g., 1 μL of neat activating agent is added to at least 99 μL of solvent before addition to the donor).

The addition of activating agent may be carried out, for example, with the aid of a canula. Other activating agents suitable in the present method include, but are not limited to, an alkyl- or arylsilyl triflate (e.g., trimethylsilyl triflate), an alkyl- or arylsulfenyl triflate, and an alkyl- or arylselenenyl triflate. If protons are generated in the reaction (as when 0.5 equiv. of triflic anhydride is used to activate the sulfoxide), an acid scavenger must be present in the resin mixture. Moreover, unless the activating agent is used in catalytic amounts (e.g., <0.1 equiv relative to glycosyl sulfoxide), the activating agent must be diluted about 100-fold or more prior to addition. It has been discovered with triflic anhydride that dilution is critical, triflation of the glycosyl acceptors on the resin thus being avoided.

Next, the resin is gently agitated by the flow of argon. Typically the reaction is allowed to continue for approximately 30 minutes after which the resin is rinsed repeatedly to remove byproducts and unreacted glycosyl donor. If desired, the reaction may be monitored by removing aliquots of resin, rinsing the resin to remove reagents, and then hydrolyzing the linkage to the resin. Alternatively, if the glycosyl acceptor is a sugar which is attached to the resin via a sulfide derivative linked to the anomeric carbon, the link to the anomeric carbon may be hydrolyzed with a Hg(II) compound. Hydrolysis by Hg(II) is preferred for monitoring the extent of the glycosylation reaction.

The products and the progress of the reaction may be analyzed by thin layer chromatography using standards for comparison. For example, after Hg(II) hydrolysis of an aliquot from the reaction mixture, the soluble products are analyzed by TLC. The absence of the monosaccharide residue that was bound to the resin is taken as an indication that the reaction has proceeded to completion.

To obtain the products, the resin is typically rinsed repeatedly with methylene chloride followed by methanol (preferably, about 10 cycles). The coupling may be repeated if necessary to drive the reaction to completion. Otherwise, if the saccharide chain is to be further extended, temporal protecting groups are next removed, the resin rinsed repeatedly to remove reagents, and another glycosyl sulfoxide residue added as before.

Upon completion of the synthesis and rinsing to remove reagents, the disaccharide, oligosaccharide or glycoconjugate is removed from the resin. The product may then be purified and/or deprotected if desired. Alternatively, the disaccharide, oligosaccharide or glycoconjugate may be used while still attached to the resin in screening procedures to elucidate biological activity.

Strategically, mixtures of oligosaccharides can also be produced by solid phase synthesis and screened for biological activity. To produce mixtures, more than one different type of glycosyl sulfoxide is added to the resin at one or more cycles of the synthesis. It may be desirable to vary the sugars at only one position in the synthesis to probe the structural requirements at that position. In this way, structure-activity relationships can be rapidly evaluated in cases where both a particular carbohydrate and its receptor are known. Alternatively, it may be desirable to vary the sugars at several positions in the synthesis, producing a complex mixture that can be screened for binding to various receptors. In either case, if activity is detected, the active compound(s) can be identified using methods similar to those used in the peptide field for identifying active peptides from mixtures produced by solid phase synthesis. See, for example, Furka et al. *Int. J. Peptide Protein Res.* 1992, 37, 487; Lam et al. *Nature* 1991, 354, 82; Houghten, R. A. *Nature* 1991, 354, 84; Zuckermann et al. *Proc. Natl. Acad. Sci. USA* 1992, 89, 4505; Petithory *Proc. Natl. Acad. Sci. USA*, 1991, 88, 11510; Geyse et al. *Proc. Natl. Acad. Sci. USA*, 1984, 81, 3998; Houghten *Proc. Natl. Acad. Sci. USA*, 1985, 82, 5131; Fodor et al. *Science* 1991, 251, 767.

6. EXAMPLES

The following specific examples are provided to better assist the reader in the various aspects of practicing the present invention. As these specific examples are merely illustrative, nothing in the following descriptions should be construed as limiting the invention in any way. Such limitations are, of course, defined solely by the accompanying claims.

6.1. Synthesis Of The Ciclamycin 0 Trisaccharide In A Single Step

FIG. 1 illustrates one embodiment of the process for forming multiple glycosidic linkages in solution in which a specific trisaccharide, the ciclamycin 0 trisaccharide, is synthesized stereospecifically in protected form in a single step from the component monosaccharides. The monosaccharides 1, 2, and 3 are combined in a ratio of 3:2:1, as shown (417 mg, 1.812 mmol; 541 mg, 1.2 mmol; and 165 mg, 0.604 mmol, respectively). Water is then removed from the mixture by distillation of the azeotrope from anhydrous toluene. (This drying step is carried out by dissolving the sugar mixture in toluene (ca. 30 mL) and removing the toluene on a rotary evaporator under vacuum. The anhydrous sugar mixture is then used directly or stored under inert gas until needed.)

The anhydrous sugar mixture is next dissolved in 20 mL of anhydrous methylene chloride in a 50 mL flame dried flask. Then, 20 mL of freshly distilled diethyl ether containing 20 equivalents of methyl propiolate is added. (The propiolate ester is used to scavenge the sulfonic acid that is produced in the reaction.) The solution is then cooled to −78° C. A catalytic amount of triflic acid (5.3 μL, 0.05 eq.) is then added dropwise, and the reaction is allowed to warm from −78° to −70° C. over a period of 45 minutes and then quenched with saturated NaHCO$_3$. The biphasic mixture is then extracted with CH$_2$Cl$_2$ (3×15 mL). The organic extracts are combined, dried over anhydrous Na$_2$SO$_4$ and concentrated. The major product, trisaccharide 5, is isolated in 25% yield, based on monosaccharide 3, after extraction with ethyl acetate and flash chromatography on silica gel (20% ethyl acetate/petroleum ether).

The $^1$H NMR spectra of trisaccharide 5 are shown in FIGS. 12 and 13. The stereoselectivity achieved is a function of the donor-acceptor pairs and the glycosylation conditions (solvent, temperature). We have found that catalytic triflic acid does not anomerize glycosidic linkages at an appreciable rate below −30° C. No other trisaccharide is produced. Indeed, the only other significant coupled product detected from the reaction is disaccharide 4 (Scheme 1 of FIG. 1, 15% yield; $^1$H NMR, FIG. 14), the precursor to the trisaccharide 5. Less than 5% of the disaccharide from the cross coupling of phenyl sulfoxide 1 and free alcohol 3 is detected even though 1 is present in excess; no disaccharide from the cross coupling of 1 and 2 is detected.

Thus, the yield of trisaccharide 5 in the reaction is not limited by any undesired cross coupling. However, the instability of the glycosyl donors, particularly keto sulfoxide 1, which decomposes readily at room temperature even in the absence of activating agent, can affect the yield.

The products of the reaction indicate that glycosylation takes place in a sequential manner, with p-methoxy phenyl sulfoxide 2 activating faster than phenyl sulfoxide 1, and C-4 alcohol 3 reacting faster than C-4 silyl ether 2. Consistent with this sequence, if the reaction is quenched at −100° C., only the silyl ether of disaccharide 4 can be isolated (60%).

Thus, the products of the one step reaction described above illustrate the principle established by the present invention; i.e. that the reactivity of both glycosyl donors and glycosyl acceptors can be manipulated effectively so that glycosylation takes place in a sequential manner to produce a desired oligosaccharide in a single step.

Finally, it should be noted that the trisaccharide (5) produced in the one step reaction has an anomeric phenyl sulfide on the A ring. Anomeric phenyl sulfides are stable ("disarmed") to the conditions that activate anomeric phenyl sulfoxides for glycosylation, but they can be readily oxidized under mild conditions. See, Mootoo et al. *J. Am. Chem. Soc.* 1988, 110, 5583; Veeneman and van Boom *Tet. Lett.* 1990, 31, 275; and Mehta and Pinto *Tet. Lett.* 1991, 32, 4435. Thus, the sulfoxide glycosylation reaction also lends itself well to an iterative strategy for oligosaccharide synthesis. See, Friesen and Danishefsky *J. Am. Chem. Soc.* 1989, 111, 6656; Halcomb and Danishefsky *J. Am. Chem. Soc.* 1989, 111, 6661; Mootoo et al. supra; Veeneman and van Boom, supra; and Mehta and Pinto, supra; Nicolaou et al. *J. Am. Chem. Soc.* 1984, 106, 4189; Mootoo et al. *J. Am. Chem. Soc.* 1989, 111, 8540; Barrett et al. *J. Am. Chem. Soc.*, 1989, 111, 1392. The ciclamycin trisaccharide 5 is oxidized to the corresponding sulfoxide in 80% yield (1.2 eq. mCPBA, CH$_2$Cl$_2$, −78° C. to −50° C., 2 hr) and is ready for coupling to the ciclamycin chromophore.

Figure 9A:
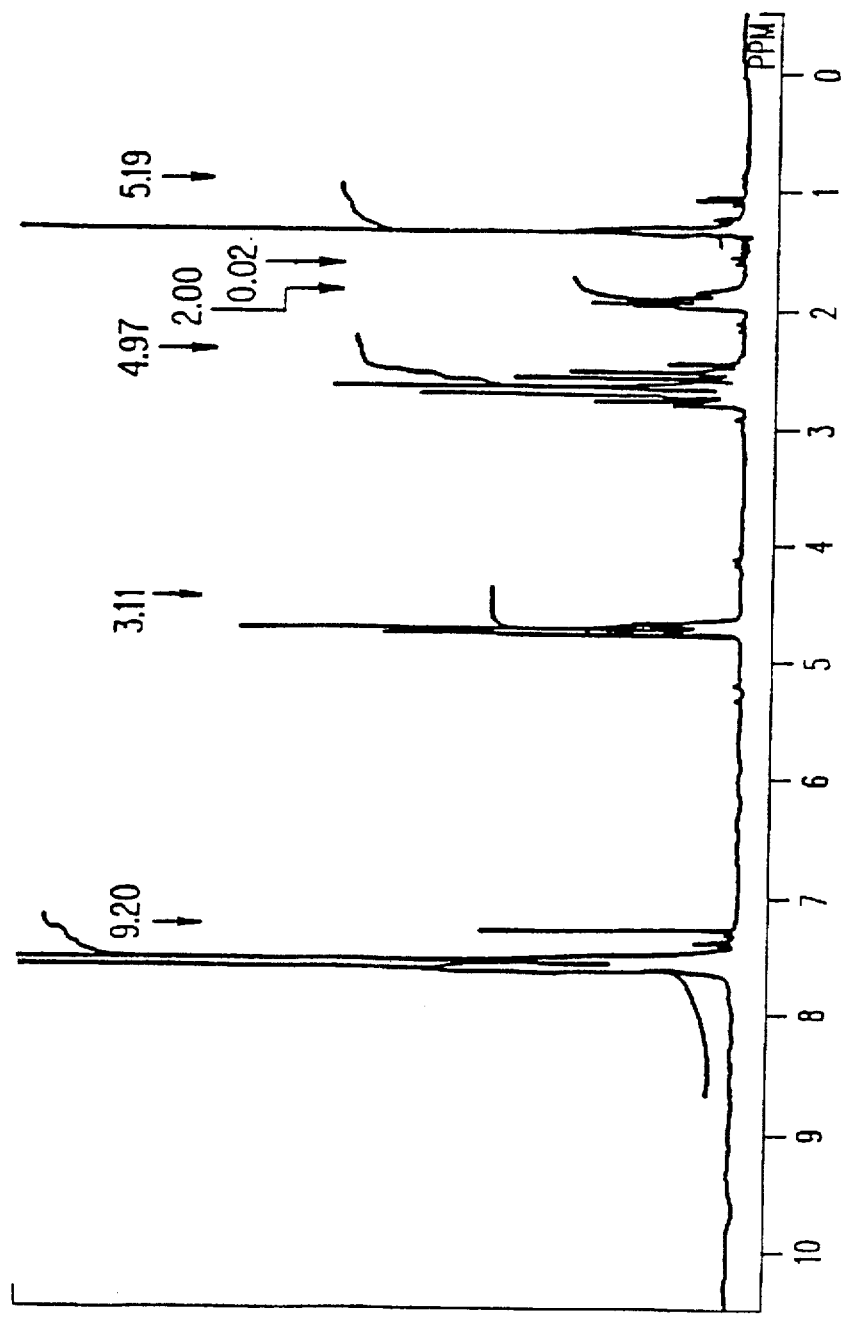
FIG. 9A is a $^1$H NMR spectrum of monosaccharide 1 of FIG. 1.
Figure 9B:
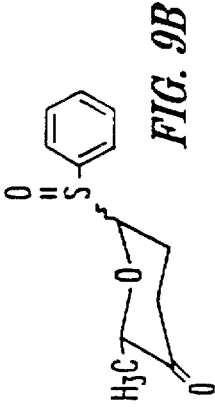
FIG. 9B shows the structure of monosaccharide 1.
Figures 10A, 10B:
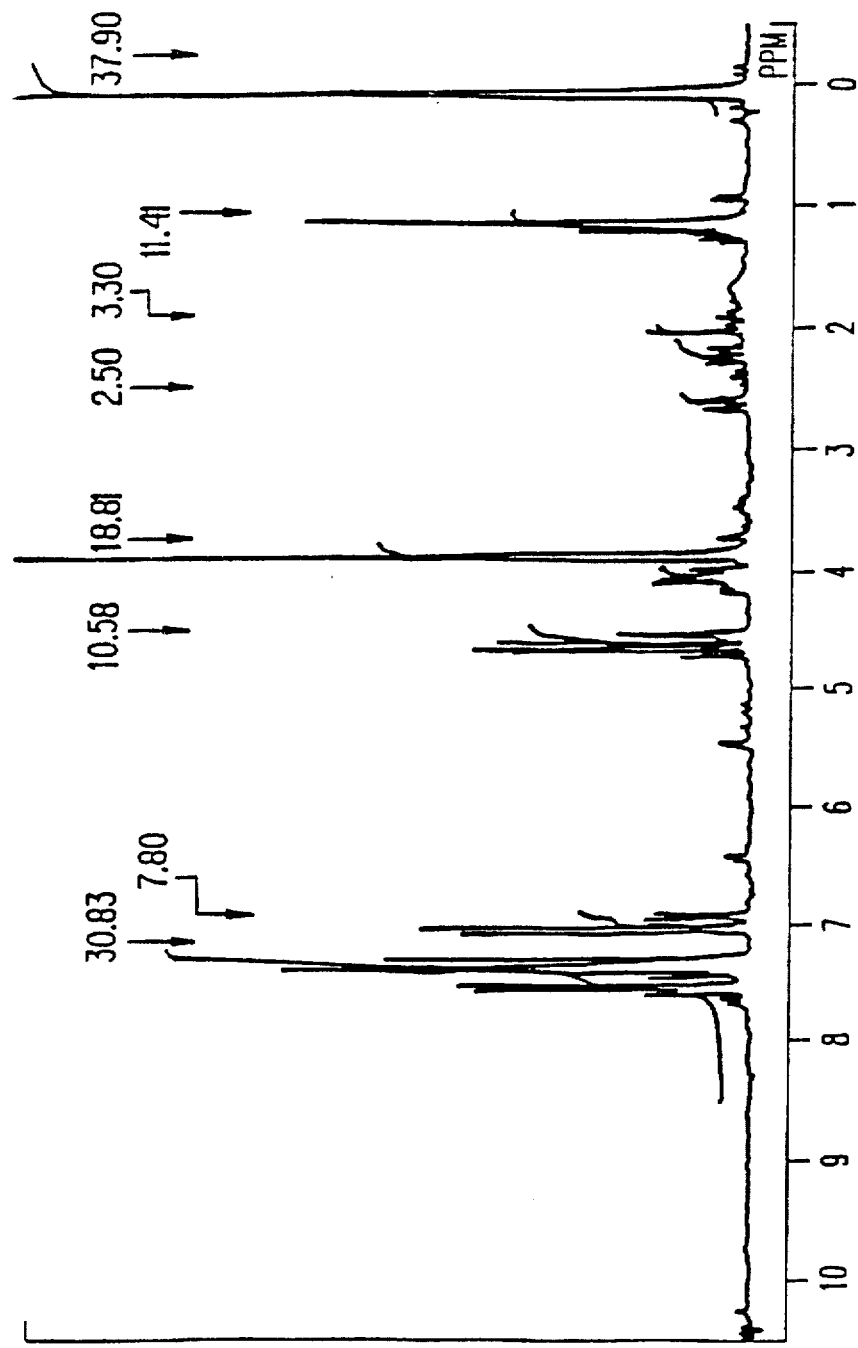
FIG. 10A is a $^1$H NMR spectrum of monosaccharide 2 of FIG. 1.
FIG. 10B shows the structure of monosaccharide 2.
Figures 11A, 11B:
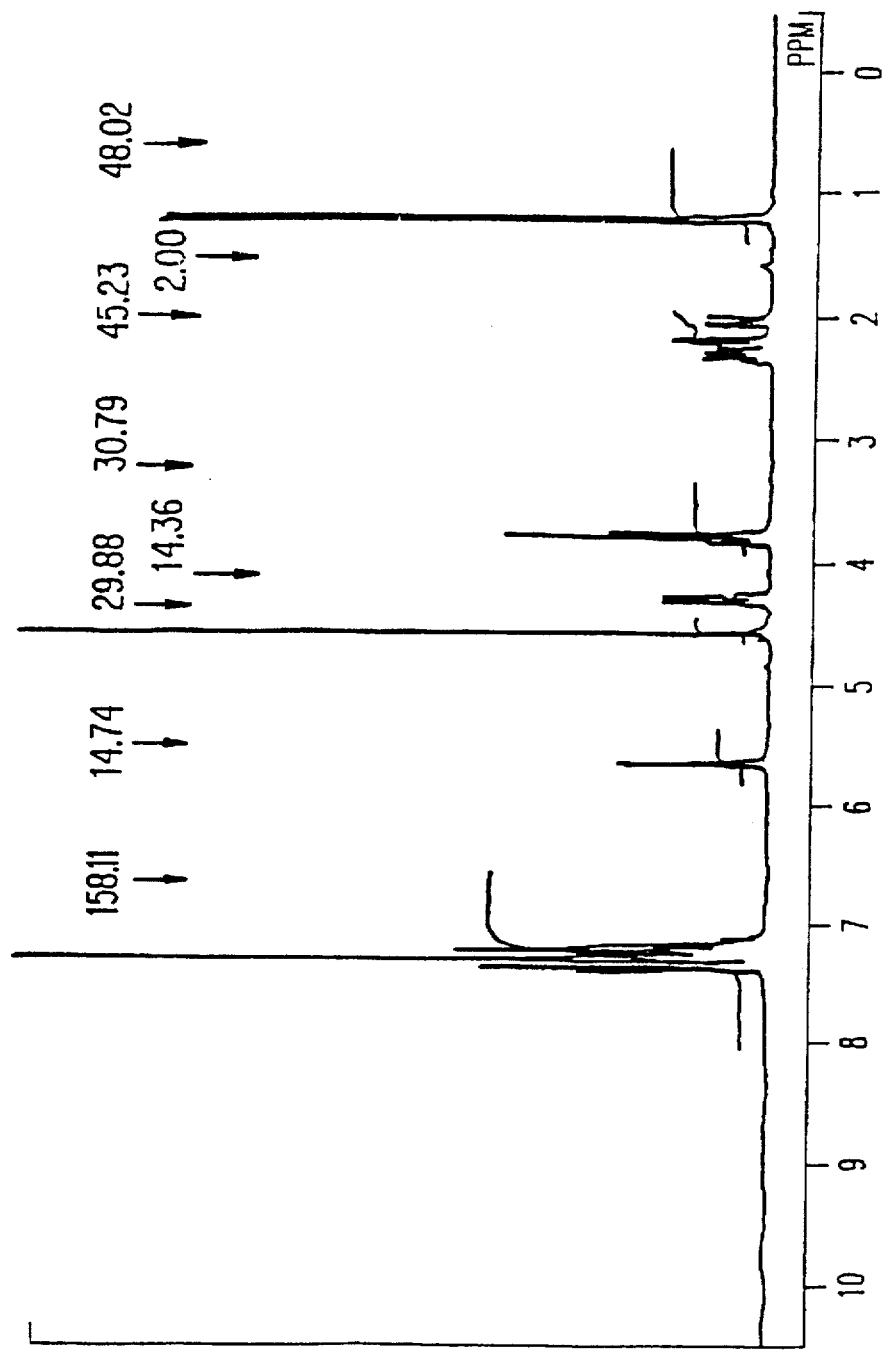
FIG. 11A is a $^1$H NMR spectrum of monosaccharide 3 of FIG. 1.
FIG. 11B shows the structure of monosaccharide 3.

Monosaccharide 1 is prepared from L-rhamnose in 60% overall yield ($^1$H NMR; FIG. 9). See, Martin et al. *Carbohydr. Res.* 1983, 115, 21. Monosaccharides 2 ($^1$H NMR; FIG. 10) and 3 ($^1$H NMR; FIG. 11) are prepared from L-fucose with overall yields of 47% and 52%, respectively. See, Giese et al. *Angew Chem. Int. Ed. Engl.* 1987, 26, 233.

According the another method of the present invention, the preparation of individual starting materials, their orchestrated condensation to form the trisaccharide of interest, and their subsequent coupling to an aglycone are described in greater detail, below.

6.1.1. Phenyl-3-O-benzoyl-2,6-dideoxy-1-thio-α-L-galactopyranoside (31a)

The compound 37 (1.41 g, 5.9 mmol) is dissolved in dichloromethane and cooled to −78° C. under argon. Sodium hydride (566 mg, 23.6 mmol) is added to this solution. There is brisk effervescence. After ten minutes, benzoyl chloride (2.05 mL, 17.7 mmol) is added to the solution. The reaction is stirred at −78° C. for ½ hour, gradually warmed −60° C. and then quenched by pouring into saturated solution of NaHCO$_3$. The resulting solution is extracted with CH$_2$Cl$_2$ (3×50 mL); the organic layers are combined, dried over anhydrous Na$_2$SO$_4$ and concentrated under vacuum. Flash chromatography (20% ethyl acetate-petroleum ether) yields the product as a white solid (1.6 g, 70%). R$_f$=0.3 (20% ethyl acetate-petroleum ether). $^1$H NMR (CDCl$_3$, 270 MHz) δ8.3 (m, 2H), 7.8–7.2 (m, 8H), 5.85 (d, J=5.94 Hz, 1H, H-1), 5.55 (m, 1H, H-3), 4.7 (q, J=6.60 Hz, H-5), 4.1 (bs, 1H, H-4), 2.78 (dt, J=5.93, 12.86 Hz, 1H, H-2$_{ax}$), 2.33 (dd, J=4.95, 13.19 Hz, H-2$_{eq}$), 2.12 (bs, 1H, OH), 1.41 (d, J=6.60 Hz, 3H, CH$_3$).

6.1.2. Phenyl-3,4-O-benzoyl-2,6-dideoxy-1-thio-α-L-galactopyranoside (32a)

This compound is synthesized from phenyl-3,4-O-diacetyl-2,6-dideoxy-1-thio-α-L-galactopyranoside 36 in the following two step sequence: (i) NaOMe/CH$_3$OH, amberlite IR(120) plus ion-exchange resin; and (ii) Benzoyl chloride, pyridine. R$_f$ (TLC)=0.3 (30% ethyl acetate-petroleum ether). $^1$H NMR (CDCl$_3$, 270 MHz) δ8.1–7.7(m, 6H), 7.5–7.2 (m, 9H), 5.71 (m, 1H, H-3), 5.61 (bs, 1H, H-4), 5.48 (d, J=5.28 Hz, 1H), 4.33 (q, J=6.27 Hz, 1H, H-5), 2.45 (dt, J=3.63, 12.54 Hz, 1H, H-2$_{ax}$), 2.17 (dd, J=4.95, 12.54 Hz, 1H, H-2$_{eq}$), 1.25 (d, J=6.27 Hz, 3H, CH$_3$). $^{13}$C NMR (CDCl$_3$, 67.5 MHz) δ169.49, 164.88, 161.88, 134.11, 130.77, 130.00, 129.28, 129.13, 128.56, 128.44, 128.28, 128.12, 127.83, 83.33, 69.93, 67.81, 65.74, 53.22, 30.62, 16.17.

6.1.3. Phenyl-3,4-O-benzoyl-2,6-dideoxy-1-sulfinyl-α-L-galactopyranoside (32)

The sulfide 32a (900 mg, 1.99 mmol) is dissolved in dichloromethane and cooled to −78° C. (acetone/dry-ice bath) under argon. mCPBA (483 mg, 2.80 mmol) is added and the reaction is stirred at −78° C. for one hour. The reaction is gradually warmed to 0° C. over a period of two hours and then quenched by pouring into saturated solution of NaHCO$_3$. The resulting biphasic mixture is extracted with CH$_2$Cl$_2$ (3×25 mL). The organic layers are combined, washed with brine and dried over anhydrous Na$_2$SO$_4$. Flash chromatography (40% ethyl acetate-petroleum ether) provides the sulfoxide 32 as a white crystalline solid (690 mg, 80% yield). R$_f$ (TLC)=0.4 (40% ethyl acetate-petroleum ether). $^1$H NMR (CDCl$_3$, 270 MHz) δ8.1–7.65 (m, 6H), 7.5–7.2 (m, 9H), 5.9 (m, 1H, H-3), 5.68 (d, J=2.64 Hz, 1H, H-4), 4.71 (d, J=5.61 Hz, 1H, H-1), 4.63 (q, J=6.27 Hz, 1H, H-5), 2.80 (dd, J=5.28, 14.19 Hz, 1H, H-2$_{eq}$), 2.55 (dt, J=5.94, 12.53 Hz, 1H, H-2$_{ax}$), 1.27 (d, J=6.27 Hz, 3H, CH$_3$).

6.1.4. 3,4-O-Benzoyl-2,6-dideoxy-galactopyranosyl-α-(1→4)-phenyl-3-O-benzoyl-2,6-dideoxy-1-thio-α-L-galactopyranoside (33)

35

The sulfoxide 32 (177 mg, 0.4 mmol), nucleophile 31a (80 mg, 0.2 mmol), silyl ether 31b (93 mg, 0.2 mmol) and base (82 mg, 0.4 mmol) are premixed and azeotroped 3 times with toluene. To a 25 mL flame-dried flask under argon is added freshly distilled $CH_2Cl_2$. The azeotroped reactants are dissolved in 10 mL $CH_2Cl_2$ and added to the flask, which is then cooled to –78° C. After 10 minutes triflic anhydride (33.6 μL, 0.2 mmol) is added. The reaction is followed by TLC (30% ethyl acetate-petroleum ether). The TLC indicates that the nucleophile 31a has reacted completely while the silyl ether 31b remains unreacted. The reaction is gradually warmed to –60° C. over a period of two hours and then quenched by pouring into a saturated solution of $NaHCO_3$. The resulting mixture is extracted with $CH_2Cl_2$ (3×15 mL), dried over anhydrous $Na_2SO_4$ and concentrated under vacuum. Flash chromatography (30% ethyl acetate-petroleum ether) gives the disaccharide 33 as a white crystalline solid (85 mg, 60% yield). $R_f$=0.4 (30% ethyl acetate-petroleum ether). $^1$H NMR ($CDCl_3$, 270 MHz) δ8.1–7.9 (m, 6H), 7.6–7.1 (m, 14H), 5.80 (d, J=5.28 Hz, 1H, H-1), 5.74 (m, 1H, H-3), 5.47 (m, 1H, H-3'), 5.43 (d, J=1.98 Hz, H-4), 5.21 (d, J=1.98 Hz, H-4'), 4.54 (q, J=6.27 Hz, H-5), 4.39 (q, J=6.60 Hz, 1H, H-5'), 4.20 (d, J=2.31 Hz, 1H, H-an), 2.96 (dt, J=5.61, 12.87 Hz, 1H, H-2'), 2.20 (m, 3H), 1.28 (d, J=6.60 Hz, 3H, $CH_3$), 0.47 (d, J=6.27 Hz, 3H, $CH_3$). $^{13}$C NMR ($CDCl_3$, 67.5 MHz) δ165.95, 165.90, 165.69, 134.94, 133.42, 133.11, 132.92, 131.06, 129.91, 129.88, 129.85, 129.76, 129.69, 129.57, 128.91, 128.58, 128.42, 128.23, 127.01, 98.93, 83.79, 75.33, 70.34, 70.10, 67.60, 67.53, 65.71, 30.98, 30.21, 17.41, 16.08.

6.2. Synthesis of the A Ring

The synthesis of the A ring starts with L-fucose, and is accomplished in six steps with an overall yield of 60%, according to the scheme, below.

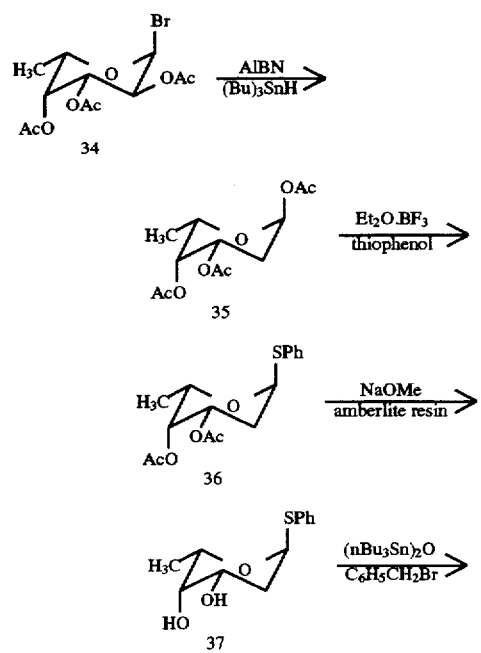

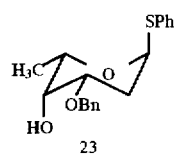

6.2.1. 1,3,4-O-Tri-O-acetyl-2,6-dideoxy-α-L-galactopyranoside (35)

To a solution of tetra-O-acetyl-fucose (5.0 g, 15.05 mmol) in 10 mL of glacial acetic acid is added 15 mL hydrobromic acid (30%) in a dropwise manner and the resulting solution stirred at room temperature. After two hours the reaction is complete. Work up is done under anhydrous conditions by pouring the reaction mixture into a flask containing 25 g of anhydrous sodium carbonate ($Na_2CO_3$) suspended in 200 mL of carbon tetrachloride. The resulting mixture is stirred at room temperature for 45 minutes and filtered. The procedure is repeated with the filtrate. The resulting solution is then concentrated under vacuum to afford crude bromide 34 (5.2 g, 80%). This is used without further purification in the next step.

To a two-liter three-necked flask, equipped with a reflux condenser and an addition funnel, is added one liter of freshly distilled benzene. The fucose bromide 34 (5.2 g, 12.17 mmol) is dissolved in benzene (15 mL) and added to the flask. The resulting mixture is heated to reflux. AIBN (200 mg, 1.21 mmol) is added to this solution. After 30 minutes the tributyl tin hydride (4.91 mL, 18.25 mmol) in benzene (100 mL) is added dropwise to the reaction mixture over a period of 16 hours via the addition funnel. At the end of this time, the reaction mixture is then cooled to room temperature and concentrated under vacuum. Flash chromatography (25% ethyl acetate-petroleum ether) affords the product 35 (2.5 g, 81%) as a crystalline white solid. $R_f$ (TLC)=0.3 (25% ethyl acetate-petroleum ether). $^1$H NMR ($CDCl_3$, 270 MHz) δ6.24 (d, J=2.64 Hz, 1H, H-1), 5.22 (m, 1H, H-3), 5.17 (t, J=0.66 Hz, 1H, H-4), 4.11 (q, J=5.94 Hz, 1H, H-5), 2.13 (s, 3H), 2.06 (s, 3H), 1.97 (s, 3H), 1.10 (d, J=6.6 Hz, 3H, $CH_3$); $^{13}$C NMR ($CDCl_3$, 67.9 MHz) δ170.13, 169.65, 168.82, 91.51, 68.87, 66.93, 65.86, 28.37, 20.60, 20.42, 16.14, 16.01.

6.2.2. Phenyl-3,4-O-diacetyl-2,6-dideoxy-1-thio-α-L-galactopyranose (36)

Compound 35 (2.5 g, 9.11 mmol) and thiophenol (1.12 mL, 10.94 mmol) are dissolved in dichloromethane (100 mL) and cooled under argon to –78° C. $Et_2O.BF_3$ (5.6 mL, 45.5 mmol) is added dropwise via a syringe to the solution. The reaction is kept at low temperature for one hour and then gradually warmed to 0° C. and quenched by pouring it into saturated aqueous $NaHCO_3$. The resulting biphasic mixture is extracted with $CH_2Cl_2$ (3×50 mL); the organic layers are combined, dried over anhydrous $Na_2SO_4$ and concentrated. Flash chromatography of the crude material (15% ethyl acetate-petroleum ether) gives the sulfide 36 as a white solid (2.1 g, 71% yield). $R_f$ (TLC)=0.3 (15% ethyl acetate-petroleum ether). $^1$H NMR ($CDCl_3$, 270 MHz) δ7.5–7.2 (m, 5H), 5.73 (d, J=5.61 Hz, 1H, H-1), 5.29 (m, 1H, H-3), 5.23 (bs, 1H, H-3), 4.56 (q, J=6.6 Hz, 1H, H-5), 2.49 (dt, J=5.94, 12.87 Hz, 1H, H-2$_{ax}$), 2.38 (s, 3H, OAc), 2.06 (m, 1H, H-2$_{eq}$), 1.99 (s, 3H, OAc), 1.13 (d, J=6.6 Hz, 3H, $CH_3$). $^{13}$C NMR for α anomer of sulfide ($CDCl_3$, 67.9 MHz) δ170.51, 169.87, 159.54, 134.33, 124.54, 114.54, 84.58, 69.69, 67.18, 65.51, 55.22, 20.79, 20.60, 16.34.

6.2.3. Phenyl-2,6-dideoxy-1-thio-α-L-galactopyranoside (37)

The compound 36 (2.1 g, 6.48 mmol) is dissolved in methanol (50 mL) and sodium methoxide (420 mg, 7.78 mmol) is added to the solution. The reaction is stirred at room temperature for one hour. A TLC (40% ethyl acetate-petroleum ether) taken at the end of this time indicates that the reaction is complete. The solution is neutralized with amberlite IR (120) plus ion-exchange resin (1.0 g). The solution is filtered through a fritted funnel, washed with ethyl acetate and concentrated to afford the diol 37. This compound is used without further purification in the next step.

6.2.4. Phenyl-3-O-benzyl-2,6-dideoxy-1-thio-α-L-galactopyranoside (23)

A solution of 37 (923 mg, 3.84 mmol) and dibutyl tin oxide (956 mg, 3.84 mmol) in benzene (60 mL) is heated to reflux in a flask fitted with a Dean-Stark apparatus. After 15 hours the reaction mixture is cooled to room temperature and tetrabutylammonium bromide (1.24 g, 3.84 mmol) is added followed by benzyl bromide (5 mL, 8.4 mmol). The resulting mixture is refluxed further for two hours, then cooled to room temperature and concentrated under vacuum. Flash chromatography on the crude product (15% ethyl acetate-petroleum ether) affords the sulfide 23 as a white solid (1.10 g, 90% yield). $R_f$ (TLC)=0.5 (30% ethyl acetate-petroleum ether). $^1$H NMR (CDCl$_3$, 270 MHz) α anomer δ7.40–7.41 (m, 10H), 5.57 (d, J=5.61 Hz, 1H, H-1), 4.49 (s, 2H), 4.18 (q, J=6.6 Hz, 1H, H-5), 3.74 (m, 1H, H-3), 3.70 (d, J=3.63 Hz, 1H, H-4), 2.20(dt, J=5.61, 12.5 Hz, 1H, H-2), 2.14 (bs, 1H, OH), 1.95 (m, 1H, H-2'), 1.17 (d, J=6.6 Hz, 3H, CH$_3$). $^{13}$C NMR (CDCl$_3$, 67.9 MHz) δ137.72, 135.20, 130.76, 128.84, 128.52, 127.92, 127.67, 126.83, 83.93, 73.514, 70.13, 68.46, 66.83, 30.67, 16.61. HRMS m/e 330.1290 (M$^+$) calcd for C$_{19}$H$_{22}$O$_3$S 330.1290.

6.3. Synthesis of the B ring

The synthesis of the B ring is accomplished as follows:

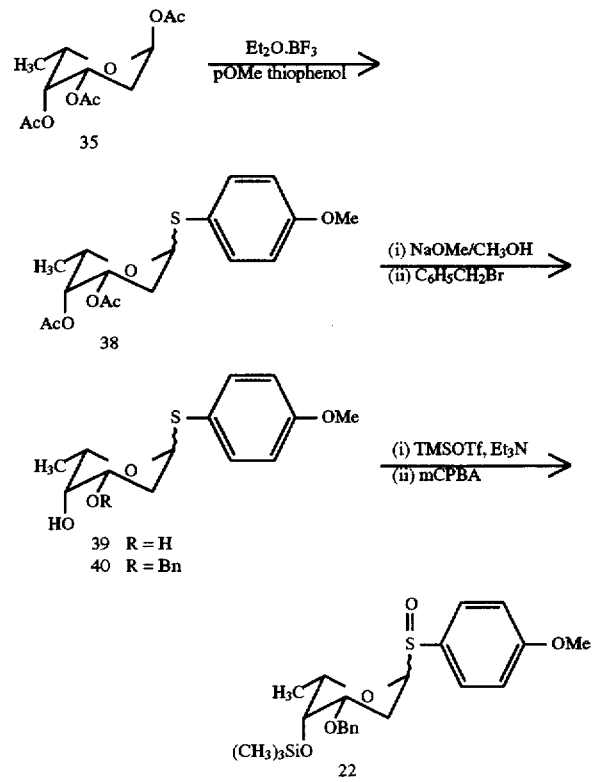

6.3.1. 4-Methoxyphenyl-3,4-O-diacetyl-2,6-dideoxy-1-thio-L-galactopyranoside (38)

To a solution of 35 (1.95 g, 7.14 mmol) in distilled dichloromethane (100 mL) is added 4-methoxy thiophenol (1 mL, 8.56 mmol) and the resulting mixture is cooled to −78° C. To this is added Et$_2$O.BF$_3$ (4.4 mL, 35.70 mmol) dropwise. The reaction mixture is stirred a low temperature for ½ hour then gradually warmed to −30° C. and quenched by pouring into a saturated solution of NaHCO$_3$. The resulting mixture is extracted with CH$_2$Cl$_2$ (3×30 mL). The organic extracts are combined, dried over anhydrous Na$_2$SO$_4$, filtered and concentrated under vacuum. The crude product is purified by flash chromatography (20% ethyl acetate-petroleum ether) to afford the sulfide 38 (2.12 g, 85%). $R_f$ (TLC)=0.4 (20% ethyl acetate-petroleum ether). $^1$H NMR (CDCl$_3$, 270 MHz) δ7.40 (d, 2H), 6.8 (d, 2H), 5.51 (d, J=5.61 Hz, 1H, H-1), 5.26 (m, 1H, H-3), 5.19 (t, J=2.97 Hz, 1H, H-4), 4.54 (q, J=6.6 Hz, 1H, H-5), 3.77 (s, OCH$_3$), 2.32(dt, J=5.61, 12.80 Hz, 1H, H-2), 2.12 (s, 3H), 2.02 (dt, J=4.62, 12.80 Hz, 1H, H-2'), 1.98 (s, 3H), 1.07 (d, J=6.6 Hz, 3H, CH$_3$); $^{13}$C NMR (CDCl$_3$, 67.9 MHz) δ170.51, 169.87, 159.54, 134.33, 124.54, 114.54, 84.58, 69.69, 67.18, 65.51, 55.22, 30.24, 20.79, 20.60, 16.34; HRMS m/e 354.1140 (M$^+$), calcd for C$_{17}$H$_{22}$O$_6$S 354.1137.

6.3.2. 4-Methoxyphenyl-2,6-dideoxy-1-thio-L-galactopyranoside (39)

To a solution of 38 (1.0 g, 2.82 mmol) in methanol (100 mL) is added sodium methoxide (183 mg, 3.38 mmol). The reaction mixture is stirred at room temperature for two hours and then neutralized by adding Amberlite resin (1.0 g). The reaction mixture is filtered and concentrated under vacuum to afford the diol 39 (760 mg, 100%). This is used without further purification in the next step. $R_f$ (TLC)=0.1 (50% ethyl acetate-petroleum ether). $^1$H NMR (CDCl$_3$, 270 MHz) α anomer δ7.35 (d, 2H), 6.80 (d, 2H), 5.41 (d, J=5.28 Hz, 1H, H-1), 4.41 (q, J=6.6 Hz, 1H, H-5), 3.95 (m, 1H, H-3), 3.76(s, OCH$_3$), 3.65 (d, J=2.64 Hz, 1H, H-4), 2.01(m, 2H, H-2, 2'), 1.23 (d, J=6.6 Hz, 3H, CH$_3$).

6.3.3. 4-Methoxyphenyl-3-O-benzyl-2,6-dideoxy-1-thio-L-galactopyranoside (40)

A solution of 39 (2.13 g, 7.90 mmol) and dibutyl tin oxide (1.96 g, 7.90 mmol) in benzene (200 mL) is heated to reflux in a flask fitted with a Dean-Stark apparatus. After 15 hours the reaction mixture is cooled to room temperature and to it is added tetrabutyl ammonium bromide (2.54 g, 7.90 mmol) followed by benzyl bromide (2.82 mL, 23.7 mmol). The resulting mixture is refluxed further for two hours, then cooled to room temperature and concentrated under vacuum. Flash chromatography on the crude product (15% ethyl acetate-petroleum ether) affords the sulfide 40 as an oil (2.5 g, 88%). $R_f$ (TLC)=0.25 (20% ethyl acetate-petroleum ether). $^1$H NMR (CDCl$_3$, 270 MHz) δ7.5–7.25 (m, 7H), 6.81 (d, J=8.91 Hz, 2H), 5.49 (d, J=5.61 Hz, 1H, H-1), 4.6 (s, 2H), 4.32 (q, J=6.59 Hz, 1H, H-5), 3.85 (m, 1H, H-3), 3.82 (d, J=3.3 Hz, 1H, H-4), 3.77 (s, OCH$_3$), 2.25 (dt, J=5.94, 12.8 Hz, 1H, H-2), 2.2 (bs, OH), 1.72 (m, 1H, H-2'), 1.27 (d, J=6.59 Hz, 3H, CH$_3$). $^{13}$C NMR (CDCl$_3$, 67.9 MHz) δ159.25, 137.66, 134.03, 128.33, 127.70, 127.52, 124.98, 114.37, 84.81, 73.40, 69.87, 68.35, 66.55, 55.06, 30.24, 16.47. HRMS m/e 360.1385 (M$^+$), calcd for C$_{23}$H$_{24}$O$_4$S 360.1396.

6.3.4. 4-Methoxyphenyl-3-O-benzyl-2,6-dideoxy-1-thio-4-O-(trimethyl-silyl)-L-galactopyranoside (41)

A solution of 40 (1.4 g, 3.88 mmol) and triethylamine (1.62 mL, 11.64 mmol) in dichloromethane (100 mL) is cooled to −78° C. under argon. To this solution is added TMSOTf (825 μl, 4.27 mmol) dropwise. The reaction is stirred at low temperature for 30 minutes and then quenched by pouring it into a solution of saturated NaHCO$_3$. The resulting mixture is extracted with CH$_2$Cl$_2$ (3×30 mL). The organic extracts are combined, dried over anhydrous Na$_2$SO$_4$ and concentrated. Flash chromatography (10% ethyl acetate-petroleum ether) afforded the product 41 (1.3 g, 83%) as an oil. $R_f$ (TLC)=0.85 (15% ethyl acetate-petroleum ether). $^1$H NMR (CDCl$_3$, 270 MHz) δ7.32 (d, J=8.58 Hz, 2H), 7.28 (m, 5H), 6.79 (d, J=8.91 Hz, 2H), 5.52 (d, J=5.28 Hz, 1H, H-1), 4.55 (d, J=0.99 Hz, 2H), 4.21 (q, J=6.60 Hz, 1H, H-5), 3.79 (bs, 1H, H-4), 3.76 (s, OCH$_3$), 3.66 (m, 1H, H-3), 2.32 (dt, J=5.61, 12.54 Hz, 1H, H-2), 1.97 (m, 1H, H-2'), 1.14 (d, J=6.59 Hz, 3H, CH$_3$), 0.11 (s, 9H, TMS). $^{13}$C NMR (CDCl$_3$, 67.9 MHz) δ138.19, 133.67, 128.15, 127.46, 127.39, 125.55, 114.32, 85.16, 74.26, 71.05, 70.16, 67.76, 55.03, 30.11, 16.99, 0.5. HRMS m/e 432.1808 (M$^+$), calcd for C$_{23}$H$_{32}$O$_4$SSi 432.1790

6.3.5. 4-Methoxyphenyl-3-O-benzyl-2,6-dideoxy-1-sulfinyl-4-O-(trimethyl-silyl)-L-galactopyranoside (22)

To a solution of the sulfide 41 (402 mg, 0.93 mmol) in dichloromethane (60 mL) is added an excess of solid sodium bicarbonate (1.0 g) and the resulting mixture cooled to –78° C. To this suspension is added mCPBA (193 mg, 1.11 mmol) and the resulting mixture is stirred at low temperature for 30 minutes. The temperature of the reaction mixture is gradually raised to 0° C. over a period of one hour and then quenched by pouring into a saturated solution of NaHCO$_3$. The resulting mixture is extracted with CH$_2$Cl$_2$ (3×30 mL) the organic layers combined, dried over anhydrous Na$_2$SO$_4$ and concentrated under vacuum. Flash chromatography (30% ethyl acetate-petroleum ether) affords the sulfoxide 22 (400 mg, 96%) as a white solid. $R_f$ (TLC)=0.4 (30% ethyl acetate-petroleum ether). $^1$H NMR (270 MHz, CDCl$_3$) δ7.51 (d, J=8.58 Hz, 2H), 7.4–7.2 (m, 5H), 6.97 (d, J=8.58 Hz, 2H), 4.62 (d, J$_{AB}$=11.87 Hz, 1H), 4.55 (d, J$_{AB}$=11.88 Hz, 1H), 4.47 (d, J=5.27 Hz, 1H, H-1), 4.02 (q, J=6.6 Hz, 1H, H-5), 3.91 (m, 1H, H-3), 3.84 (bs, 1H, H-4), 3.83 (s, OCH$_3$), 2.63 (dd, J=4.62, 13.86 Hz, 1H, H-2), 2.02 (dt, J=5.61, 13.85 Hz, 1H, H-2'), 1.12 (d, J=6.26 Hz, 3H, CH$_3$), 0.09 (s, 9H, TMS).

6.4. Synthesis of the C ring

The C ring is prepared as follows:

6.4.1. Methyl-4-O-acetyl-2,3,6-trideoxy-L-erythro-hexopyranoside (44)

To a solution of Methyl-4-O-acetyl-2,3,6-trideoxy-L-erythro-hex-2-enopyranoside 43 (2.0 g, 0.01 mmol) (See, Martin et al. Carbohydr. Res. 1983, 115, 21) in benzene is added the catalyst Pd(OH)$_2$/C (200 mg) and the resulting suspension is shaken in a Parr shaker under H$_2$ (50 psi). After two hours the reaction mixture is filtered through Celite and concentrated under vacuum to give 44 (2.0 g, 100% yield). This is used in the next step without further purification. $R_f$ (TLC)=0.5 (20% ethyl acetate-petroleum ether). $^1$H NMR (CDCl$_3$, 270 MHz) δ4.63 (s, 1H, H-4), 4.52 (bt, 1H, H-1), 4.32 (q, J=6.27 Hz, 1H, H-5), 3.22 (s, OCH$_3$), 2.02 (s, 3H, OAc), 1.9 (m, 1H, H-3'), 1.85–1.65 (m, 3H, H-2, 2', 3), 1.02 (d, J=6.27 Hz, 3H, CH$_3$). $^{13}$C NMR (CDCl$_3$, 67.9 MHz) δ169.14, 96.78, 72.96, 65.85, 53.70, 28.68, 23.69, 20.29, 17.34. HRMS m/e 187.0971 (M$^+$) calcd for C$_9$H$_{15}$O$_4$ 187.0970.

6.4.2. Phenyl-4-O-acetyl-1-thio-2,3,5-trideoxy-β-L-arabino-hexapyranoside (45a)

To a solution of 44 (2.3 g, 12.23 mmol) and thiophenol (1.5 mL, 14.67 mmol) in dichloromethane (100 mL) cooled to –78° C. is added BF$_3$.OEt$_2$ (4.5 mL, 36.69 mmol) dropwise. The reaction is stirred at low temperature for 30 minutes, gradually warmed to –60° C., and quenched by pouring into a saturated solution of NaHCO$_3$. The resulting mixture is then extracted with CH$_2$Cl$_2$ (3×25 mL); the organic layers are combined, dried over anhydrous Na$_2$SO$_4$ and concentrated under vacuum. Flash chromatography (15% ethyl acetate-petroleum ether) affords the sulfide 45a (3.0 g, 92%) as a white solid. $R_f$ (TLC)=0.4 (15% ethyl acetate-petroleum ether). $^1$H NMR (270 MHz, CDCl$_3$) δ7.55–7.2 (m, 5H), 5.52 (d, J=4.95 Hz, 1H, H-4), 4.59 (dt, J=4.62, 10.23 Hz, 1H, H-1), 4.30 (m, 1H, H-5), 2.2–2.1 (m, 2H, H-3, 3'), 2.09 (s, 3H, OAc), 1.9–1.75 (m, 2H, H-2, 2'), 1.17 (d, J=5.95 Hz, 3H, CH$_3$). HRMS m/e 266.0970 (M$^+$) calcd for C$_{14}$H$_{18}$O$_3$S 266.0977.

6.4.3. Phenyl-4-O-hydroxy-1-thio-2,3,5-trideoxy-β-L-arabino-hexapyranoside (45b)

To a solution of 45a (3.0 g, 11.27 mmol) in methanol (100 mL) is added sodium methoxide (365 mg, 6.76 mmol). The reaction mixture is stirred at room temperature for two hours and then neutralized by adding Amberlite resin (2.0 g) and stirred for 15 minutes. The reaction mixture is filtered and concentrated under vacuum to afford the alcohol 45b (2.52 g, 100%). This is used without further purification in the

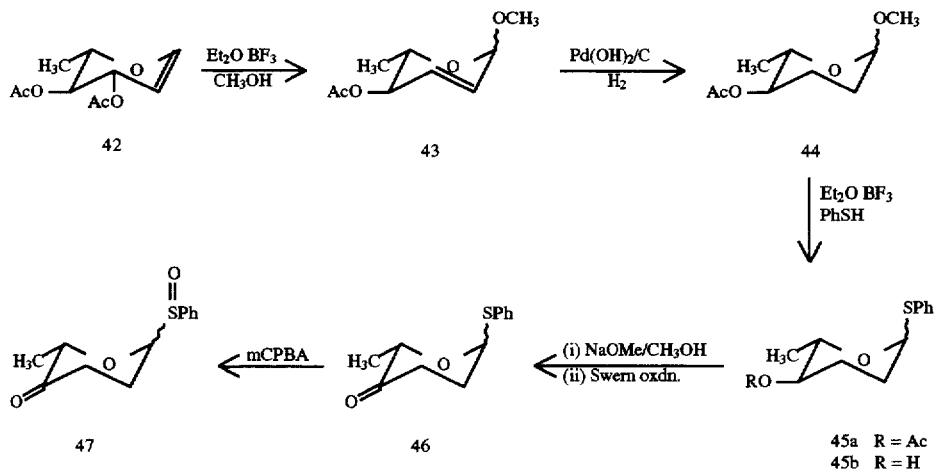

next step. $R_f$ (TLC)=0.2 (25% ethyl acetate-petroleum ether). $^1$H NMR (270 MHz, CDCl$_3$) δ7.5–7.2 (m, 5H), 5.49 (d, J=4.62 Hz, 1H, H-1), 4.1 (m, 1H, H-4), 3.3 (m, 1H, H-5), 2.2–1.6 (m, 4H, H-2, 2',3, 3'), 1.2 (d, J=5.49 Hz, 1H, CH$_3$).

6.4.4. Oxidation to Keto Sulfide (46)

A solution of oxalyl chloride (5.5 mL, 11.16 mmol) in dichloromethane (150 mL) is treated with DMSO (1.5 mL, 22 mmol) at –78° C. After 10 minutes a solution of the alcohol 45b (2.27 g, 10.15 mmol) in dichloromethane (15 mL) and triethylamine (7 mL, 50.75 mmol) is added to the reaction mixture. The reaction mixture is stirred at low temperature for 30 minutes, then warmed to 0° C. and quenched by pouring it into a solution of NaHCO$_3$. The resulting mixture is extracted with CH$_2$Cl$_2$ (3×30 mL); the organic layers combined, dried over anhydrous Na$_2$SO$_4$ and concentrated under vacuum. Flash chromatography (15% ethyl acetate-petroleum ether) afforded the ketone 46 (2.20 g, 97%) as a pale yellow oil. R$_f$ (TLC)=0.35 (15% ethyl acetate-petroleum ether). $^1$H NMR (CDCl$_3$, 500 MHz) δ7.65–7.20 (m, 5H), 5.52 (t, J=6.59, 6.96 Hz, 1H, H-1), 4.49 (q, J=6.6 Hz, 1H, H-5), 2.65–2.40 (m, 3H, H-3, 3', 2), 1.93 (m, 1H, H-2'), 1.22 (d, J=6.59 Hz, 3H, CH$_3$). $^{13}$C NMR (CDCl$_3$, 67.9 MHz) δ209.58, 134.40, 131.49, 128.91, 127.35, 82.78, 71.54, 34.98, 28.85, 14.63. HRMS m/e 222.0718 (M$^+$) calcd for C$_{12}$H$_{14}$O$_2$S 222.0715.

6.4.5. Oxidation of Keto Sulfide to Sulfoxide (21)

To a solution of the sulfide 46 (418 mg, 1.88 mmol) in dichloromethane (40 mL) is added an excess of solid sodium bicarbonate (1.0 g) and the resulting mixture cooled to −78° C. To this solution is added mCPBA (455 mg, 2.63 mmol) and the reaction mixture stirred at low temperature for 30 minutes. The temperature of the reaction mixture is slowly raised to 0° C. and then quenched by pouring into a saturated solution of NaHCO$_3$. The resulting mixture is extracted with CH$_2$Cl$_2$ (3×30 mL); the organic layers are combined, dried over anhydrous Na$_2$SO$_4$ and concentrated under vacuum. Flash chromatography (40% ethyl acetate-petroleum ether) affords the sulfoxide 47 (380 mg, 85%) as a pale yellow oil. R$_f$ (TLC)=0.25 (40% ethyl acetate-petroleum ether). $^1$H NMR (CDCl$_3$, 500 MHz.) δ7.65–7.42 (m, 5H), 4.64 (t, J=5.93 Hz, 1H, H-1), 4.59 (q, 1H, H-5), 2.80–2.40 (m, 3H, H-3, 3', 2), 1.80 (m, 1H, H-2'), 1.29 (d, J=6.93 Hz, 3H, CH$_3$).

6.4.6. 3-O-Benzyl-2,6-dideoxy-4-O-(trimethylsilyl)-α-L-galactopyranosyl-(1→4)-phenyl-3-O-benzyl-2,6-dideoxy-1-thio-α-L-galactopyranoside The sulfoxide 22 (350 mg, 0.78 mmol) and nucleophile 23 (129 mg, 0.39 mmol) are premixed and azeotroped together three times with distilled toluene. Freshly distilled diethyl ether (9 mL) is added to a flame dried flask under argon and cooled to −78° C. The premixed reactants are dissolved in 6 mL of distilled dichloromethane and added to the flask. This is followed by the addition of Hunig's base (136 μL, 0.78 mmol). After stirring for 5 minutes triflic anhydride (65.6 μL, 0.19 mmol) is added to the reaction. The reaction is followed by TLC (10% ethyl acetate-petroleum ether). The reaction is warmed to −70° C. and quenched by pouring into a saturated NaHCO$_3$ solution. The resulting solution is extracted with CH$_2$Cl$_2$ (3×15 mL); the organic layers are combined and dried over anhydrous Na$_2$SO$_4$. The solution is concentrated under vacuum and purified by flash chromatography (5% ethyl acetate-petroleum ether) to give the product disaccharide as an oil (95 mg, 40% yield). R$_f$ (TLC)=0.8 (10% ethyl acetate-petroleum ether). $^1$H NMR (CDCl$_3$, 270 MHz) δ7.45–7.10 (m, 10H), 5.68 (d, J=5.28 Hz, 1H), 5.07 (bs, 1H), 4.67 (d, J$_{AB}$=12.54 Hz, 1H), 4.55 (d, J$_{AB}$=12.54 Hz, 1H), 4.53 (s, 2H), 4.23 (q, J=6.60 Hz, 1H), 4.17 (q, J=6.60 Hz, 1H), 3.85 (d, J=2.64 Hz, 1H), 3.73 (m, 2H), 3.68 (d, J=1.32 Hz, 1H), 2.33 (dt, J=6.93, 12.54 Hz, 1H), 2.02 (m, 1H), 1.19 (d, J=6.60 Hz, 3H), 0.89 (d, J=6.27 Hz, 3H), 0.06 (s, 9H). $^{13}$C NMR (CDCl$_3$, 67.9 MHz) δ138.63, 138.29, 135.32, 130.93, 128.90, 128.85, 128.59, 128.49, 128.20, 127.61, 127.55, 127.32, 126.89, 84.39, 74.26, 73.79, 73.76, 71.14, 70.25, 68.10, 67.43, 31.72, 29.54, 17.37, 17.23, 16.65, 0.63.

6.4.7. 3-O-Benzyl-2,6-dideoxy-α-L-galactopyranosyl-(1→4)-phenyl-3-O-benzyl-2,6-dideoxy-1-thio-α-L-galactopyranoside (48)

The product disaccharide from the previous section (70 mg, 0.11 mmol) is dissolved in freshly distilled THF. Tetrabutylammonium fluoride (500 μL, 5 mmol) is added to the solution. The reaction is complete in one hour. Work up is done by pouring the reaction mixture in NaHCO$_3$ solution and extracting (3×15 mL) with THF. The organic layers are combined and concentrated under vacuum. The product 48 is used without further purification in the next step. R$_f$ (TLC)=0.4 (25% ethyl acetate-petroleum ether). $^1$H NMR (CDCl$_3$, 270 MHz) δ7.5–7.2 (m, 10H), 5.69 (d, J=5.27 Hz, 1H), 5.03 (d, J=2.97 Hz, 1H), 4.66 (d, J$_{AB}$=12.54 Hz, 1H), 4.60 (d, J$_{AB}$=11.55 Hz, 1H), 4.56 (d, J$_{AB}$=11.22 Hz, 1H), 4.50 (d, J$_{AB}$=11.22 Hz, 1H), 4.27 (q, J=6.93 Hz, 1H), 4.22 (q, J=6.60 Hz, 1H), 3.90 (m, 1H,), 3.86 (bd, J=2.31 Hz, 1H), 3.74 (m, 1H), 3.72 (bs, 1H), 2.12 (bs, OH), 1.91 (m, 2H), 1.19 (d, J=6.60 Hz, 3H), 1.01 (d, J=6.60 Hz, 3H). $^{13}$C NMR (CDCl$_3$, 67.9 MHz) δ138.10, 138.01, 135.22, 130.86, 128.83, 128.46, 128.40, 127.79, 127.67, 127.63, 127.39, 126.88, 99.15, 84.30, 74.84, 73.64, 73.21, 70.34, 70.07, 68.30, 67.97, 65.86, 31.65, 29.83, 17.34, 16.62.

6.4.8. ABC trisaccharide (49)

The sulfoxide 21 (60 mg, 0.22 mmol) and the nucleophile 48 (61 mg, 0.11 mmol) are premixed and azeotroped three times with distilled toluene. Freshly distilled dichloromethane (1 mL) and diethylether (5 mL) are added to a flame dried flask and cooled under argon to −78° C. The premixed nucleophile and sulfoxide are dissolved in dichloromethane (3 mL) and added to the cooled flask. This is followed by the addition of Hunig's base (40 μL, 0.22 mmol). After five minutes the triflic anhydride (18.5 μL, 0.11 mmol) is added to the flask. The reaction is stirred for two hours between −78° and −70° C. The reaction is then quenched by pouring into a solution of saturated NaHCO$_3$. The reaction mixture is extracted with CH$_2$Cl$_2$ (3×15 mL), the organic layers combined and dried over anhydrous Na$_2$SO$_4$. The solution is concentrated under vacuum and purified by flash chromatography (20% ethyl acetate-petroleum ether) to give the trisaccharide 49 (18 mg, 25% yield).

6.5. One Step Synthesis of the Ciclamycin 0 Trisaccharide

The sulfoxides 21 (417 mg, 1.812 mmol, 3.0 eq), 22 (541 mg, 1.2 mmol, 2.0 eq) and the nucleophile 23 (165 mg, 0.604 mmol, 1.0 eq) are premixed and thoroughly dried by azeotroping three times with distilled toluene. The starting materials are then dissolved in freshly distilled CH$_2$Cl$_2$ (20 mL) and added to a 50 mL flame dried flask under argon. To this reaction mixture is added 20 mL of freshly distilled Et$_2$O followed by methyl propiolate (9.06 mmol, 15 eq). The flask is cooled to −78° C. using an acetone/dry ice bath. After 5 minutes, triflic acid (5.3 μL, 0.06 mmol, 0.05 eq) is added to the reaction mixture dropwise. The reaction is followed by TLC (20% ethyl acetate-petroleum ether). The reaction mixture is slowly warmed to −70° C. over a period of half an hour and then quenched by pouring it into a saturated solution of NaHCO$_3$ (30 mL). The resulting biphasic mixture is extracted with CH$_2$Cl$_2$ (3×15 mL). The combined organic extracts are dried over anhydrous Na$_2$SO$_4$ and concentrated. Flash chromatography (20% ethyl acetate-petroleum ether) provides the trisaccharide 49 (99 mg 25%) as a colourless oil. R$_f$ (TLC)=0.2 (20% ethyl acetate-petroleum ether). $^1$H NMR (CDCl$_3$, 500 MHz.) δ7.45–7.20 (m, 15H), 5.67 (d, J=4.85 Hz, 1H), 5.07 (d, J=2.64 Hz, 1H), 4.98 (t, J=3.36 Hz, 1H), 4.66 (d, J=1.32 Hz, 1H), 4.19 (q, J=6.6 Hz, 1H), 3.88 (m, 1H), 3.84 (bs, 1H), 3.73 (m, 1H), 2.52 (m, 1H), 2.28 (m,1H), 2.23–2.02 (m, 2H), 1.19 (d, J=6.60 Hz, 3H), 0.90 (d, J=5.27 Hz, 3H), 0.88 (d, J=6.60 Hz, 3H). $^{13}$C NMR (CDCl$_3$, 67.9 MHz) δ211.13, 139.13, 138.94, 135.74, 131.74, 131.63, 129.20, 128.69, 128.60, 127.87, 127.81, 127.72, 127.69, 127.31, 99.57, 98.22, 84.80, 75.79, 74.98, 74.69, 74.19, 73.40, 71.85, 70.45, 68.44, 67.59, 34.25, 31.88, 31.09, 29.89, 17.48, 17.35, 14.93.

6.5.1. Ciclamycin trisaccharide (49a)

The sulfoxides 21 (190 mg, 0.8 mmol, 3.5 eq), 22a (230 mg, 0.48 mmol, 2.0 eq) and the nucleophile 23a (85 mg, 0.24 mmol, 1.0 eq) are premixed and thoroughly dried by azeotroping three times with distilled toluene. The starting materials are then dissolved in freshly distilled $CH_2Cl_2$ (5 mL) and added to a 25 mL flame dried flask under argon. To this reaction mixture is added 5 mL of freshly distilled $Et_2O$ followed by methyl propiolate (4.8 mmol, 20 eq). The flask is cooled to −78° C. using an acetone/dry ice bath. After 5 minutes, triflic acid (5.3 µL, 0.06 mmol, 0.05 eq) is added to the reaction mixture dropwise. The reaction is followed by TLC (20% ethyl acetate-petroleum ether). The reaction mixture is slowly warmed to −70° C. over a period of half an hour and then quenched by pouring it into a saturated solution of $NaHCO_3$ (30 mL). The resulting biphasic mixture is extracted with $CH_2Cl_2$ (3×15 mL). The combined organic extracts are dried over anhydrous $Na_2SO_4$ and concentrated. Flash chromatography (30% ethyl acetate-petroleum ether) provides the trisaccharide 49a (35 mg 20%) as a colourless oil. $R_f$ (TLC)=0.3 (30% ethyl acetate-petroleum ether).

6.5.2. Oxidation of the sulfide to the sulfoxide

The trisaccharide sulfide 49a (20 mg, 0.027 mmol) is dissolved in 15 mL of freshly distilled $CH_2Cl_2$ taken in a 25 mL flask. To this solution is added solid $NaHCO_3$ (500 mg) followed by mCPBA (7.8 mg, 0.045 mmol). The reaction is followed by TLC (40% ethyl acetate-petroleum ether). The reaction mixture is slowly warmed to −60° C. and quenched by pouring into a saturated solution of $NaHCO_3$. The resulting biphasic mixture is extracted with $CH_2Cl_2$ (3×10 mL); the organic layers are combined and dried over anhydrous $Na_2SO_4$. The trisaccharide sulfoxide 50a (PMB-protected trisaccharide sulfoxide) is obtained as an oil (19 mg). It is used without purification for glycosylation.

6.5.3. Degradation of Marcellomycin to Obtain the Aglycone ε-Pyrromycinone

Marcellomycin, 53, an anthracycline antibiotic isolated from bohemic acid complex, has the same aglycone ε-pyrromycinone as ciclamycin (See, below). (The marcellomycin is a generous gift from Bristol-Myers Squibb Company.) The aglycone can be obtained by removing the marcellomycin trisaccharide by acid hydrolysis.

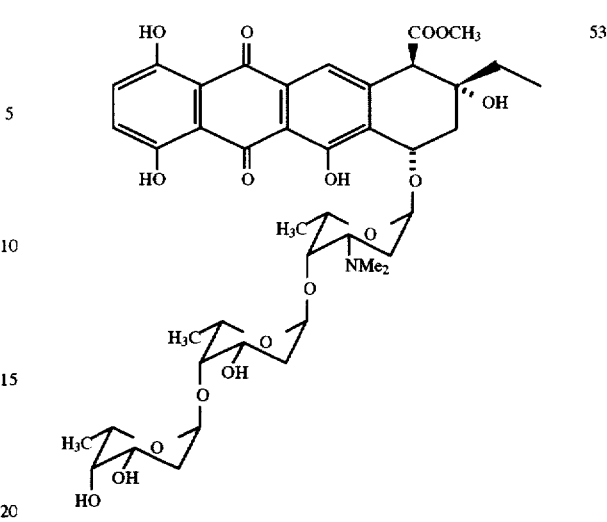

The drug (75 mg) is refluxed in methanolic HCl (25 mL, 0.1N) for two hours. At the end of this Marcellomycin (75 mg, 0.175 mmol) is dissolved in methanolic HCl (25 mL, 0.1N) and refluxed at 50° C. for two hours. At the end of this time the reaction mixture is concentrated under vacuum and purified by preparative thin layer chromatography (15% methanol-chloroform). The aglycone ε-pyrromycinone is isolated as a bright red solid (21 mg, 54% yield).

6.5.4. Coupling of the trisaccharide to the aglycone

The PMB-protected trisaccharide sulfoxide 50a (19 mg, 25 µmol) ε-pyrromycinone (6 mg, 14.15 µmol) and stilbene (2.5 mg, 14 µmol) are premixed and azeotroped three times with distilled toluene. Freshly distilled ether (2 mL) is added to a 15 mL flame dried flask and cooled under argon to −78° C. The azeotroped reactants are dissolved in distilled dichloromethane (3 mL) and added to the flask. After 10 minutes, triflic anhydride (0.118 µl, 0.7 µmol) is added to the flask and the reaction followed by TLC (15% ethyl acetate-petroleum ether). The reaction mixture is gradually warmed to −50° C. and quenched by pouring into a saturated solution of $NaHCO_3$. The resulting mixture is extracted with dichloromethane (3×5 mL); the organic layers are combined and dried over anhydrous $Na_2SO_4$. The solution is concentrated under vacuum and purified by flash chromatography (15% ether-methylene chloride followed by 10% methanol-methylene chloride). The product is isolated as a bright red solid (0.75 mg, 16% yield).

6.6. One-Pot Synthesis Of Homopolymers Of Different Lengths

Figure 2:
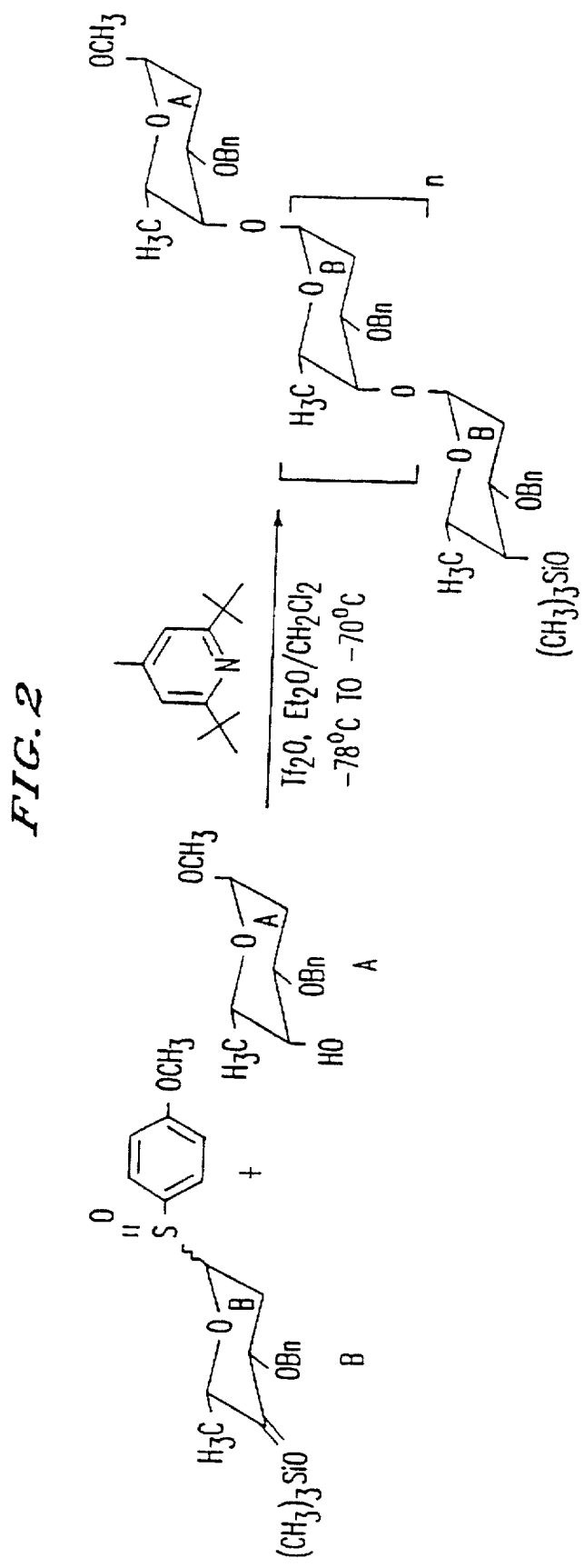
FIG. 2 illustrates a process of forming homopolymers of 2-deoxy fucose in one step.

FIG. 2 illustrates another aspect of the present invention which allows the synthesis of "homopolymers" of different lengths. Hence, alpha-linked homopolymers of 2-deoxy fucose with different length distributions are produced by mixing in separate flasks different ratios of the bifunctional sulfoxide 4-methoxy phenyl-3-O-benzyl-4-O-trimethylsilyl-2-deoxy-1-sulfinyl-α-L-fucopyranoside, B, with the monofunctional glycosyl acceptor methyl-3-O-benzyl-2-deoxy-α-L-fucopyranoside, A, and the base 2,6-di-t-butyl-4-methylpyridine (2 equivalents relative to sulfoxide). The Table, below, indicates the reactant ratio that is used for each of the experiments 6.6.1–6.6.5. The mixtures are first dried thoroughly by azeotropic distillation from toluene (preferably, three times, as above).

The mixtures are then each dissolved in 2.5–5 mL anhydrous methylene chloride and added to separate 25 mL flame dried flasks under argon. To each reaction mixture is added an equal volume of freshly distilled diethyl ether. The flasks are next cooled to –78° C. using an acetone/dry ice bath. After 5 minutes, a methylene chloride solution of triflic anhydride (1.0 equiv relative to B) is added dropwise to the reaction mixtures. The reactions are monitored by thin layer chromatography using 15% ethyl acetate/petroleum ether as the eluant.

After warming to –70° C. over a period of about half an hour, the reaction mixtures are quenched with saturated solution of NaHCO$_3$ (approximately 30 mL each). Each of the resulting biphasic mixtures is extracted with methylene chloride (3×15 mL). The organic extracts are combined, dried over anhydrous Na$_2$SO$_4$ and concentrated. Flash chromatography (1:5 ethyl acetate/petroleum ether) is used to isolate the glycosylated products from each reaction. The length distribution of "homopolymers" produced is found to vary with the ratio of A to B and also with the total concentration of reactants in the reaction mixture, as shown in the Table III, below.

TABLE III

Relative Amounts of Various "Homopolymers" Produced As A Function Of Molar Ratios Of Reactant And Total Concentration

| Entry | A:B (ratio) | [A + B] (mmol/mL) | AB (%) | AB$^2$ (%) | AB$^3$ (%) | AB$^4$ (%) | AB$^5$ (%) |
|---|---|---|---|---|---|---|---|
| 6.6.1 | 1:1 | 0.088 | 40 | — | — | — | — |
| 6.6.2 | 1:2 | 0.083 | 45 | 20 | — | — | — |
| 6.6.3 | 1:3 | 0.096 | 60 | 30 | 8.7 | — | — |
| 6.6.4 | 1:5 | 0.050 | 50 | 30 | 8.0 | 1.5 | — |
| 6.6.5 | 1:3 | 0.233 | 30 | 40 | 17 | 8.4 | 1.7 |

AB = A—B ($^1$H NMR, given below)
AB$^2$ = A—B—B ($^1$H NMR, given below)
AB$^3$ = A—B—B—B ($^1$H NMR, given below)
AB$^4$ = A—B—B—B—B ($^1$H NMR, given below)
AB$^5$ = A—B—B—B—B—B ($^1$H NMR, given below)

More specifically, the results of the reaction described above, may be obtained by premixing the sulfoxide (320 mgs, 0.714 mmol, 3.0 eq), nucleophile (60 mgs, 0.238 mmol, 1.0 eq) and base (147 mgs, 0.714 mmol, 3 eq). The resulting mixture is then dried by azeotropic distillation three times from toluene. The reactants are then dissolved in 2.5 ml of distilled CH$_2$Cl$_2$ and added to a 25 ml flame-dried flask under argon. The flask is then cooled to –78° C. and 2.5 ml of Et$_2$O is added to the reaction. (The concentration of the sulfoxide is approximately 0.144 mmol/ml.) After 10 min Tf$_2$O (1.5 eq, 0.357 mmol, 60 μl) is added. The reaction is maintained at –78° C. for ½ hour, then allowed to warm to –70° C. and stirred at this temperature for an additional ½ hour.

The reaction is quenched by pouring the reaction mixture into sat. NaHCO$_3$ solution, followed by extraction 3 times with CH$_2$Cl$_2$, drying over anhydrous Na$_2$SO$_4$ and concentration. Purification is accomplished by flash chromatography: 15% EA/PE; 20% EA/PE. The structures of the various oligosaccharides are supported by the proton NMR data (270 MHz, CDCl$_3$), in which the non-terminal B's are labeled X, X$_1$, or X$_2$, etc.:

AB disaccharide: $^1$H NMR δ5.08, bs, 1H, H1B; 4.81, d, 1H, H1A; 4.7–4.5, 4H benzyl methylenes; 4.2, q, 1H, H5B; 3.9–3.7, m, 5H, H3A, H4A, H4B, H3B, H5A; 3.3, s, 3H, methoxy; 1.8–2.1, 4H, H2A, H2B; 1.21, d, 3H, H6A (methyl); 0.9, d, 3H, H6B (methyl) ppm.

AXB trisaccharide: $^1$H NMR δ5.06, s, 1H, H1B; 5.01, s, 1H, H1X; 4.82, d, 1H, H1A; 4.75–4.45, m, 6H benzyl methylene; 4.21, q, 2H, H5X, H5B; 3.91–3.64, m, 7G, H3A, H3X, H3B, H5A, H4A, H4X, H4B; 3.29, s, 3H, A1 methoxy; 2.08–1.80, d, 3H, H6A; 1.23, d, 3H, H6A (methyl) δ0.90, 3d, 6H, H6X, H6B (methyls) ppm.

AX$_1$X$_2$B tetrasaccharide: $^1$H NMR δ5.27, d, 1H, H1B; 4.99, d, 2H, H1X$_1$, H1$_2$; 4.81, d, 1H, H1A; 4.72–4.45, m, BH benzyl methylenes; 4.2, m, 3H, H5X$_1$, H5$_2$, H5B; 3.90–3.62, m, 9H, H5A, H4A, H4X$_1$, H4X$_2$, H4B, H3A, H3X$_1$, H3X$_2$, H3B;3.29, s, 3H; 2.05–1.80, 8H, 2-deoxy, CH2A, CH2X$_1$, CH2X$_2$, CH2B; 1.22, d, 3H, H6A (methyl); 1.9–1.8, 9H, H6X$_1$, H6X$_2$, H6B (methyls) ppm.

AX$_1$X$_2$X$_3$B pentasaccharide: $^1$H NMR δ5.06, s, 1H, H1B; 4.95, s, 3H, H1X$_1$, H1X$_2$, HX; 4.79, 1H, s, H1A; 4.7–4.4, m, 10H, benzyl methylenes; 4.15, m, 4H, H5X$_1$, H5X$_2$, H5X$_3$, H5B; 3.3, s, 3H, A1 methoxy; 1.2, 3H, d, H6A (methyl); 0.85, 12H, m, H6X$_1$, H6X$_2$, H6X$_3$, H6B (methyls) ppm.

AX$_1$X$_2$X$_3$X$_4$B hexasaccharide: $^1$H NMR δ5.05, s, 1H, H1B; 4.98, s, 4H, HX$_1$, H1X$_2$, H1X$_3$, H1X$_4$; 4.7–4.4, 12H, benzyl methylenes; 4.2–4.1, 5H, H5X$_1$, H5X$_2$, H5X$_3$, H5X$_4$, H5B; 2.1–1.8, m, 12H, H2A, H2X$_1$, H2X$_2$, H2X$_3$, H2X$_4$, H2B; 1.2, d, 3H, H6A (methyl); 0.9–0.8, m, 15H, H6X$_1$, H6X$_2$, H6X$_3$, H6X$_4$, H6B (methyls) ppm.

6.7. Controlled Polymerization Reactions

According to another method of the present invention, a controlled polymerization reaction is performed as follows:

The sulfoxide 22 (260 mg, 0.58 mmol), nucleophile 53 (73 mg, 0.29 mmol), and base 2, 6-di-tert-butyl-4-methyl pyridine (118 mg, 0.58 mmol) are premixed and azeotroped three times with distilled toluene. To a 25 mL flame dried flask is added freshly distilled diethyl ether (5 mL) and cooled under argon to –78° C. The azeotroped reactants are dissolved in distilled dichloromethane (5 mL) and added to the flask. After 10 minutes triflic anhydride (48.5 μL, 0.29 mmol) is added to the flask. The reaction is stirred at –70° C. for 45 minutes and then quenched by pouring into a saturated solution of NaHCO$_3$. The resulting biphasic mixture is extracted with CH$_2$Cl$_2$ (3×15 mL); the organic layers are combined and dried over anhydrous Na$_2$SO$_4$. The solution is concentrated under vacuum and purified by flash chromatography (15% ethyl acetate-petroleum ether). The AB disaccharide 54 (70 mg, 45%) and the ABB trisaccharide 55 (40 mg, 20%) are isolated as oils. AB dissacharide: R$_f$ (TLC)=0.4 (15% ethyl acetate-petroleum ether). $^1$H NMR (CDCl$_3$, 270 MHz,) δ7.4–7.2 (m, 10H), 5.06 (bs, 1H, H$_{an}$), 4.81 (d, J=2.97 Hz, 1H, H-1'), 4.68 (d, J$_{AB}$=12.53 Hz, 1H), 4.54 (s, 2H), 4.50 (d, J$_{AB}$=10.89 Hz, 1H), 4.16 (q, J=6.26 Hz, 1H, H-5), 3.9 (m, 1H, H-3), 3.8 (s, 1H, H-4), 3.75 (q, J=5.94 Hz, 1H, H-5'), 3.70 (m, 1H, H-3'), 3.67 (d, J=1.65 Hz, 1H, H-4), 3.27 (s, 3H, OCH$_3$), 2.1 (m, 3H, H-2's). 1.8 (dd, J=4.62, 12.21 Hz, 1H, H-2$_{ax}$), 1.21 (d, J=6.6 Hz, 3H, CH$_3$), 0.9 (d, J=6.27 Hz, 3H, CH$_3$), 0.06 (s, 9H). $^{13}$C NMR (CDCl$_3$, 67.9 MHz) δ138.61, 128.24, 128.14, 127.57, 137.32, 127.27, 127.19, 99.27, 98.89, 74.17, 73.78, 72.91, 71.13, 70.22, 70.04, 67.28, 66.80, 54.67, 30.77, 29.51, 17.51, 17.21, 0.58.

6.8. One-Pot Synthesis Of Glycoconjugates With Potential DNA Binding Activity

The strategy for forming multiple glycosidic linkages in solution can be used to synthesize in the same reaction several glycoconjugates with potential DNA binding activity. Depending on the situation, the glycoconjugates can be separated and screened individually for DNA binding activity or they can be screened as mixtures. For example, a mixture of glycoconjugates, each comprised of a potential DNA intercalator and an oligosaccharide side chain, and differing one from another only in the length of the oligosaccharide side chain, are synthesized as in Example 6.6, but using a 4:1 ratio of bifunctional donor to glycosyl acceptor. Specifically, the 2-deoxy fucosyl sulfoxide derivative B (908 mg, 1.90 mmol), the glycosyl acceptor A (294 mg, 0.48 mmol), and 2,6-ditert-butyl-4-methyl pyridine (779 mg, 3.80 mmol) are combined, dried by azeotropic distillation three times from toluene and then dissolved in 10 mL of a 1:1 mixture of ether/methylene chloride (freshly distilled solvents). The solution is transferred to a flame dried flask under argon. The flask is cooled to −78° C. using an acetone/dry ice bath. After 5 minutes, 161.1 µL (0.96 mmol) triflic anhydride is added dropwise to the reaction mixture. The reaction is slowly warmed to −70° C. over a period of half an hour and then quenched by pouring into a saturated solution of NaHCO$_3$ (30 mL). The mixture is extracted with methylene chloride (3×15 mL). The combined organic extracts are dried over anhydrous Na$_2$SO$_4$, filtered, and the solvent removed under vacuum. The reaction is dissolved in 10 mL of wet methylene chloride and treated with excess dichlorodicyanoquinone (DDQ) at room temperature for 1 hour to remove the p-methoxy benzyl ether protecting groups. The solvent is then removed under vacuum and the components are separated by flash chromatography on silica gel.

Their relative affinities for DNA are evaluated to determine the preferred length of the oligosaccharide side chain. Affinity chromatography can be used to identify oligosaccharides that bind to particular receptors. For example, a mixture of compounds is passed over a column containing a solid support to which is attached a receptor of interest (or ligand, if the mobile phase contains a mixture of potential receptors). Compounds that bind to the receptor are retained on the column longer than compounds that do not. Compounds can be fractionated according to their affinity for the receptor.

Thus, receptors that bind carbohydrates can be attached to the solid support. Carbohydrate receptors may be comprised of DNA (double or single stranded), RNA, protein, oligosaccharides, or other molecules. Methods to attach nucleic acids, proteins, and oligosaccharides to solid supports for use in affinity chromatography have been described. See: (a) *Template Chromatography of Nucleic Acids and Proteins*, Schott, H. Marcel Dekker, Inc.: New York, 1984; (b) *Glycoconjugates: Composition, Structure and Function*, Allen, H. J.; Kisailus, E. C., Eds. Marcel Dekker: NY 1992 (and references therein). (NOTE: Retention times can also be used to quantitate affinities for single compounds passed down the affinity column.)

In another example, glycosyl acceptor A (FIG. 3) is premixed with 2,3-p-methoxy benzyl-4-trimethylsilyl rhamnosyl sulfoxide C (FIG. 3) and allowed to react under conditions (e.g., temperature, solvent, concentration, donor/acceptor ratio) identical to those described above. After workup and removal of the p-methoxy benzyl protecting groups with DDQ, as above, the mixture of glycoconjugates is separated by flash chromatography on silica gel and the relative affinities of the different compounds for DNA are determined. The glycoconjugates produced by the above-described methods are compared with respect to their abilities to bind to DNA. In this way, the effects of different sugars on DNA binding affinity can be compared to identify preferred sugars.

Figure 3A:
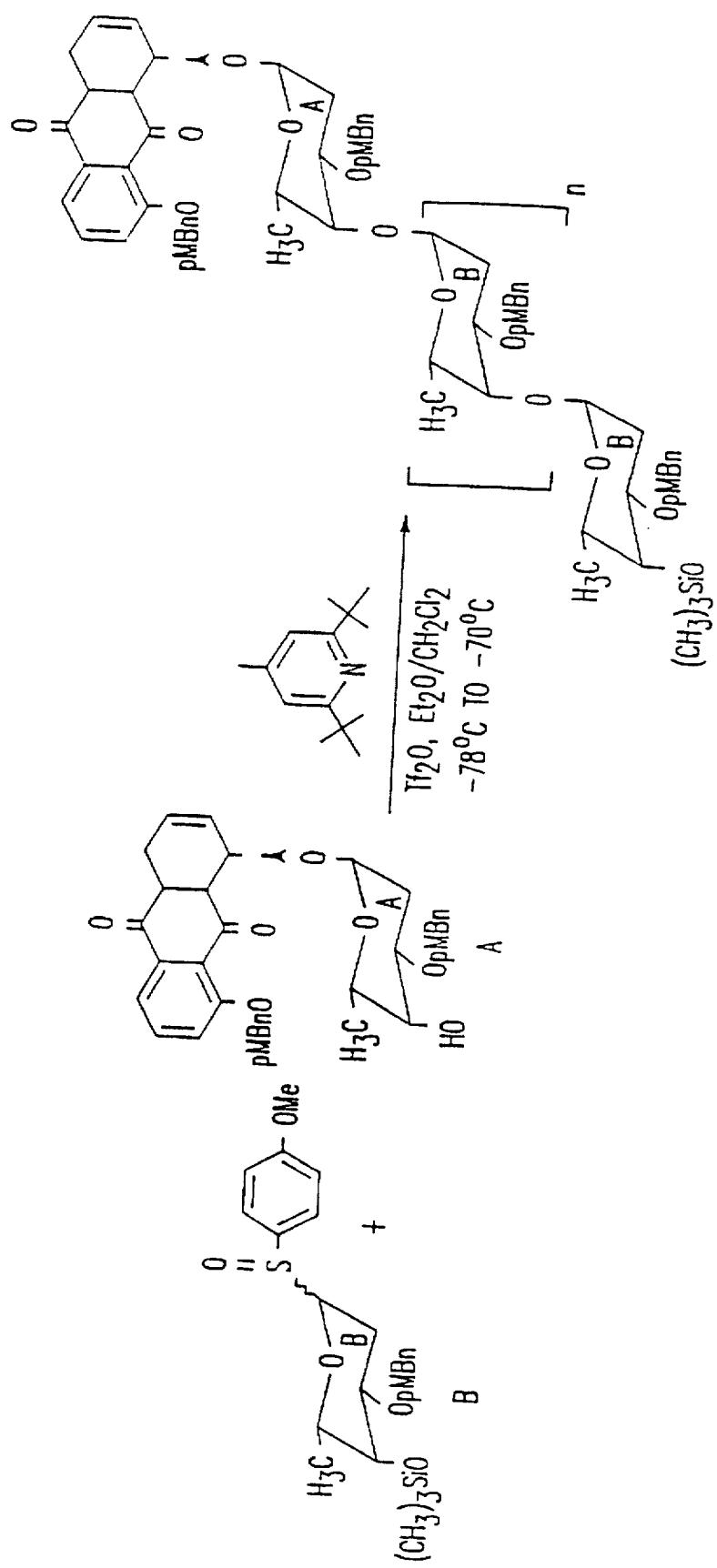
FIGS. 3A and 3B illustrate a process of synthesizing mixtures of glycoconjugates having biological activity, including potential DNA binding activity. The glycoconjugates so produced can subsequently be screened (e.g., for DNA binding activity) to evaluate the preferred length and the preferred sugar residues of the oligosaccharide portion of the glycoconjugate based on the activity being tested.
Figure 3B:
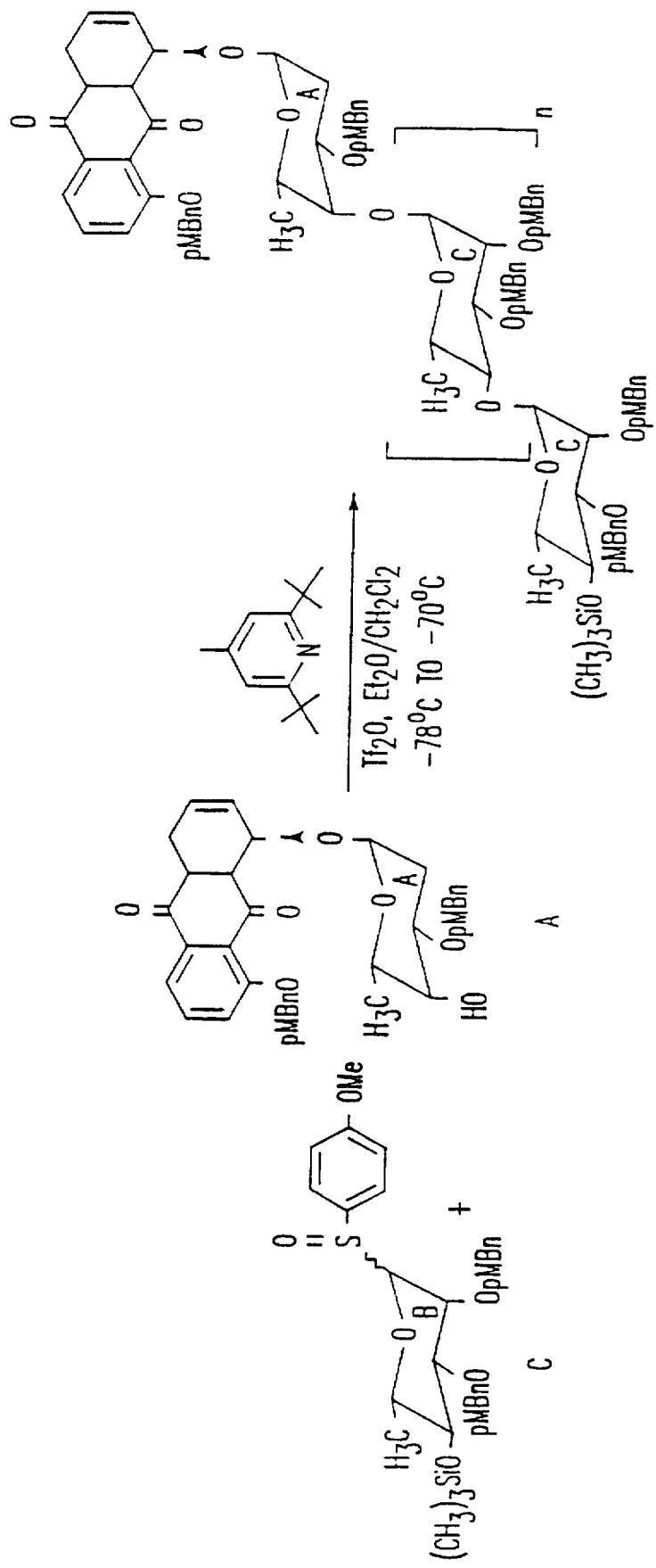

The glycosyl acceptor A in FIG. 3 is made by glycosylating a suitably protected juglone derivative (obtained by the procedures of Inhoffen et al. *Croatica Chem. Acta.* 1957, 29, 329; Trost et al. *J. Am. Chem. Soc.* 1977, 99, 8116; and Stork and Hagedorn *J. Am. Chem. Soc.* 1978, 100, 3609) with compound B (FIG. 3) using Tf$_2$O-Hunig's base CH$_2$Cl$_2$/ether (1:1) at low temperature. After a standard workup (including extraction, as described in the other Examples herein) and removal of solvent, the product mixture is dissolved in methylene chloride and treated with excess tetrabutylammonium fluoride at 0° C. The solvent is then removed in vacuo and the product isolated by flash chromatography.

The general process described above may also be applied to the synthesis of mixtures of glycoconjugates containing several different sugars. In this case, two or more bifunctional glycosyl donors are used in the reaction. After deprotection, the resulting mixture of glycoconjugates can be screened for DNA binding activity by passing it down a DNA affinity column. Compounds can be fractionated according to their retention times on the affinity column. Compounds with long retention times can be isolated and identified using standard methods for structure elucidation.

6.9. Additional Embodiments Illustrating the Catalytic Glycosylation Method

The following examples relate to glycosylation methods mediated by catalytic amounts of sulfonic acid, including reactions involving silylated glycosyl acceptors.

6.9.1. 1,2,3,4-Tetra-O-acetyl-6-O-(trimethylsilyl)-D-glucopyranose (2b)

The following procedure is typical for all silylations of the nucleophile. The alcohol 2a (600 mg, 1.85 mmol, 1.0 eq) and triethyl amine (775 µL, 3.43 mmol, 3.0 eq) are dissolved in distilled methylene chloride and cooled to −78° C. under argon. Trimethyl silyl triflate (394 µL, 2.03 mmol, 1.1 eq) is added to the reaction mixture. The reaction is followed by TLC. After 30 minutes the reaction is quenched by pouring into a saturated solution of NaHCO$_3$. The resulting biphasic mixture is extracted with CH$_2$Cl$_2$ (3×25 mL). The organic layers are combined and dried over anhydrous Na$_2$SO$_4$. Purification by flash chromatography affords the silyl ether 2b (700 mg, 90%) as a white solid. R$_f$(TLC)=0.6 (40% ethyl acetate-petroleum ether). $^1$H NMR (270 MHz, CDCl$_3$) δ5.69 (d, J=8.25 Hz, 1H, H-1), 5.25 (t, J=9.24 Hz, H, 1H-3), 5.15 (t, J=9.24 Hz, 1H, H-4), 5.12 (t, J=8.24, 9.25 Hz, 1H, H-2), 3.8–3.7 (m, 3H, H-5, H-6,6'), 2.1–2 (m, 12H, OAc), 0.5 (s, 9H, TMS).

6.9.2. α,α-1,1-Dimer of Perbenzylated Glucose (5)

The perbenzylated glucose 1,1-dimer is identified, as follows: R$_f$(TLC)=0.8 (25% ethyl acetate-petroleum ether). $^1$H NMR (270 MHz, CDCl$_3$) δ7.4–7.1 (m, 40H), 5.19 (d, J=3.30 Hz, 1H), 5.16 (d, J$_{AB}$=11.55 Hz, 1H), 5.02 (d, J$_{AB}$=10.89 Hz, 1H), 4.97 (d, J$_{AB}$=12.21 Hz, 1H), 4.90 (d, J$_{AB}$=10.89 Hz, 1H), 4.89 (d, J$_{AB}$=10.89 Hz, 1H), 4.83 (d, J$_{AB}$=10.89 Hz, 1H), 4.82 (d, J=3.30 Hz, 1H$_{an}$), 4.81 (d, J$_{AB}$=11.54 Hz, 1H), 4.75 (d, J$_{AB}$=12.21 Hz, 1H), 4.69 (d, J$_{AB}$=12.21 Hz, 1H), 4.59 (bs, 2H), 4.55 (d, J$_{AB}$=11.88 Hz, 1H), 4.52 (d, J$_{AB}$=10.88 Hz, 1H), 4.49 (bs, 2H), 4.34 (d, J$_{AB}$=12.21 Hz, 1H), 4.21 (m, 1H), 4.15 (t, J=9.24, 9.47 Hz, 1H), 3.82 (t, J=9.24, 9.9, Hz, 1H), 3.7–3.45 (m, 7H).

6.9.3. Synthesis of 3,4,6-Tri-O-benzyl-2-deoxy-D-glucopyranosyl-(1→6)-1,2,3,4-tetra-O-acetyl-β-D-glucopyranose (7)

The following procedure is typical of all glycosylation reactions run under acid catalyzed conditions using TfOH: The sulfoxide 6 (140 mg, 0.258 mmol, 1.5 eq) and the nucleophile 2 (69 mg, 0.172 mmol, 1.0 eq.) are premixed and thoroughly dried by "azeotroping" 3 times with distilled toluene. The starting materials are then dissolved in 8 mL of freshly distilled CH$_2$Cl$_2$ and added to a 25 mL flame dried flask under argon. The flask is cooled to −78° C. using an acetone-dry ice bath. Methyl propiolate (230 µL, 2.58 mmol, 15 eq) is added to this solution as a sulfenic acid scavenger.

After the solution is stirred at −78° C. for 2 minutes, triflic acid (1.1 μL, 0.0129 mmol, 0.05 eq) is added. The reaction is followed by TLC (25% ethyl acetate-petroleum ether). The reaction mixture is slowly warmed to −30° C. over a period of 1 hour, and then quenched by pouring it into a saturated solution of NaHCO$_3$ (25 mL). The resulting mixture is extracted with CH$_2$Cl$_2$ (3×15 mL). The organic extracts are combined, dried with anhydrous Na$_2$SO$_4$, and concentrated. Flash chromatography (25% ethyl acetate-petroleum ether) provides the disaccharide 7 (116 mg, 88%) as a white solid. R$_f$(TLC)=0.3 (25% ethyl acetate-petroleum ether). $^1$H NMR (270 MHz, CDCl$_3$) δ7.4–7.2 (m, 15H), 5.75 (d, J=8.25 Hz, 1H, H-a), 5.32 (t, J=9.24 Hz, 1H, H-c), 5.21 (t, J=9.57 Hz, 1H, H-d), 5.20 (t, J=8.25, 9.24 Hz, 1H, H-b), 4.99 (d, J=2.64 Hz, 1H, H-1), 4.95 (d, JAB=11.21 Hz, 1H), 4.71 (bs, 2H), 4.66 (d, J$_{AB}$=11.87 Hz, 1H), 4.59 (d, J$_{AB}$=11.22 Hz, 1H), 4.55 (d, J$_{AB}$=11.88 Hz, 1H), 4.10 (m, 1H, H-e), 3.85–3.50 (m, 7H), 2.36 (dd, J=4.94, 12.86 Hz, 1H), 2.15 (s, 3H), 2.10 (s, 3H), 2.05 (s, 3H), 1.95 (s, 3H), 1.70 (m, 1H).

6.9.4. Methyl-6-deoxy-3,4-isopropyl-idene-2-O-(trimethylsilyl)-β-D-galactopyranoside (8)

The compound 8 is synthesized from D-fucose by the following three-step sequence: (i) MeOH, H$^+$; (ii) acetone, H$_3$PO$_4$ (cat); (iii) TMSOTf, Et$_3$N, CH$_2$Cl$_2$, −78° C. Rf (TLC)=0.5 (15% ethyl acetate-petroleum ether). $^1$H NMR (CDCl$_3$, 270 MHz) δ4.03 (d, J=8.24 Hz, 1H, H-1), 3.98 (dd, J=5.28, 7.26 Hz, 1H), 3.97 (dd, J=5.40, 1.98 Hz, 1H), 3.84 (dq, J=1.98, 6.6 Hz, 1H, H-5), 3.49 (s, 3H, OCH$_3$), 3.47 (dd, J=7.59, 5.49 Hz, 1H), 1.48 (s, 3H, CH$_3$), 1.38 (d, J=6.6 Hz, 3H, CH$_3$) 1.31 (s, 3H, CH$_3$), 0.5 (s, 9H, TMS). $^{13}$C NMR (CDCl$_3$, 67.9 MHz) δ109.38, 103.70, 80.52, 76.48, 74.45, 68.58, 56.64, 28.02, 26.34, 16.49, 0.31.

6.9.5. 3,4,6-Tri-O-benzyl-2-deoxy-D-glucopyranosyl-α-(1→2)-methyl-6-deoxy-3,4-isopropyl-idene-β-D-galactopyranoside (9)

R$_f$ (TLC)=0.5 (25% ethyl acetate-petroleum ether). $^1$H NMR (CDCl$_3$, 270 MHz) α anomer δ7.4–7.15 (m, 15H), 5.30 (d, J=2.97 Hz, 1H), 4.86 (d, J$_{AB}$=10.89 Hz, 1H), 4.64 (d, J=1.65 Hz, 2H), 4.62 (d, J$_{AB}$=12.20 Hz, 1H), 4.53 (d, J$_{AB}$=10.89 Hz, 1H), 4.45 (d, J$_{AB}$=12.20 Hz, 1H), 4.06 (d, J=8.25 Hz, 1H), 3.70 (t, J=9.56 Hz, 1H), 3.46 (s, OCH$_3$), 2.02 (ddd, J=0.99, 4.95, 12.87 Hz, 1H), 1.65 (dt, J=3.62, 12.87 Hz, 1H), 1.40 (s, CH$_3$), 1.36 (d, J=6.6 Hz, 3H), 1.24 (s, 3H). $^{13}$C NMR (CDCl$_3$, 67.9 MHz) δ138.91, 138.83, 138.32, 128.28, 128.23, 127.92, 127.79, 127.45, 127.42, 127.38, 109.35, 103.95, 97.45, 78.39, 78.20, 77.70, 76.31, 76.12, 74.95, 73.45, 71.73, 70.53, 68.73, 68.48, 56.58, 35.47, 28.08, 26.34, 16.49.

6.9.6. Phenyl-4-O-acetyl-2,3,6-trideoxy-1-sulfinyl-α-L-erythro-hexopyranoside (10)

Compound 10 is synthesized from L-rhamnal in 3 steps. a) H$_2$ (1 atm), Pd(OH)$_2$/C, C$_6$H$_6$; b) BF$_3$.OEt$_2$, thiophenol, CH$_2$Cl$_2$, −78° C. to −60° C.; and c) mCPBA, CH$_2$Cl$_2$, −78° C. to −60° C. R$_f$ (TLC)=0.4 (25% ethyl acetate-petroleum ether). $^1$H NMR (CDCl$_3$, 270 MHz) β anomer (sulfide) δ7.5–7.2 (m, 5H), 5.54 (d, J=4.95 Hz, H-4), 4.81 (dd, J=1.98, 12.1 Hz, 1H, H-1), 4.6 (m, 2H, H-3, 3'), 4.3 (m, 1H, H-5), 2.2 (m, 2H, H2,2'), 2.1 (s, 3H, OAc), 1.19 (d, J=5.94 Hz, 3H, CH$_3$). $^{13}$C NMR (CDCl$_3$, 67.9 MHz) β anomer (sulfide) δ169.80, 130.98, 130.73, 128.58, 128.49, 83.79, 67.15, 29.95, 25.34, 20.82, 18.00, 17.44.

6.9.7. 4-O-Acetyl-2,3,6-trideoxy-L-erythro-hexopyranosyl-α-(1→6)-1,2,3,4-tetra-O-acetyl-β-D-glucopyranose (11)

R$_f$ (TLC)=0.3 (25% ethyl acetate-petroleum ether). $^1$H NMR (CDCl$_3$, 270 MHz) α anomer δ5.63 (d, J=7.92 Hz, 1H), 5.20 (t, J=9.24 Hz, 1H), 5.19 (t, J=9.24, 9.57 Hz, 1H), 5.09 (d, J=7.91 Hz, 1H), 5.03 (t, J=9.57 Hz, 1H), 4.61 (dd, J=1.98, 8.58 Hz, 1H), 4.33 (ddd, J=4.61, 10.23, 10.23 Hz, 1H), 3.94 (dd, J=3.96, 11.22 Hz, 1H), 3.71 (m, 1H), 3.56 (dd, J=2.96, 11.22 Hz, 1H), 2.05 (s, 3H), 1.99 (s, 3H), 1.98 (s, 3H), 1.96 (s, 3H), 1.95 (s, 3H), 1.11 (d, J=6.59 Hz, 3H). $^{13}$C NMR (CDCl$_3$, 67.9 MHz) δ170.19, 170.12, 169.18, 169.15, 168.95, 100.85, 91.79, 73.03, 72.96, 70.34, 68.60, 66.01, 29.54, 26.88, 21.07, 20.76, 20.64, 20.54, 20.50, 18.01, 17.72.

6.9.8. Phenyl-3,4-bis-O-(4-methoxy-benzoyl)-1-sulfinyl-D-digitoxose (13)

Compound 13 is synthesized from digitoxose by the following three-step sequence: (i) POMeC$_6$H$_4$COCl, pyridine; (ii) thiophenol, Et$_2$O.BF$_3$, CH$_2$Cl$_2$; (iii) mCPBA. R$_f$ (TLC)=0.2 (40% ethyl acetate-petroleum ether). $^1$H NMR (CDCl$_3$, 270 MHz) α anomer (sulfoxide) δ8.09 (d, J=8.91 Hz, 2H), 7.87 (d, J=9.24 Hz, 2H), 7.70 (m, 2H), 7.55 (m, 3H), 6.94 (d, J=8.90 Hz, 2H), 6.85 (d, J=8.91 Hz, 2H), 5.84 (q, J=3.31 Hz, 1H), 5.10 (dd, J=2.63, 2.97, 1H), 5.04 (m, 1H), 4.49 (dd, J=1.64, 5.13 Hz, 1H), 3.83 (s, 3H, OCH$_3$), 3.82 (s, 3H, OCH$_3$), 1.28 (d, J=5.95 Hz, 3H).

6.9.9. Phenyl-3,4-O-(4-methoxy-benzoyl)-β-D-digitoxosyl-(O)-N-hydroxyethyl carbamate (14)

R$_f$ (TLC)=0.45 (cc anomer, 40% ethyl acetate-petroleum ether). $^1$H NMR (CDCl$_3$, 270 MHz) α anomer δ8.03 (d, J=8.91 Hz, 2H), 7.79 (d, J=9.24 Hz, 2H), 6.88 (d, J=9.24 Hz, 2H), 6.77 (d, J=9.01 Hz, 2H), 5.60 (q, 1H), 5.12 (d, J=4.62 Hz, 1H), 4.95 (dd, J=2.97, 10.23 Hz, 1H), 4.78 (m, 1H), 4.18 (q, 2H), 4.17 (m, 1H), 3.84 (s, OCH$_3$), 3.79 (s, OCH$_3$), 2.37 (dd, J=3.3, 15.51 Hz, 1H), 2.19 (m, 1H), 1.26 (t, J=6.93 Hz, 3H), 1.25 (d, J=6.27 Hz, 3H). $^{13}$C NMR (CDCl$_3$, 67.9 MHz) δ165.48, 165.17, 163.53, 163.45, 157.42, 131.97, 131.75, 122.65, 121.92, 113.62, 113.59, 100.69, 100.61, 72.21, 65.90, 63.65, 62.08, 55.40, 32.04, 17.53, 14.44 R$_f$ (TLC)= 0.5 (β anomer, 40% ethyl acetate-petroleum ether). $^1$H NMR (CDCl$_3$, 270 MHz) β anomer δ7.92 (d, J=8.91 Hz, 2H), 7.78 (d, J=8.91 Hz, 2H), 6.89 (d, J=8.91 Hz, 2H), 6.77 (d, J=9.24 Hz, 2H), 5.74 (q, 1H), 5.23 (dd, J=2.31, 9.23 Hz, 1H), 4.93 (dd, J=2.97, 9.23 Hz, 1H), 4.23 (q, 1H), 4.16 (q, 2H), 4.17 (m, 1H), 3.85 (s, OCH$_3$), 3.79 (s, OCH$_3$), 2.36 (m, 1H), 2.04 (m, 1H), 1.29 (d, J=6.27 Hz, 3H), 1.23 (t, J=6.93 Hz, 3H). $^{13}$C NMR (CDCl$_3$, 67.9 MHz) δ165.10, 164.91, 163.61, 163.55, 131.85, 122.18, 121.83, 113.74, 113.59, 101.77, 72.31, 69.21, 67.41, 62.19, 60.34, 55.44, 55.38, 33.29, 18.01, 14.38.

6.9.10. Phenyl-2,3-O-benzoyl-6-deoxy-1-thio-β-L-galactopyranoside (15)

The compound 15 is synthesized from L-fucose by the following four-step sequence: (i) Ac$_2$O, pyridine; (ii) thiophenol, Et$_2$O.BF$_3$; (iii) NaOMe, CH$_3$OH, amberlite H$^+$ resin; (iv) C$_6$H$_5$COCl, DMAP. R$_f$ (TLC)=0.6 (40% ethyl acetate-petroleum ether). $^1$H NMR (CDCl$_3$, 270 MHz) δ8.0–7.9 (m, 4H), 7.55–7.2 (m, 1H), 5.64 (t, J=9.89 Hz, 1H), 5.27 (dd, J=2.97, 9.9 Hz, 1H), 4.86 (d, J=9.9 Hz, 1H), 4.09 (d, J=2.97 Hz, 1H), 3.87 (q, J=6.27 Hz, 1H), 1.40 (d, J=6.27 Hz, 3H).

6.9.11. Phenyl-3,4-O-acetyl-2,6-dideoxy-1-sulfinyl-L-galactopyranoside (16)

Compound 16 is prepared from 1,3,4-tri-O-acetyl-2-deoxy-α-L-fucose by the following two-step sequence: (i) thiophenol, Et$_2$O.BF$_3$; and (ii) mCPBA. R$_f$ (TLC for a sulfide)=0.3 (15% ethyl acetate-petroleum ether). $^1$H NMR (CDCl$_3$, 270 MHz) a sulfide δ7.5–7.2 (m, 5H), 5.73 (d, J=5.61 Hz, 1H, H-1), 5.29 (m, 1H, H-3), 5.23 (bs, 1H, H-3), 4.56 (q, J=6.6 Hz, 1H, H-5), 2.49 (dt, J=5.94, 12.87 Hz, 1H, H-2$_{ax}$), 2.38 (s, 3H, OAc), 2.06 (m, 1H, H-2$_{eq}$), 1.99 (s, 3H, OAc), 1.13 (d, J=6.6 Hz, 3H, CH$_3$). $^{13}$C NMR a sulfide (CDCl₃, 67.9 MHz) δ170.51, 169.87, 159.54, 134.33, 124.54, 114.54, 84.58, 69.69, 67.18, 65.51, 55.22, 20.79, 20.60, 16.34. $R_f$ (TLC for a sulfoxide)=0.25 (30% ethyl acetate-petroleum ether). ¹H NMR α anomer sulfoxide (CDCl₃, 270 MHz) δ7.6–7.3 (m, 5H), 5.43 (m, 1H), 5.26 (bd, J=2.64 Hz, 1H), 4.52 (d, J=5.61 Hz, 1H), 4.32 (q, J=6.6 Hz, 1H), 2.47 (dd, J=5.28, 14.18 Hz, 1H), 2.14 (dt, J=5.61, 14.19 Hz, 1H), 2.10 (s, 3H, OAc), 1.98 (s, 3H, OAc), 1.12 (d, J=6.26 Hz, 3H).

6.9.12. 3,4-O-Acetyl-2,6-dideoxy-L-galactopyranosyl-α-(1→4)-phenyl-3,4-O-benzoyl-6-deoxy-1-thio-β-L-galactopyranoside (17)

$R_f$ (TLC)=0.4 (30% ethyl acetate-petroleum ether). ¹H NMR (CDCl₃, 270 MHz) δ7.9 (m, 4H), 7.55–7.25 (m, 1H), 5.55 (t, J=10.23 Hz, 1H), 5.20 (dd, J=2.96, 10.22 Hz, 1H), 5.12 (m, 1H), 5.02 (bd, J=1.98 Hz, 1H), 4.94 (bs, 1H), 4.84 (d, J=9.9 Hz, 1H), 4.15 (d, J=2.97 Hz, 1H), 3.96 (q, J=6.27 Hz, 1H), 3.86 (q, J=6.27 Hz, 1H), 2.04 (s, 3H), 2.0 (s, 3H), 1.94 (m, 2H), 1.35 (d, J=6.27 Hz, 3H), 0.33 (d, J=6.27 Hz, 3H). ¹³C NMR (CDCl₃, 67.9 MHz) δ170.44, 169.62, 166.05, 164.95, 133.51, 133.36, 133.01, 131.49, 129.78, 129.62, 129.12, 128.65, 128.44, 128.27, 128.18, 99.49, 85.42, 76.86, 75.27, 74.68, 69.56, 67.47, 66.50, 65.27, 29.70, 20.85, 20.56, 17.32, 15.77.

6.10. Synthesis Of A β-Linked Disaccharide On The Solid Phase

To a 10 mL solution of DMF containing 0.338 g (0.350 mmol) of 2,3,4-tribenzyl-6-tritylgalactose-1-p-hydroxy phenythioglycoside cesium acetate (X, FIG. 6) is added 0.356 g (0.385 mmol C1 equiv, 1,1 equiv) of Merrifield resin (BACHEM Bioscience). This mixture is agitated with a wrist action shaker for 24 h under argon atmosphere at 75° C. At this time, the polymer is poured into a tared coarse-fritted Gooch funnel and washed repeatedly with methanol and methylene chloride. The funnel is then dried for 4 h in a lyophilizer jar at 20 milliTorr. A mass change of 0.244 g is recorded, which is calculated to be 85% chemical yield with respect to the cesium salt.

The polymer in the coarse-fritted Gooch funnel is then treated by vacuum filtration at moderate flow rate with 40 mL of 10% trifluoroacetic acid (TFA) in methylene chloride until no yellow color is apparent in the filtrate. (The TFA is used to remove the trityl protecting groups.) The polymer is next washed repeatedly with methanol and methylene chloride. The funnel, together with the resin-linked nucleophile, is then dried for 4 h in a lyophilizer jar at 20 milliTorr before "massing". A mass change of 0.065 g is subsequently measured, which is calculated to be 83% chemical yield with respect to the cesium salt. The concentration of the resin-linked nucleophile (resin-X, FIG. 6) is then calculated to be 0.544 mmol/g.

200 mg (i.e., 0.11 mmol) of derivatized resin is lyophilized overnight in the reaction vessel and then purged for 1 hour with argon. The resin is then suspended in 5 mL CH₂Cl₂. 4 equivalents (0.44 mmol) of 2-pivaloyl-3,4-benzyl-6-p-methoxy benzyl galactosyl phenyl sulfoxide (Y, FIG. 6) and 6 equivalents (0.66 mmol) 2,6-di-t-butyl-4-methyl pyridine are dissolved in 5 mL methylene chloride and added by canula to the reactor vessel. The mixture is agitated gently by argon flow for 30 minutes at room temperature and then the reactor vessel is immersed in a cold bath and allowed to cool to –60° C. 2 equivalents (0.22 mmol) of triflic anhydride diluted one hundred fold (v/v) in methylene chloride are added slowly (over 15 minutes) to the reaction vessel. The resulting reaction mixture is gently agitated for 1 hour.

After the reaction is completed, as indicated by the Hg(II) hydrolysis method and TLC analysis, the solvent and unbound reagents are then drained from the reactor vessel, and the resin mixture is rinsed repeatedly with methanol followed by methylene chloride. Subsequently, the resin mixture is suspended in 15 mL of methylene chloride and then treated with excess Hg(OCOCF₃)₂ for 8 hours to cleave the glycosidic linkage to the resin. (Note: only 5 minutes is required to remove sufficient product from the resin to monitor the reaction by TLC analysis.) The solvent is allowed to drain from the resin. Additional solvent is then used to rinse the resin. The filtrates are then combined, extracted three times with water and concentrated by evaporation. The desired β-linked disaccharide is obtained by flash chromatography on silica gel. No α-linked disaccharide is isolated from the reaction.

Figure 6:
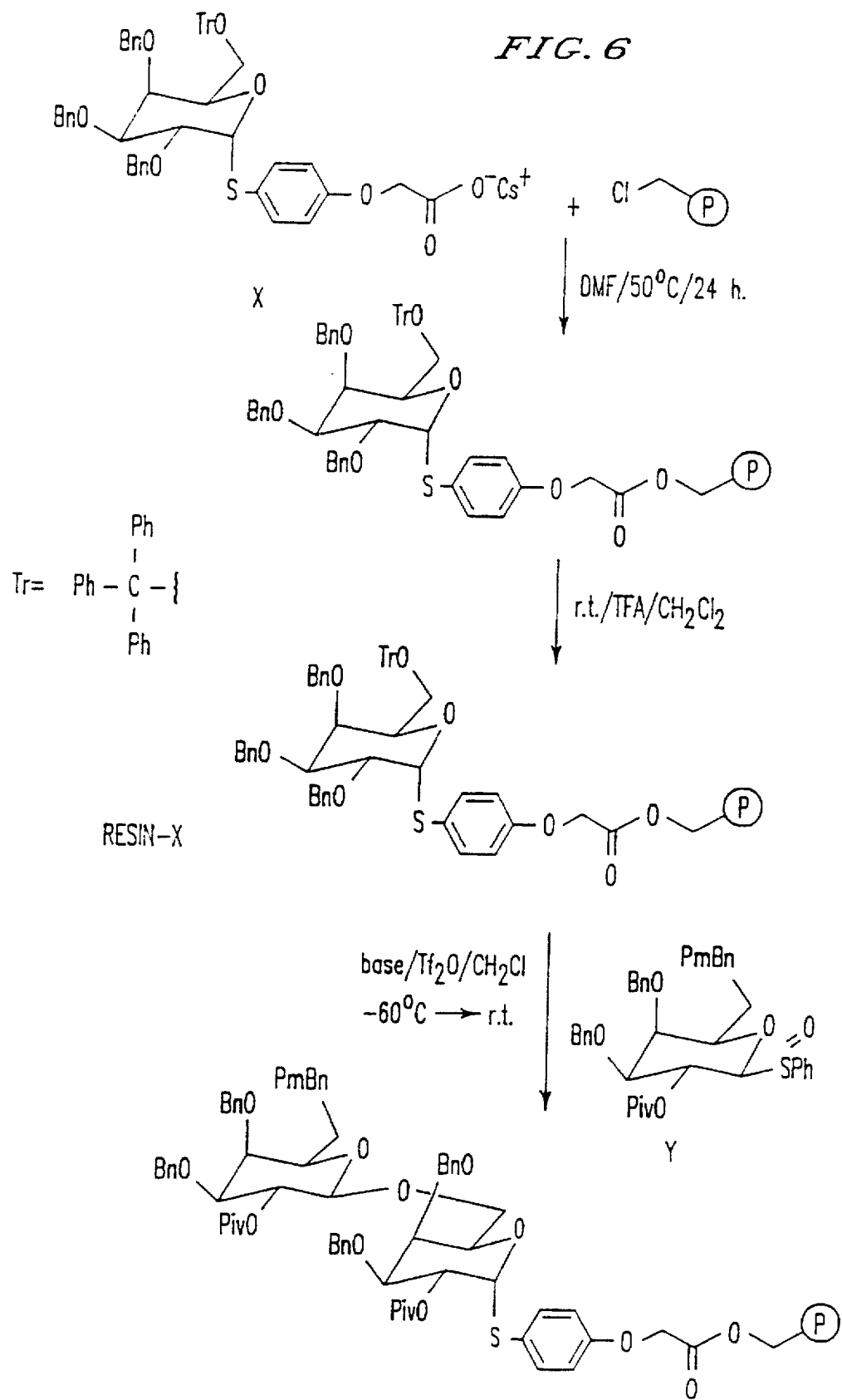
FIG. 6 illustrates the general scheme for synthesis of a β-linked disaccharide on the solid phase.

Thiosugar X in FIG. 6 is prepared from the readily available 1,6-anhydroglucose by treatment with benzyl bromide followed by acidic hydrolysis (H₂SO₄-THF-H₂O), tritylation (trityl chloride-pyridine) of the more reactive C6 primary alcohol, and treatment of the resulting lactol with disulfide XX and tri-n-butylphosphine (i.e., standard procedure for making thiophenyl glycosides from lactols). The disulfide XX is produced by reacting the disulfide of the readily available 4-hydroxythiophenol with α-bromomethyl acetate.

Disulfide XX

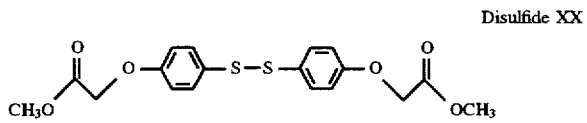

Sulfoxide Y in FIG. 6 is prepared from readily available penta-acetylated galactose using the following sequence of reagents: (1) BF₃/etherate-thiophenol; (2) hydroxide; (3) acetone-H⁺; (4) p-methoxy benzyl bromide-sodium hydride; (5) pivaloyl chloride; (6) mCPBA. Each step is well known in the art and the reactions are carried out under the standard conditions. (See, list of "Standard References" below in Section 6.15 the disclosures of which are incorporated by reference herein.).

The disaccharide produced from the reaction of X and Y is subjected to methanolysis (to remove it from the resin) and is characterized by ¹H NMR spectroscope. The relevant data include: (CDCl₃) 5.58 ppm (d, J=5.3 Hz, H1 of thiosugar), 5.47 ppm (dd, J=7.9, 10.2 Hz, H2 of C2 pivaloylated sugar), 4.45 ppm (d, partially overlapped, H1 of C2 pivaloylated sugar).

6.11. Synthesis Of An α-Linked Disaccharide On The Solid Phase

The sodium salt of a glycosyl acceptor (X, FIG. 7) is attached to the Merrifield resin by the standard method (DMF, 80° C., 24 h). Following the coupling and rinsing (as described in Example 6.10), the resin is lyophilized and weighed. Loading is calculated at 0.52 mmol/g from the mass gain.

200 mg (i.e., 0.1 mmol) of derivatized resin is lyophilized overnight in the reaction vessel (FIG. 7) and then purged for 1 hour with argon. The resin is then suspended in 5 mL methylene chloride. 4 equivalents (0.4 mmol) of perbenzylated fucosyl sulfoxide Y and 6 equivalents of 2,6-di-t-butyl-4-methyl pyridine are dissolved in 5 mL methylene chloride and added by syringe to the reactor vessel. The mixture is agitated gently by argon flow for 30 minutes at room temperature and then the reactor vessel is immersed in a cold bath and allowed to cool to –60° C. 2 equivalents (0.22 mmol) of triflic anhydride diluted one hundred fold in methylene chloride are added slowly by syringe (over 15 minutes) to the reaction vessel. The reaction is gently agitated for 1 hour. The solvent and unbound reagents are then drained from the reactor vessel, and the resin mixture is rinsed repeatedly with methanol followed by methylene chloride. Subsequently the resin mixture is suspended in 15 mL of methylene chloride and then treated with excess Hg(OCOCF$_3$)$_2$ for 8 hours to cleave the glycosidic linkage to the resin (only 5 minutes is required to remove sufficient product from the resin to monitor the reaction by TLC analysis). The solvent is allowed to drain from the resin as before. The resin is then rinsed with additional solvent and the filtrates combined, extracted three times with water, and concentrated by evaporation. Flash chromatography on silica gel gives only the desired α-linked disaccharide.

Figure 7:
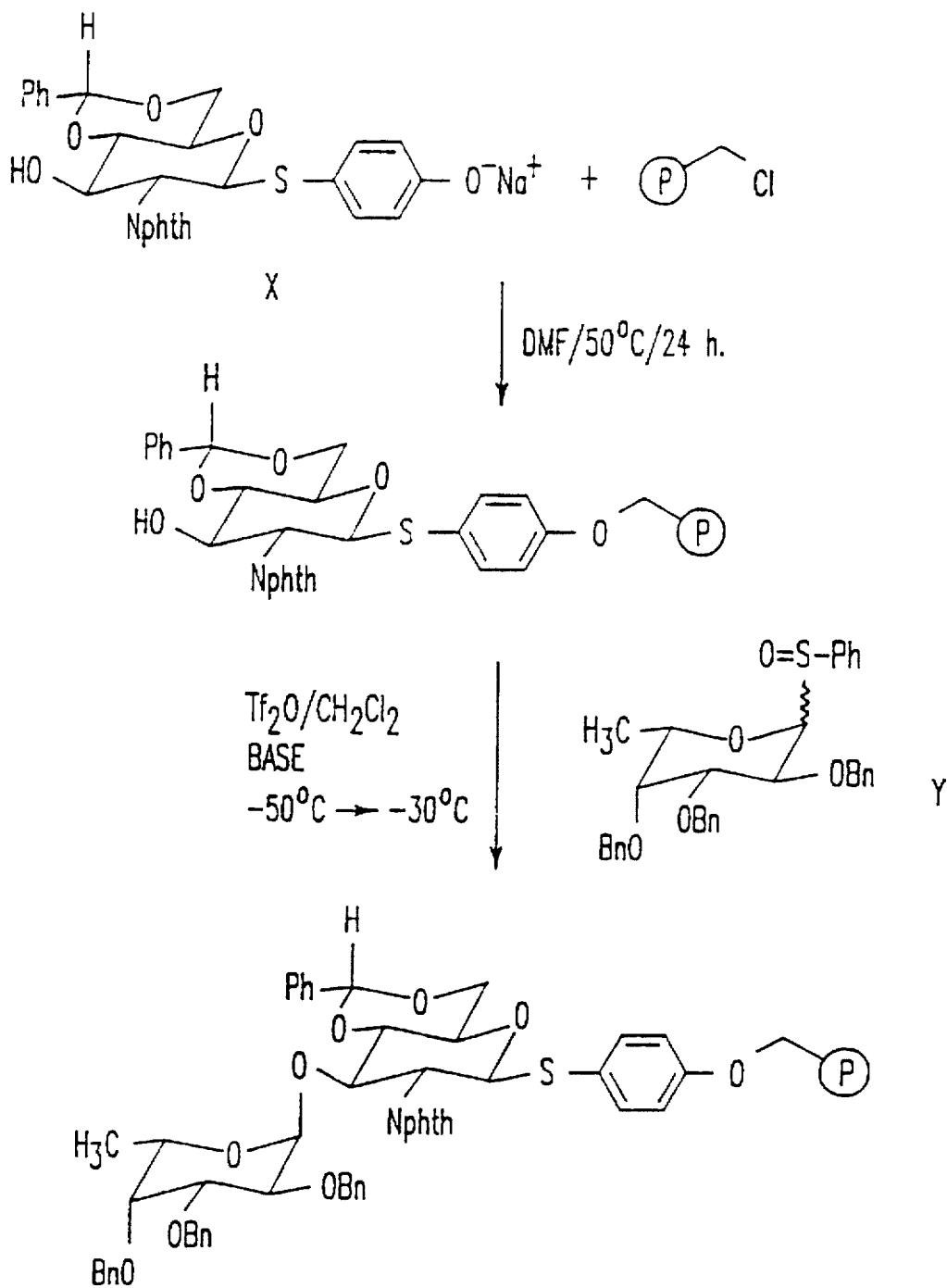
FIG. 7 illustrates the general scheme for synthesis of an α-linked disaccharide on the solid phase.

Thiosugar X in FIG. 7 is prepared from the readily available corresponding glucosamine by treatment with the following reagents: (1) phthalic anhydride; (2) acetic anhydride; (3) tetrachlorotin-4-hydroxy thiophenol; (4) hydroxide; (5) benzaldehyde-H$^+$; (6) NaH, under conditions that are standard in the art. (See, Section 6.15, below).

Sulfoxide Y in FIG. 7 is made from peracetylated fucose by treating the starting material sequentially with BF$_3$/etherate-thiophenol, followed by hydroxide, followed by benzyl bromide, and then with mCPBA. All these steps are standard and well known in the art.

The disaccharide produced from the reaction of X and Y following treatment with Hg(OCOCF$_3$)$_2$ (to remove it from the resin) is characterized by $^1$H NMR. Relevant data: CDCl$_3$) 5.6 ppm (apparent t, J=7.6 Hz, H1 of C2 phthalimido sugar), 3.35 ppm (d, J=7.6 Hz, lactol OH, i.e., of phthalimido sugar after hydrolytic removal from resin w/Hg (II), 4.9 ppm (d, J=2.8 Hz, H1 of fucose derivative).

6.12. Solid Phase Synthesis Of Lewis X Trisaccharide

The sodium salt of a glycosyl acceptor (X, FIG. 8) is attached to the Merrifield resin using the standard method (DMF, 80° C., 24 h). After using the general linking procedure described in detail in Example 6.10, the anhydrous resin is suspended in 5 mL methylene chloride. 4 eq. 2,3,4,6-pivaloylated galactosyl sulfoxide Y and 6 eq. base (as above) is dissolved in 5 mL methylene chloride. The reagent solution is then added to the resin, and the reaction mixture is cooled to −60° C. 2 equivalents of triflic anhydride diluted one hundred fold (v/v) in methylene chloride are then added.

After 30 minutes, the resin is "drained" and rinsed repeatedly with methylene chloride and methanol. The resin is then suspended in 5 mL methylene chloride and cooled to 0° C. 5 mL of a 1:2 solution of trifluoroacetic acid/methylene chloride is then added, and the resin is agitated gently for 5 hours. The resin is then "drained" and rinsed repeatedly with methylene chloride and methanol. Following a final rinse with anhydrous methylene chloride, the resin is suspended in 5 mL of anhydrous methylene chloride. 4 equivalents of 2,3,4-triethylsilyl fucosyl sulfoxide Z and 6 equivalents of hindered base (i.e., that used above) are dissolved in 5 mL methylene chloride and added to the resin. The reaction mixture is cooled to −60° C. 2 equivalents of triflic anhydride are diluted 100 fold in methylene chloride and added slowly by syringe to the reaction. After agitating gently for 30 minutes, the resin is "drained" and rinsed. The trisaccharide is then removed and isolated from the resin using Hg(OCOCF$_3$)$_2$, as described above in Example 6.10.

Figure 8:
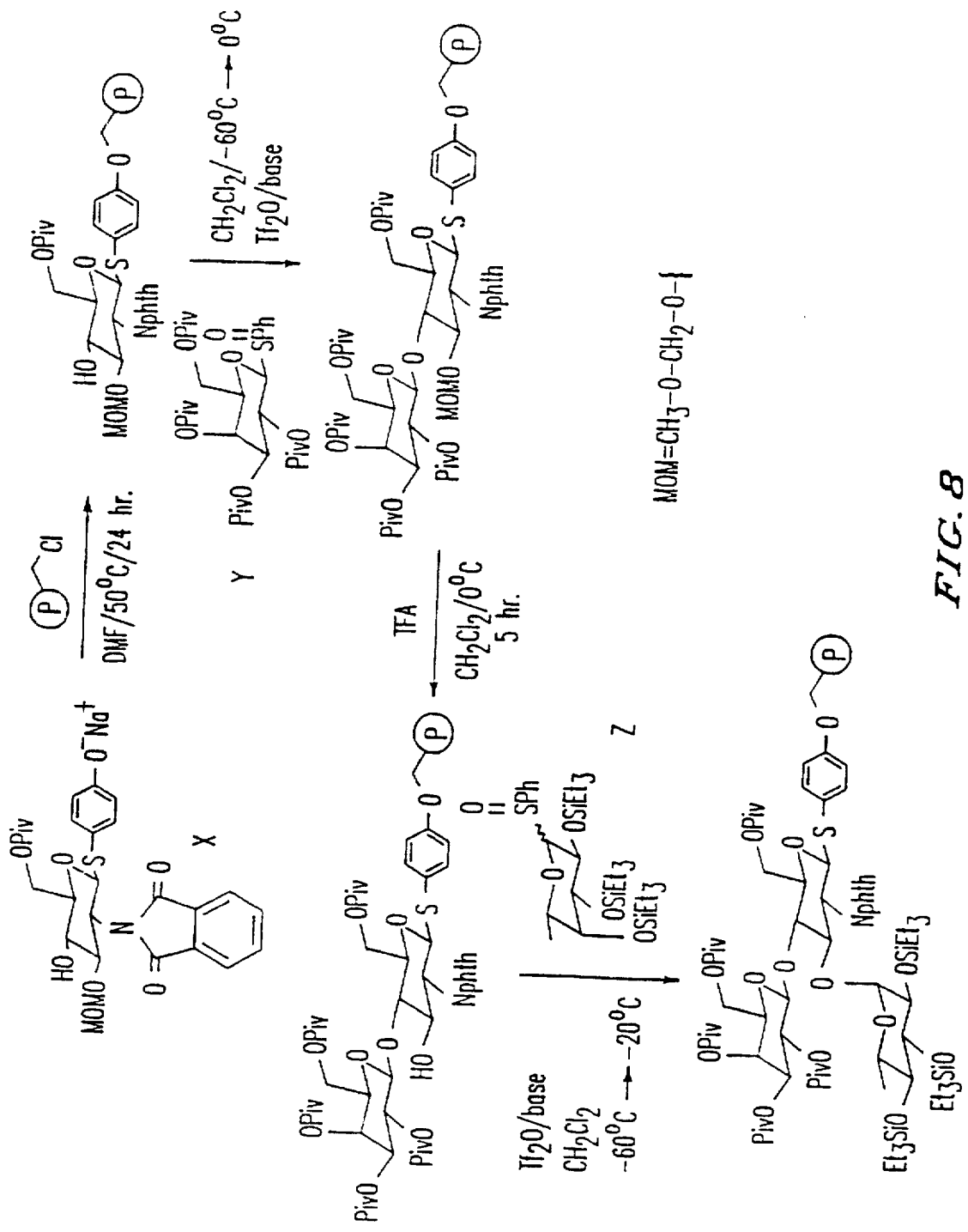
FIG. 8 illustrates the general scheme for synthesis of a trisaccharide on the solid phase.

Thiosugar X in FIG. 8, is prepared from the readily available glucosamine by treatment with (1) phthalic anhydride; (2) acetic anhydride; (3) tetrachlorotin-4-hydroxy thiophenol; (4) benzyl bromide; (5) hydroxide; (6) benzaldehyde-H$^+$; (7) chloromethyl methyl ether (MOM chloride); (8) H$_2$O/H$^+$; (9) pivalyoyl chloride; (10) hydrogenation, Pd(OH)$_2$; (11) NaH. Again, all steps are standard including the conditions for the deprotection of the benzyl protecting group on the 4-hydroxy thiophenyl glycoside, which conditions are typical for debenzylation. In the debenzylation step, no cleavage of the sugar to sulfur bond is observed.

Sulfoxide Y in FIG. 8 is prepared by treating perpivaloylated galactose with BF$_3$/etherate-thiophenol, followed by mCPBA.

Sulfoxide Z in FIG. 8 is prepared by treating peracetylated fucose with BF$_3$/etherate-thiophenol, followed sequentially by hydroxide, triethylsilyl chloride, and mCPBA.

Similarly, other Lewis blood group sugars are synthesized readily, including, but not limited to, Lewis A and Lewis B.

6.13. Additional Experiments Conducted in the Solid Phase

Referring to FIG. 16, in particular, cesium fluoride (157.2 mg, 1.03 mmol, 1.1 eq.) and Merrifield resin (1 mol. eq. Cl per gram) (1.0975 g, 1.10 mol, 1.1 eq.) are added to a solution of freshly prepared 1 (803.5 mg, 0.94 mmol, 1.0 eq.) in DMF (20 mL). The resulting suspension is shaken mechanically under an argon atmosphere at 60° C. for 24 h. The sugar-derivatized resin is then isolated by vacuum filtration and washed with DMF (3×10 mL), methanol (3×10 mL) and CH$_2$Cl$_2$ (5×10 mL) and then dried under vacuum overnight to give resin 2 (1.4738 g, calculated based on mass gain, or 0.34 mmol/g). IR (KBr disc) 1734 cm$^{-1}$ (v, C=O).

Resin 2 is then washed with 10% trifluoroacetic acid in CH$_2$Cl$_2$ (20 mL) to remove the protecting group. Subsequently, the deprotected resin 3 is washed with CH$_2$Cl$_2$ (10×10 mL) and dried under vacuum overnight. IR (KBr disc) 1734 cm$^{-1}$ (v, C=O), 3430 cm$^{-1}$ (br, v, O—H).

To obtain resin 5, 3 (95.4 mg) is added to a solution of the sulfoxide 4 (122.1 mg, 0.156 mmol, 1.0 eq.) and 2,6-di-tert-butyl-4-methyl-pyridine (98.2 mg, 0.468 mmol, 3.0 eq.) in CH$_2$Cl$_2$ (7.0 mL) and the suspension cooled to −78° C. After 10 mins, triflic anhydride (13.1 μL, 0.078 mmol, 0.5 eq.) in CH$_2$Cl$_2$ (5.0 mL) is added dropwise over a period of 20 mins. Ten minutes after the addition is complete, the reaction is warmed to −60° C. over a period of 20 mins. The reaction is quenched by the addition of saturated NaHCO$_3$. The resin is collected by suction filtration and washed with methanol (2×10 mL), water (1×10 mL), methanol (1×10 mL), and then CH$_2$Cl$_2$ (10×10 mL). The product resin 5 is then dried under vacuum overnight, after which the glycosylation is repeated.

The product resin 6 is obtained as follows: resin 5 (112.7 mg) is washed with 10% trifluoroacetic acid in CH$_2$Cl$_2$ (20 mL). It is then washed with CH$_2$Cl$_2$ (10×10 mL) and dried under vacuum overnight.

Then resin 7 is obtained from resin 6 as follows: resin 6 (110.7 mg) is added to a solution of sulfoxide 4 (123.5 mg, 0.158 mmol, 1.0 eq.) and 2,6-di-tert-butyl-4-methyl-pyridine (99.3 mg, 0.474 mmol, 3.0 eq.) in CH$_2$Cl$_2$ (7.0 mL) and the suspension cooled to −78° C. After 10 mins, triflic anhydride (13.3 μL, 0.079 mmol, 0.5 eq.) in CH$_2$Cl$_2$ (5.0 mL) is added dropwise over a period of 20 mins. Ten minutes after the addition is complete, the reaction is warmed to −60° C. over a period of 20 mins. The reaction is quenched by the addition of saturated NaHCO$_3$. The resin is isolated by filtration and washed with methanol (2×10 mL), water (1×10 mL), methanol (1×10 mL), and then CH$_2$Cl$_2$ (10×10 mL). The product resin 7 is dried under vacuum overnight, after which the glycosylation is repeated.

Finally, compound 8 is obtained from resin 7 as follows: resin 7 (113.6 mg) is washed with 10% trifluoroacetic acid in CH$_2$Cl$_2$ (20 mL). It is then washed with CH$_2$Cl$_2$ (10×10 mL) and suspended in pyridine (10 mL). Acetic anhydride (183.7 μL, 1.932 mmol, 1.0 eq.) and 4-dimethylaminopyridine (4.7 mg, 0.039 mmol, 0.02 eq.)

are added to the suspension under argon. The mixture is stirred overnight and then quenched by the addition of methanol (200 μL). The resin is isolated by filtration and washed with methanol (2×10 mL) and $CH_2Cl_2$ (10×10 mL). The free compound 8 is released from the resin by treatment with bis(trifluoroacetato)mercury(II) in wet methylene chloride, as described below, for example, for the synthesis of disaccharide 13. (Compound 8) $^1H$ NMR (500 MHz, $CDCl_3$) δ4.42 (d, J=8.06 Hz, $H_1$"), 4.49 (d, J=8.06 Hz, $H_1$'), 6.27 (d, J=3.67 Hz, $H_1$). $^{13}C$ NMR (69 MHz, $CDCl_3$) δ91.6, 101.0, 101.3 (anomeric carbon atoms).

6.14. Solid Phase Synthesis of Disaccharides 13 and 16

According to the scheme of FIG. 17, the Pht-protected N-acetylglucosamine residue 9 is attached to a solid support, as follows: Merrifield resin (1.4075 g, 1% cross-linked, chloromethylated styrene/divinylbenzene copolymer, approximately 1 mmol Cl/g, Aldrich) is added to a solution of freshly prepared 9 (1.42 g, 2.693 mmol) in DMF (20 mL). The suspension is shaken mechanically at 60° C. under argon for 24 h. The sugar-derivatized resin is isolated by filtration, washed with DMF (5×10 mL), methanol (3×10 mL) and $CH_2Cl_2$ (10×10 mL), and dried under vacuum overnight to give 1.7466 g of resin-attached 10. The level of loading is calculated to be 0.414 mmol/g (based on mass gain). IR (KBr) 1670, 1716 $cm^{-1}$ (v, C=O); 3470 $cm^{-1}$ (v, C=O).

Resin 10 is coupled to sulfoxide 11, a fucose unit, to give 12 (α-glycosidic linkage), as follows: Compound 10 (218.4 mg) is added to a solution of sulfoxide 11 (204.1 mg, 0.3766 mmol, 1.0 eq.) and 2,6-di-tert-butylpyridine (236.7 mg, 1.1297 mmol, 3.0 eq.) in $CH_2Cl_2$ (7 mL). The suspension is cooled to −60° C. and, after 10 mins, a solution of triflic anhydride (31.7 μL, 0.1883 mmol, 0.5 eq.) in $CH_2Cl_2$ (5 mL) is added dropwise over a period of 20 mins. Ten minutes after the addition is complete, the reaction is slowly warmed to −30° C. and, after 30 mins, quenched by the addition of saturated aqueous sodium bicarbonate. The resin is isolated by filtration, washed with methanol (2×10 mL), water (2×10 mL), methanol (10 mL) and $CH_2Cl_2$ (10×10 mL), and dried under vacuum overnight to give 12.

The final product 13 is obtained as follows: $Hg(OCOCF_3)_2$ (120.5 mg, 0.2824 mmol) and water (a few drops) are added to a suspension of 12 (222.0 mg) in $CH_2Cl_2$ (20 mL). After 5 h the mixture is filtered through cotton. The filtrate is washed with saturated sodium bicarbonate, dried over $Na_2SO_4$, filtered, and concentrated in vacuo. The residue is purified by flash chromatography (35% EtOAC-pet. ether) to give 33.9 mg of 13 (59% yield) as a colorless solid. This solid could be purified further by RP-HPLC (C-18 column, 60 to 98% MeCN in water over 30 mins), $R_T$ 15.7 mins. $^1H$ NMR (500 MHz, $CDCl_3$) δ4.81 (d, J=3.66 Hz, H1 of fucose unit), 5.59 (d, J=8.42 Hz, H1 of glucosamine unit). $^{13}C$ NMR (69 MHz, $CDCl_3$) δ81.9, 93.3, 101.2 (anomeric carbon atoms).

Similarly, the resin 10 can be coupled to a galactose unit, 14, to provide resin 15 (β-glycosidic linkage), as follows: Compound 10 (184.0 mg, 0.414 meq./g) is added to a solution of sulfoxide 14 (208.0 mg, 0.325 mmol) and 2,6-di-tert-butylpyridine (204.3 mg, 0.975 mmol) in $CH_2Cl_2$ (7 mL). The suspension is cooled to −60° C. and, after 10 mins, a solution of triflic anhydride (31.7 μL, 0.1883 mmol, 0.5 eq.) in $CH_2Cl_2$ (5 mL) is added dropwise over a period of 20 mins. Ten minutes after the addition is complete, the reaction is slowly warmed to −30° C. and, after 30 mins, quenched by the addition of saturated aqueous sodium bicarbonate. The resin is isolated by filtration, washed with methanol (2×10 mL), water (2×10 mL), methanol (10 mL) and $CH_2Cl_2$ (10×10 mL), and dried under vacuum overnight to give 15. To obtain best results, the glycosylation procedure is repeated twice.

The product is removed from the resin using the Hg(II) reagent. $Hg(OCOCF_3)_2$ (325.0 mg, 0.2824 mmol) and water (a few drops) are added to a suspension of 15 (222.0 mg) in $CH_2Cl_2$ (20 mL). After 5 h the mixture is filtered through cotton. The filtrate is washed with saturated sodium bicarbonate, dried over $Na_2SO_4$, filtered, and concentrated in vacuo. The residue is purified by flash chromatography (35% EtOAC-pet. ether) to give 19.4 mg of 16 (28% yield). This product could be purified further by RP-HPLC (C-18 column, 60–95% MeCN in $H_2O$ over 30 mins), $R_T$=26.1 mins. $^1H$ NMR (500 MHz, $CDCl_3$) δ4.69 (d, J=7.69 Hz, $H_1$ of galactose residue), 5.32 (dd, J=7.32, 8.8 Hz, $H_1$ of glucosamine residue). $^{13}C$ NMR (69 MHz, $CDCl_3$) δ93.5, 98.8, 101.7 (anomeric carbons).

6.15. Standard References

Most of the transformations mentioned above (protection: benzylation, benzylidenation, acetonation, esterification, and carbo- or silylethentication of sugars; deprotection: debenzylation, acidic hydrolysis of benzylidenes or acetonates, basic hydrolysis of esters, removal of silyl groups with fluoride or under acidic conditions) are described in Binkley, R. W. *Modern Carbohydrate Chemistry*, Marcel Dekker, Inc.: New York, 1988. Methods to convert lactols or anomeric esters or anomeric esters to thiophenyl groups (to produce thiophenyl glycosides) are well known. See, e.g., Ferrier et al. *Carbohydr. Res.* 1973, 27, 55; Mukaiyama et al. *Chem. Lett.* 1979, 487; Van Cleve *Carbohydr. Res.* 1979, 70, 161; Hanessian et al. *Carbohydr. Res.* 1980, 80, C17; Garegg et al. *Carbohydr. Res.* 1983, 116, 162; and Nicolaou et al. *J. Am. Chem. Soc.* 1983, 105, 2430.

From the principles established herein, it should be apparent to one of ordinary skill in the art that the ability to manipulate the reactivity of both glycosyl donors and glycosyl acceptors to control the order in which glycosylation takes place can be exploited to synthesize many other oligosaccharides or glycoconjugates rapidly, efficiently and in high yield, under either homogeneous (in solution) or heterogeous (in the solid phase) conditions.

What is claimed is:

1. A catalytic method of forming a glycosidic linkage comprising:

(a) providing a mixture comprising a glycosyl donor (GD), bearing an anomeric sulfoxide group, and a glycosyl acceptor (GA), having glycosyl accepting characteristics, in an organic solvent under anhydrous conditions;

(b) cooling said mixture below ambient temperature;

(c) adding to said mixture a catalytic amount of an activating agent (AG) effective to activate said anomeric sulfoxide group of said GD;

(d) allowing a catalytic reaction to proceed under conditions effective to provide the formation of a glycosidic linkage between said GD and said GA.

2. The method of claim 1 in which said mixture further comprises a sulfenic acid scavenging agent (SASA), said SASA effective to sequester any sulfenic acid formed in the course of said reaction.

3. The method of claim 1 in which said cooling step includes cooling said mixture to a temperature below −30° C.

4. The method of claim 1 in which said cooling step includes cooling said mixture to −78° C.

5. The method of claim 4 in which the conditions of step (d) include allowing the reaction mixture to warm above −78° C.

6. The method of claim 1 in which said mixture includes a GD that comprises a 2-deoxy GD.

7. The method of claim 1 in which said mixture includes a GA that bears a nucleophilic group.

8. The method of claim 7 in which said nucleophilic group comprises an unprotected hydroxyl group.

9. The method of claim 7 in which said nucleophilic group comprises a blocked hydroxyl group.

10. The method of claim 9 in which the blocked hydroxyl group is blocked by a silyl protecting group.

11. The method of claim 1 in which said AG comprises triflic acid.

12. The method of claim 1 in which said SASA comprises excess methyl propiolate.

13. A catalytic method of forming a glycosidic linkage comprising:

(a) providing a mixture comprising a glycosyl donor (GD), bearing an anomeric sulfoxide group, and a glycosyl acceptor (GA), having glycosyl accepting characteristics, in an organic solvent under anhydrous conditions;

(b) cooling said mixture below −30° C.;

(c) adding to said mixture a catalytic amount of an activating agent (AG), comprising triflic acid, effective to activate said anomeric sulfoxide group of said GD;

(d) allowing a catalytic reaction to proceed under conditions effective to provide the formation of a glycosidic linkage between said GD and said GA.

14. The method of claim 13 in which said mixture further comprises excess sulfenic acid scavenging agent (SASA), said excess SASA effective to sequester any sulfenic acid formed in the course of said reaction.

15. The method of claim 13 in which said mixture includes a GA that bears a nucleophilic group.

16. A catalytic method of forming a glycosidic linkage comprising:

(a) providing a mixture comprising a glycosyl donor (GD), bearing an anomeric sulfoxide group, and a glycosyl acceptor (GA), bearing a nucleophilic group blocked by a silyl protecting group, in an organic solvent under anhydrous conditions;

(b) cooling said mixture to about −78° C.;

(c) adding to said mixture a catalytic amount of an activating agent (AG), comprising triflic acid, effective to activate said anomeric sulfoxide group of said GD;

(d) allowing a catalytic reaction to proceed under conditions effective to provide the formation of a glycosidic linkage between said GD and said GA.

17. The method of claim 1 in which said mixture includes a GA and a GD dissolved in the organic solvent.

18. The method of claim 1 in which said mixture includes a GA or GD bound to a solid resin.

19. The method of claim 1 in which said mixture includes a GD dissolved in the organic solvent and a GA bound to a solid resin.

20. The method of claim 1 in which said mixture includes a GD present in an equimolar amount relative to a GA.

21. The method of claim 1 in which said mixture includes a GD present in an amount that is about one-and-a-half molar equivalents relative to a GA.

22. The method of claim 1 in which said mixture includes an AG present in an amount that is about 0.05 molar equivalents relative to a GA.

23. The method of claim 1 in which said mixture includes a SASA present in an amount that is about twenty molar equivalents relative to a GA.

24. The method of claim 1 in which the organic solvent comprises methylene chloride.

25. The method of claim 13 in which said mixture includes a GD that comprises a 2-deoxy GD.

26. The method of claim 16 in which said mixture includes a GD that comprises a 2-deoxy GD.

* * * * *

UNITED STATES PATENT AND TRADEMARK OFFICE
CERTIFICATE OF CORRECTION

PATENT NO. : 5,792,839

DATED : August 11, 1998

INVENTOR(S) : Daniel E. Kahne

It is certified that error appears in the above-identified patent and that said Letters Patent is hereby corrected as shown below:

Column 1, line 12,
    Insert under "Cross-Reference to Related Applications" the following statement:

--Aspects of the present invention were supported by HHS R01 GM42733, HHS/NRSA F32 GM15051, and ONRN0014-91-J-1230. The United States Government has certain rights in the invention.--

Signed and Sealed this

Fifteenth Day of June, 1999

Attest:

Q. TODD DICKINSON

Attesting Officer        Acting Commissioner of Patents and Trademarks